United States Patent
Kar et al.

(10) Patent No.: US 11,851,462 B2
(45) Date of Patent: *Dec. 26, 2023

(54) TARGETING G3BP AGGREGATION TO PREVENT NEURODEGENERATION

(71) Applicant: University of South Carolina, Columbia, SC (US)

(72) Inventors: Amar N. Kar, Lexington, SC (US); Pabitra Sahoo, West Columbia, SC (US); Jeffery Twiss, Columbia, SC (US); Sean McGill, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,096

(22) Filed: May 22, 2020

(65) Prior Publication Data

US 2021/0024591 A1 Jan. 28, 2021

Related U.S. Application Data

(60) Provisional application No. 62/876,852, filed on Jul. 22, 2019.

(51) Int. Cl.
| | |
|---|---|
| *C07K 14/435* | (2006.01) |
| *C07K 7/08* | (2006.01) |
| *A61P 25/28* | (2006.01) |
| *A61K 38/00* | (2006.01) |

(52) U.S. Cl.
CPC ............ *C07K 14/435* (2013.01); *A61P 25/28* (2018.01); *C07K 7/08* (2013.01); *A61K 38/00* (2013.01)

(58) Field of Classification Search
CPC ......... C07K 14/435; C07K 7/08; A61P 25/28; A61K 38/00
See application file for complete search history.

(56) References Cited

U.S. PATENT DOCUMENTS

| | | | | |
|---|---|---|---|---|
| 10,668,128 B2 * | 6/2020 | Twiss | ...................... | A61K 38/10 |
| 2015/0045330 A1 * | 2/2015 | Inoue | ...................... | A61K 31/60 |
| | | | | 514/159 |
| 2015/0164891 A1 * | 6/2015 | Hornstein | ............... | A61P 25/02 |
| | | | | 514/253.04 |

OTHER PUBLICATIONS

Liu et al., 2013, Reducing TDP-43 aggregation does not prevent its cytotoxicity, ACTA Neuropathologica Communications, 1: 49 (11 pages).*
Sahoo et al., 2018, Axonal G3BP1 stress granule protein limits axonal mRNA translation and nerve regeneration, Nature Communications, 9: 3358 (14 pages).*
Taniuchi et al., 2011, The N-Terminal Domain of G3BP Enhances Cell Motility and Invasion by Posttranscriptional Regulation of BART, Mol Cancer Res, 9(7): 856-866.*
Fung et al., 2013, Production of a Dominant-Negative Fragment Due to G3BP1 Cleavage Contributes to the Disruption of Mitochondria-Associated Protective Stress Granules during CVB3 Infection, PLOS One, 8(11): e79546 (15 pages).*
Tourriere et al., 2003, The RasGAP-associated endoribonuclease G3BP assembles stress granules, The Journal of Cell Biology, 160, 823-831.*

* cited by examiner

*Primary Examiner* — Amber D Steele
(74) *Attorney, Agent, or Firm* — Burr & Forman, LLP; Douglas L. Lineberry

(57) ABSTRACT

Testing peptides in in vitro models of neurodegenerative disorders such as Parkinson's disease, Alzheimer's disease, Frontotemporal dementia, Amyotrophic lateral sclerosis, to evaluate systems and methods of treatment therefore.

14 Claims, 76 Drawing Sheets

Specification includes a Sequence Listing.

TARGETING G3BP AGGREGATION TO PREVENT NEURODEGENERATION

This invention was made with government support under R01 NS041596 awarded by the National Institutes of Health. The government has certain rights in the invention.

BACKGROUND OF THE INVENTION

1) Field of the Invention

The present invention relates to testing peptides in in vitro models of neurodegenerative disorders such as Parkinson's disease, Alzheimer's disease, Frontotemporal dementia, Amyotrophic lateral sclerosis, to evaluate systems and methods of treatment.

2) Description of Related Art

Neurodegenerative disease is a common and growing cause of mortality and morbidity worldwide. Roughly about vie (5) million Americans suffer from Alzheimer's disease (AD); one (1) million from Parkinson's disease (PD); four hundred thousand (400,000) from multiple sclerosis (MS); thirty thousand (30,000) from Amyotrophic lateral sclerosis (ALS), and three thousand (3000) from Huntington's disease (HD).

In recent years, altered RNA processing has emerged as a key contributing factor in several neurodegenerative diseases. Many of the neurodegenerative diseases share features such as protein aggregates containing proteins such as Tau, alpha-synuclein and beta-amyloid, as well as aberrant cytosolic protein complexes consisting of stress granules (SG) associated RNA binding proteins (RBPs), such as TDP-43, FUS and TIA-1. Studies suggest that in a diseased neuron, both altered RBP function and increased cytoplasmic aggregation of RBPs together contribute to the disease progression. There has been limited success in developing potential therapeutic interventions that directly target formation of aberrant SG and cytoplasmic aggregates.

Stress granules are cytosolic inclusions of proteins that function in regulating translation of messenger RNAs during cellular stress, such as heat shock, oxygen deprivation, or oxidative damage. These structures sequester non-essential mRNAs and allow the cell to tailor the production of proteins that help in mitigating the stressful insults. Upon alleviation of stress, the stress granules usually dissipate, and this disassembly correlates with the resumption of widespread protein synthesis. RNA binding proteins such as, T cell intracellular antigen 1 (TIA-1) and RasGAP-associated endoribonuclease (G3BP) nucleate stress granules formation which is followed by recruitment of ribosomal subunits, translation initiations factors and other RBPs.

The potential importance of stress granules in neurodegenerative diseases is highlighted by the number of stress-granule associated-RBPs implicated in the neurodegenerative and neurological disorders such as Ataxin-2 (in spinocerebellar ataxia), survival motor neuron (SMN) (in spino-muscular atrophy), fragile X mental retardation protein (FMRP) (in fragile X syndrome), Tar-DNA binding protein 43 (TDP-43) (in amyotrophic lateral sclerosis (ALS) and fronto-temporal lobar degeneration (FTLD)), fused in sarcoma (FUS) (in ALS) and TIA-1 (in ALS and FTD). Neurodegeneration-associated mutations in the above-mentioned proteins show increased protein aggregation and elevated levels of stress granules with reduced stress granule dynamics.

Current therapeutic interventions for reducing the formation of toxic cytoplasmic aggregates and promoting disassembly of aberrant stress granules have focused on either activating molecular chaperones, e.g., activating heat shock response, to facilitate protein folding or express components of the heat shock response engineered to remove aggregated proteins, e.g. heat shock proteins (HSP 104), or enhance clearance of aggregated proteins via the ubiquitin proteasome system and autophagy. However, limited success has been achieved in determining the efficacy of these interventions in disease development and progression.

This suggested to the inventors of the current disclosure that the formation of pathologically persistence granules contribute significantly to the disease development in neurodegenerative diseases. Accordingly, it is an object of the present disclosure to provide modalities, and systems and methods for use thereof, which may foster the disassembly of stress granules for therapeutic potential and neuro-protection.

SUMMARY OF THE INVENTION

The above objectives are accomplished according to the present invention by providing in a first embodiment, a prophylactic method for blocking stress granule aggregation. The method may include treating a cell with a cell permeable peptide, preventing induced and mediated neurotoxicity, and may disassemble aggregates of stress granules and neurodegeneration-associated RNA binding proteins along axons. Further, the polypeptide may comprise between 19-21 amino acids and may have the amino acid sequence of SEQ ID NO.: 2. Again, induced neurotoxicity may comprise MPP$^+$ induced neurotoxicity. Still, mediated neurotoxicity may comprise Aβ-mediated neurotoxicity. Yet further, the aggregates of stress granule and neurodegeneration-associated RNA binding proteins arise as a pathophysiological event shared between different neurodegeneration-associated stressors. Still yet, the nuerogeneration-associated stressor comprises Parkinson's Disease, Alzheimer's Disease, Frontotemporal Dementia or Amyotrophic Lateral Sclerosis. Again yet, the method may include administering the cell permeable peptide to decrease or prevent loss of neurons. Further yet, the stress granules may comprise G3BP1, TIA1, FMRP, FXR, TDP43 and/or FUS-TLS.

In an alternative embodiment, the current disclosure may provide a prophylactic method for blocking neurogenerative disease associated with axon degeneration comprising. The method may include administering a cell permeable peptide to a cell; administration of the cell permeable peptide may disassemble pathological protein aggregates in neurons, and administration of the cell permeable peptide may prevent RNA binding protein aggregation in axons after exposure to neurotoxins. Further, the polypeptide may comprise between 19-21 amino acids and has the amino acid sequence of SEQ ID NO.: 2. Still yet, the pathological protein aggregates and/or RNA binding protein aggregation arise as a pathophysiological event shared between different neurodegeneration-associated stressors. Further again, the nuerogeneration-associated stressor may comprise Parkinson's Disease, Alzheimer's Disease, Frontotemporal Dementia or Amyotrophic Lateral Sclerosis. Yet still, the cell permeable peptide may decrease or prevent loss of neurons. Still further again, the stress granules may comprise G3BP1, TIA1, FMRP, FXR, TDP43 and/or FUS-TLS.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 144E shows overall levels of these proteins based in exposure matched mages (N≥100 aggregates over three repetitions and *o≤0.01, p≤0.005, p≤0.001 for entire population distributions by Fishers exact test for B and D; N≥25 neurons over 3 repetitions and *p≤0.01, p≤0.005, *p≤0.001 one-way ANOVA with Tukey HSD post-hoc for FIGS. 13E-13F).

Figure 1A:
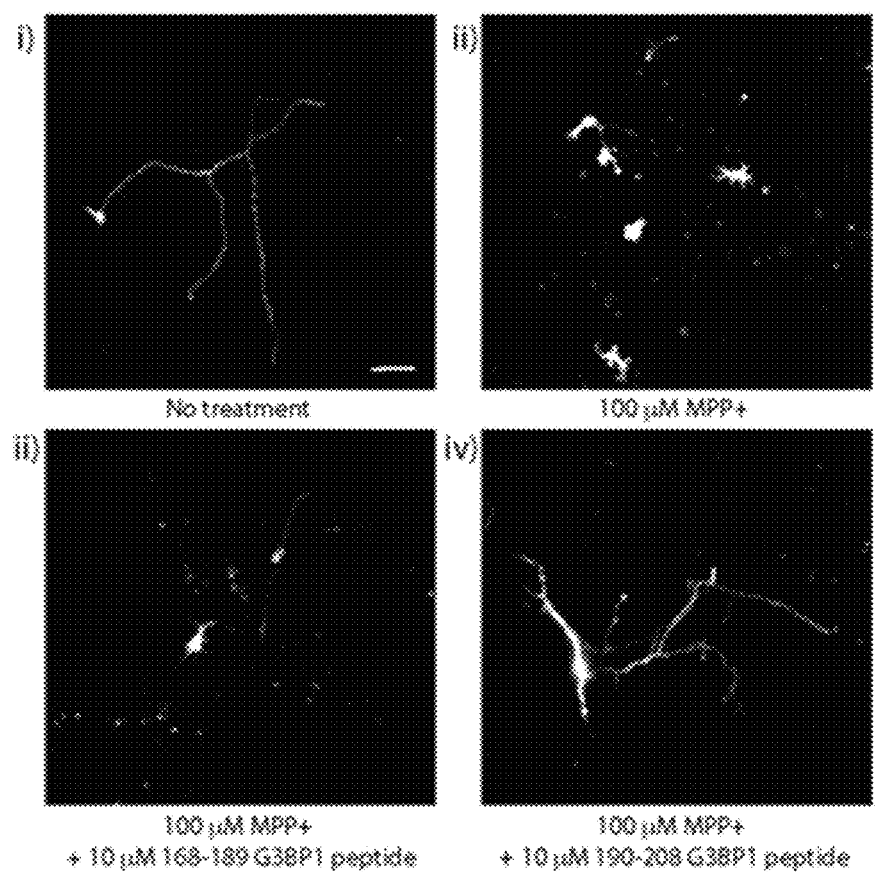
FIG. 1A shows representative images for NF-labeled (white) 7 days in vitro (DIV7) E18 midbrain neurons under control conditions (i) or after treatments with 100 μM MPP+(ii) or 100 μM MPP+ with 190-208 G3BP1 (iv) or control 168-189 peptides.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The current disclosure demonstrates that disassembly of stress granules is neuro-protective across a number of neurodegenerative disorders. Thus, modalities which may foster the disassembly of stress granules would be deemed to have therapeutic potential and are considered as neuro-protective.

The inventors report the application of the cell permeable 190-208 G3BP1 peptide derived from a highly conserved region in G3BP1 and that has been shown to specifically target mRNA storage sites in neurons and increases rates of regeneration after traumatic injury, to neurons exposed to neurodegenerative insults or cells expressing neurodegeneration-associated mutant proteins. Previous studies from the inventors' laboratory have shown that the 190-208 G3BP1 peptide interferes with endogenous stress granule formation possibly by blocking the aggregation of the SC nucleator G3BP1. The 190-208 G3BP1 peptide-treated neurons show reduced degeneration of neurons after treatment with neurotoxins such as MPP+ and beta-amyloid peptide, see infra. In addition, 190-208 G3BP1 peptide treatment reverses the increased protein aggregations and elevated levels of stress granule observed in neurons expressing neurodegeneration-associated mutant alleles of TDP-43 and TIA-1, see infra. The neuroprotective effects of the cell-permeable 190-208 G3BP1 peptide may represent a novel therapeutic lead for ameliorating neurodegeneration.

The potential importance of stress granules in neurodegenerative diseases is highlighted by the number of stress-granule associated-RBPs implicated in neurodegenerative and neurological disorders such as Ataxin-2 (in spinocerebellar ataxia), survival motor neuron (SMN) (in spinomuscular atrophy), fragile X mental retardation protein (FMRP) (in fragile X syndrome), Tar-DNA binding protein 43 (TDP-43) (in amyotrophic lateral sclerosis (ALS) and fronto-temporal lobar degeneration (FTLD)), fused in sarcoma (FUS) (in ALS) and TIA-1 (in ALS and FTD).

Neurodegeneration-associated mutations in the above-mentioned proteins show increased protein aggregation and elevated levels of stress granules with reduced stress granule dynamics. Therefore, suggesting that the formation of these pathologically persistence granules contribute significantly to the disease development in neurodegenerative diseases. Thus, modalities which may foster the disassembly of stress granules would be deemed to have therapeutic potential and are considered as neuro-protective.

Accumulating evidence from neurodegeneration-associated mutations in ribonucleoproteins (RNPs) show that aberrant stress granule (SG) dynamics contribute to initiation and progression of diseases such as ALS, FTD and AD. Stress granules are RNP complexes formed during stress to transiently sequester mRNAs whose protein products are not immediately needed, thus tailoring neuronal protein production to best respond to and survive the insult. Mutations that enhance aggregation of RNA binding proteins or cells exposed to chronic stress and disease lead to formation of atypical SGs, with altered SG dynamics that sequester RNA binding proteins and mRNAs. Moreover, insults that model neurodegeneration in Alzheimer's and Parkinson's diseases result in formation of SGs. These atypical SGs likely contribute to disease pathogenesis and/or progression. The inventors have developed a cell-permeable G3BP1-derived peptide that can block SG protein aggregation and facilitates SG disassembly. Treatment of neurons with this peptide prevents neurotoxin-induced neurodegeneration.

Currently, approximately 20 genes encoding RNA binding proteins have been shown to be mutated in neurodegenerative diseases. An increasing number of these proteins form aberrant protein aggregates and also effect stress granule dynamics, thereby contributing to disease initiation and progression. Thus, alleviating the protein aggregation and restoring homeostatic SG dynamics may prove to be remedial. The currently available strategies focus on enhancing chaperone-mediated refolding of aggregates or improving clearance of the aggregates and SG via the proteasomal and autophagic pathways. However, there is a lack of modalities that directly target stress granule assembly and disassembly. The inventors propose that a cell permeable 190-208 G3BP1 derived peptide can prevent aberrant stress granule aggregation and restore SG dynamics so as to prevent the onset and progression of neurodegeneration.

Several studies have shown that aberrant stress granules aggregates are present in neurons of a number of neurodegenerative, thus suggesting a role for these RNA-protein complexes in disease initiation and progression. However, no reagents have yet been reported that can directly modulate stress granule assembly or disassembly. The inventors herein show that cell permeable 190-208 G3BP1 peptide is able to trigger dissociation of aberrant stress granules formed by expression of ALS and FTD associated mutant proteins and prevent neurotoxin (MPP+ and amyloid)-induced cell death in neurons. The SG disassembly and the neuroprotective effects of the cell-permeable 190-208 G3BP1 peptide represent a novel therapeutic lead for preventing neurodegeneration. The cell permeable G3BP1 190-208 peptide has been shown to trigger endogenous SG disassembly in naïve neurons. Interestingly, treatment of neurons expressing disease-associated mutant proteins with the cell permeable G3BP1 190-208 peptide reduces the aberrant cytoplasmic aggregation observed in neurons and could be a significant target molecule for future drug development.

The inventors have shown that the treatment of neurons with cell permeable G3BP1 190-208 peptide leads to disassembly of stress granules and an increase in axonal protein synthesis. Based on these results, the inventors propose that cell permeable G3BP1 190-208 peptide-mediated disassembly of stress granules is neuroprotective against a number of neurodegenerative insults and may potentially be a novel drug target.

To test whether the triggering disassembly of stress granules would be protective in Parkinson's and Alzheimer's disease, the inventors employed 1-methyl-4-phenylpyridinium (MPP+)-induced and amyloid β (Aβ)-mediated neurotoxicity models. Rat embryonic day 18 (E18) midbrain neurons cultured for 7 days were treated for 16-18 hours with 100 μM MPP+, see FIGS. 1A and B, while E18 cortical neurons were treated with 1 μM Aβ oligomer, see FIGS. 2A-2B, with or without 10 μM G3BP1 190-208 or 168-189 peptide. As a control, the inventors used non-treated neurons.

Figure 2A:
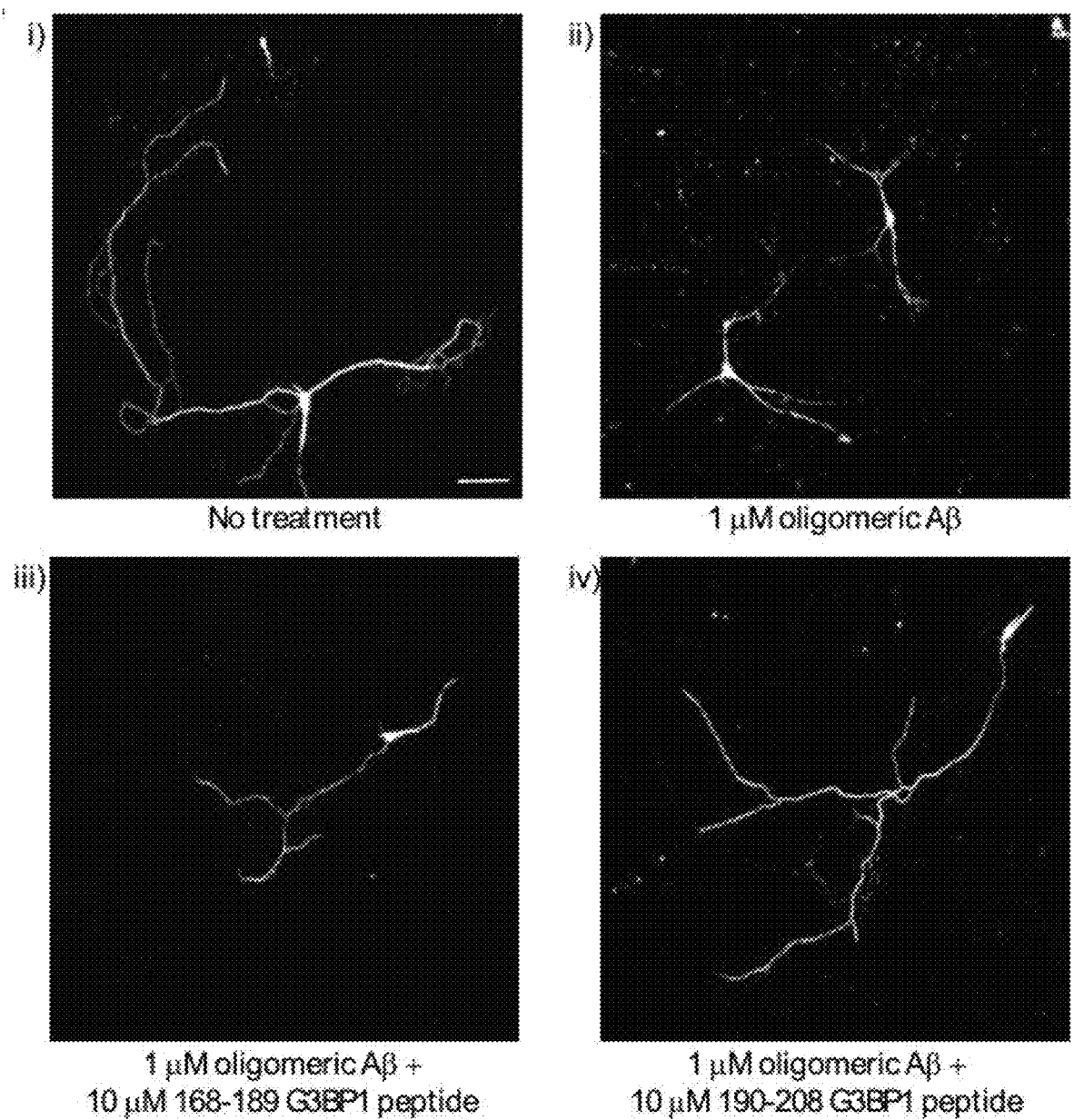
FIG. 2A shows representative images for NF-labeled (white) DIV7 E18 cortical neurons under control conditions (i) or after treatment with 1 μM Aβ (ii) or 1 μM Aβ with 190-208 G3BP1 (iv) or control 168-189 (iii) peptides.
Figure 2B:
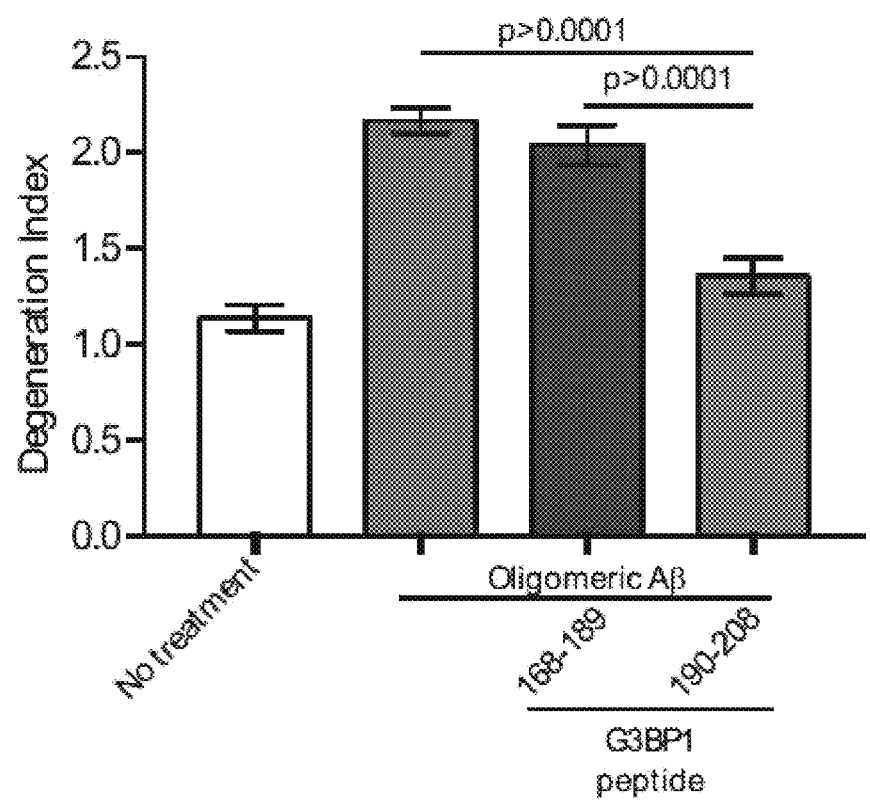
FIG. 2B shows quantification of neurite degeneration in midbrain neurons in control or 1 μM Aβ peptide-treated neurons in the presence of 190-208 G3BP1 or control 168-189 peptides.
Figure 3A:
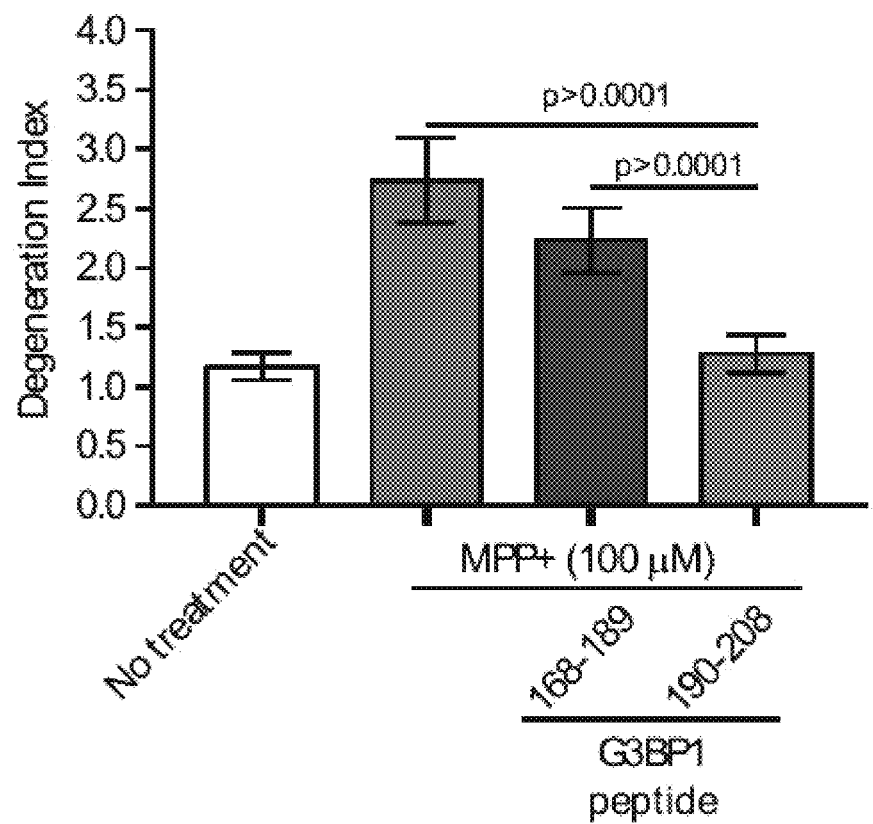
FIG. 3A shows quantification of MPP+-induced degeneration of DIV7 E12.5 motor neuron neurites after exposure of cultures to 100 μM MPP+ and either 10 μM 190-208 G3BP1 or control 168-189 peptides.

The results show that treatment of neurons with G3BP1 190-208 prevented neurite degeneration observed in neurons exposed to neurotoxins MPP+, see FIGS. 1A and B, and Aβ, see FIGS. 2A and B. Next, the inventors tested the efficacy of the G3BP1 190-208 peptides on an in vitro amyotrophic lateral sclerosis (ALS) model, mouse embryonic day 12.5 motor neurons were cultured for 7 days and then treated for 16-18 hours with mitotoxin, 10004 MPP+ with or without 10 μM G3BP1 190-208 or 168-189 peptide. Non-treated cultures were used as controls (FIG. 3A). Treatment with G3BP1 190-208 protected against MPP+-induced degeneration as compared to neurons treated with MPP+ alone or those treated with control G3BP1 168-189. Taken together, these results show that G3BP1 190-208 peptide is protective against neurodegeneration induced by treatment number of neurotoxic insults.

Figure 3B:
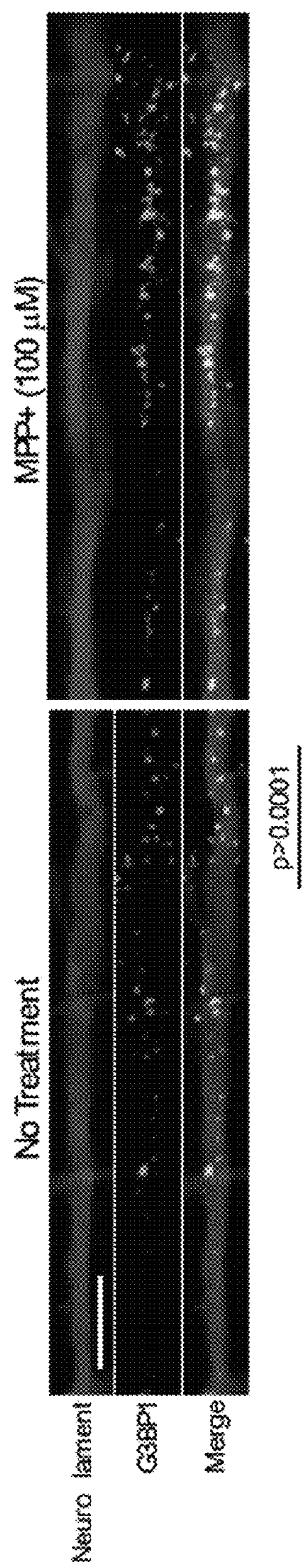
FIG. 3B shows Representative images of G3BP1 (green) and NF-labeled (red) E12.5 motor neurons under control or after treatment with 100 μM MPP [scale bar=10 μm].
Figure 3C:
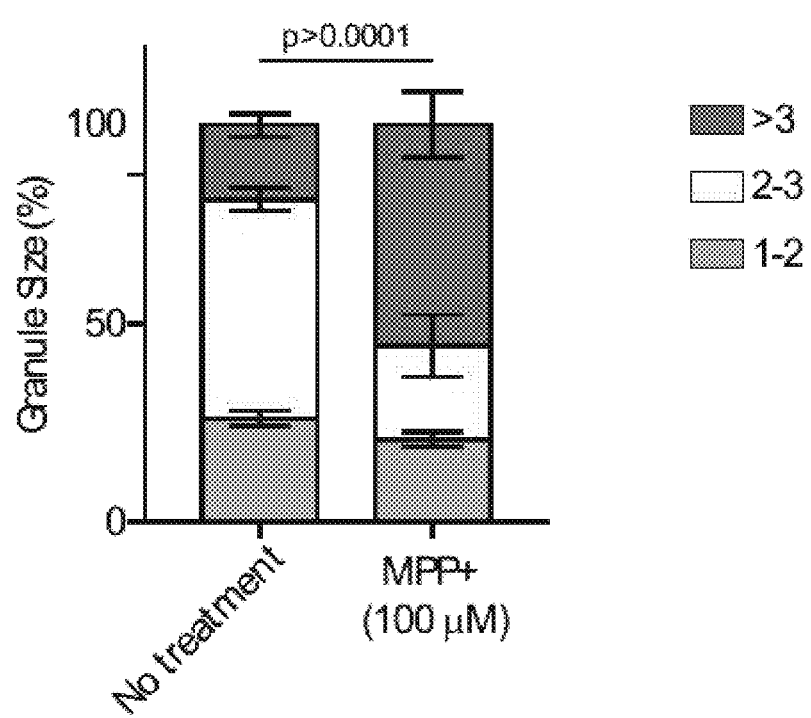
FIG. 3C shows distribution of sizes of endogenous G3BP1 aggregate per 100 μm neurite from motor neurons cultures as treated in FIG. 2B.
Figure 3D:
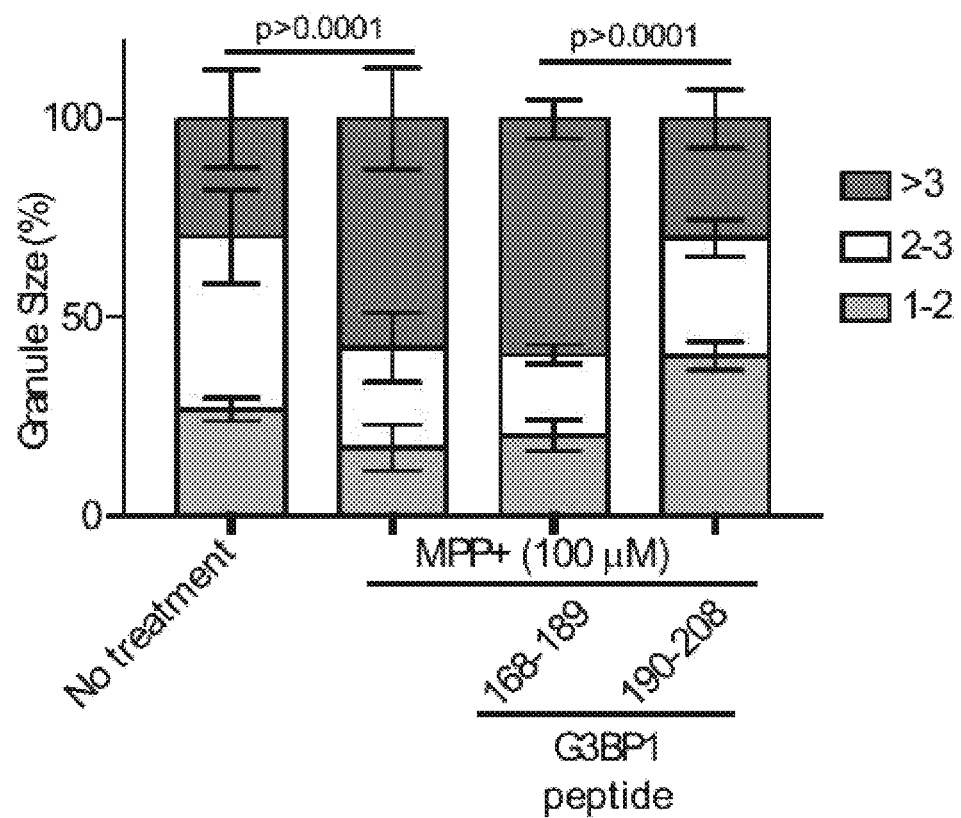
FIG. 3D shows endogenous G3BP1 aggregate sizes per 100 μm neurite indicated as bins for motor neurons either untreated or treated with MPP+ alone or with addition of 10 μM 190-208 G3BP1 or 168-189 control peptide.

Previous studies have shown that, exposure of midbrain neurons results in formation of stress granules. To test whether treatment of motor neurons with mitotoxin MPP+ results in the formation of stress granules the inventors stained the MPP+-treated neurons for G3BP1 protein. The inventors results show that presence of G3BP1 aggregates in non-treated motor neurons and treatment of the neurons with MPP+ results in an increase in G3BP1 aggregates, see FIGS. 3B and 3C. Moreover, treatment of MPP+-treated neurons with G3BP1 190-208 lead to a decrease in the size of aggregates with higher number smaller sized aggregates as compared to control 168-189 peptide, see FIG. 3D.

Figure 4A:
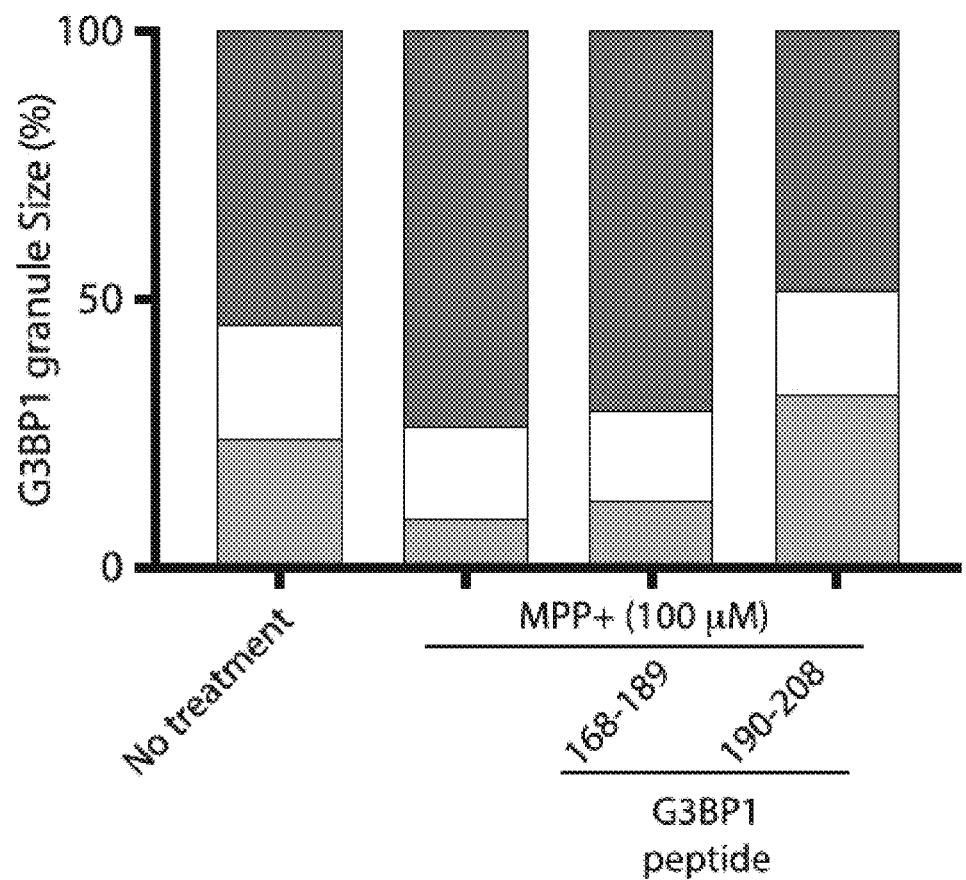
FIG. 4A shows the size of endogenous G3BP1 aggregates per 100 μm of neurite shown as indicated bins from midbrain cultures under control conditions and after treatment with MPP+ alone or with 190-208 G3BP1 or 168-189 peptides.
Figure 4B:
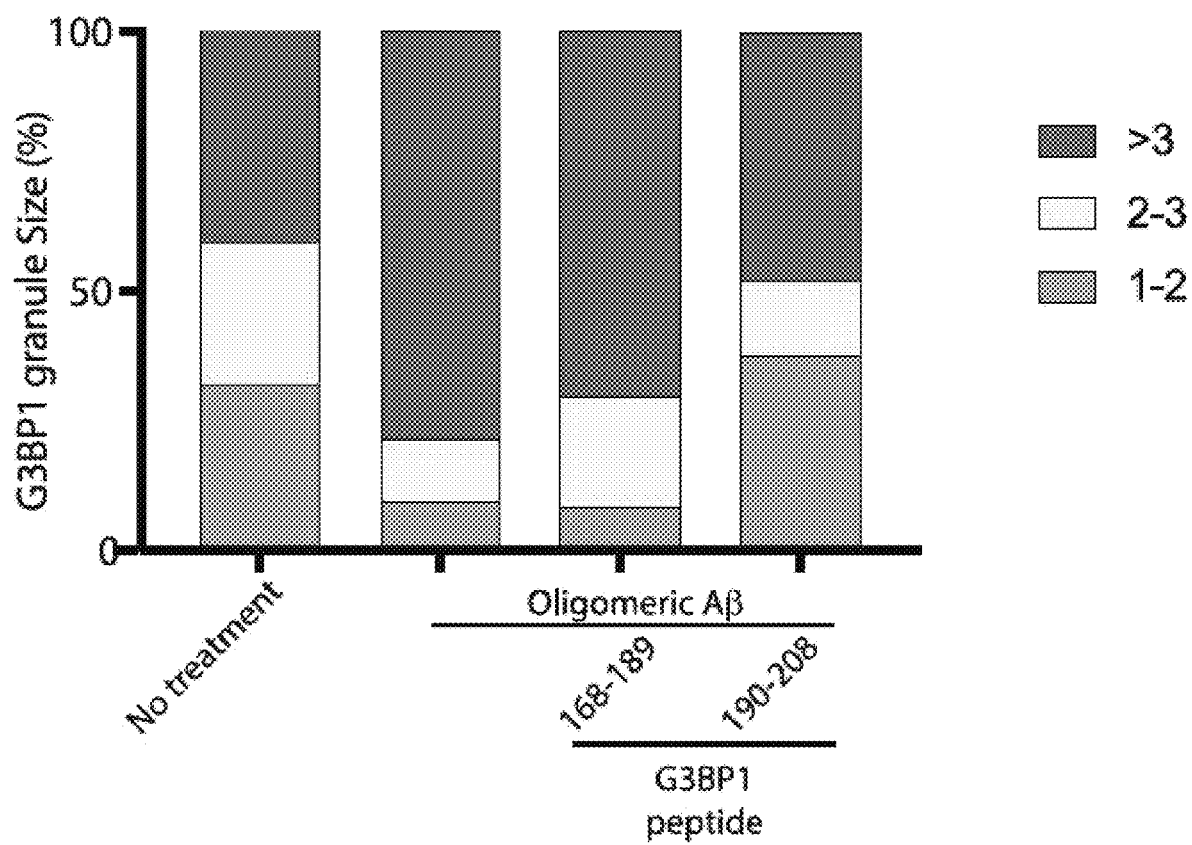
FIG. 4B shows size distribution of endogenous G3BP1 aggregates per 100 μm of neurite shown from cortical neurons treated with 1 μM Aβ peptide or with 10 μM 190-208 G3BP1 or 168-189 control peptide.

Similar increase in endogenous G3BP1 aggregates were observed after treatment of midbrain neurons with MPP+ and cortical neurons with □β oligomers, see FIGS. 4A and 4B. Consistent to the inventors results from motor neurons treated with MPP+, treatment with G3BP1 190-208 peptide leads to a decrease in the size of G3BP1 aggregates in midbrain neurons exposed to MPP+ or cortical neurons treated with □β oligomers. Together, these data indicate that treatment of neurons with neurotoxins results in formation of larger G3BP1 aggregates and that treatment with the G3BP1 190-208 peptide results in decrease in the size of the G3BP1 aggregates. Given that the G3BP1 190-208 peptide prevents degeneration induced by treatment with neurotoxins such as MPP+ and □β oligomer and decreases G3BP1 aggregates formed due MPP+ and Aβ treatment.

Currently, approximately 20 genes encoding RNA binding proteins have been shown to be mutated in neurodegenerative diseases. A number of stress-granule associated-RBPs have been implicated in the neurodegenerative and neurological disorders such as Ataxin-2 (in spinocerebellar ataxia), survival motor neuron (SMN) (in spino muscular atrophy), fragile X mental retardation protein (FMRP) (in fragile X syndrome), TDP-43 (in amyotrophic lateral sclerosis (ALS) and fronto-temporal lobar degeneration (FTLD)), FUS (in ALS) and TIA-1 (in ALS and FTD). An increasing number of these proteins form aberrant protein aggregates and also effect stress granule dynamics, thereby contributing to disease initiation and progression. Thus, alleviating the protein aggregation and restoring homeostatic SG dynamics may prove to be remedial.

Figure 5A:
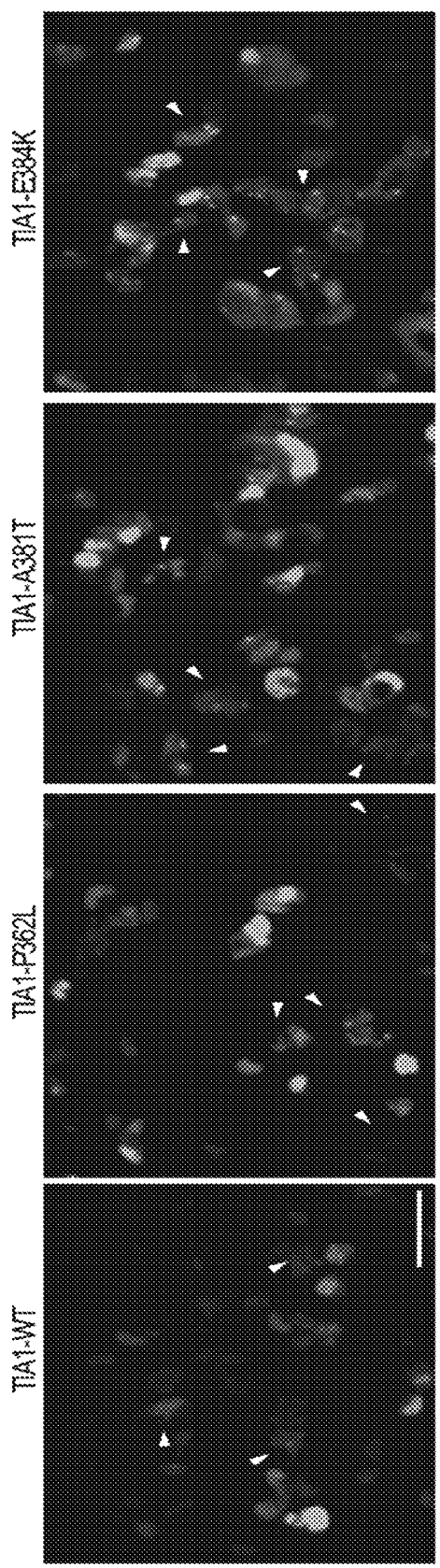
FIG. 5A shows representative images of HEK cells transfected with GFP-tagged wild-type or ALS/FTD-associated mutants (P362L, A381T, or E384K) TIA1.
Figure 5B:
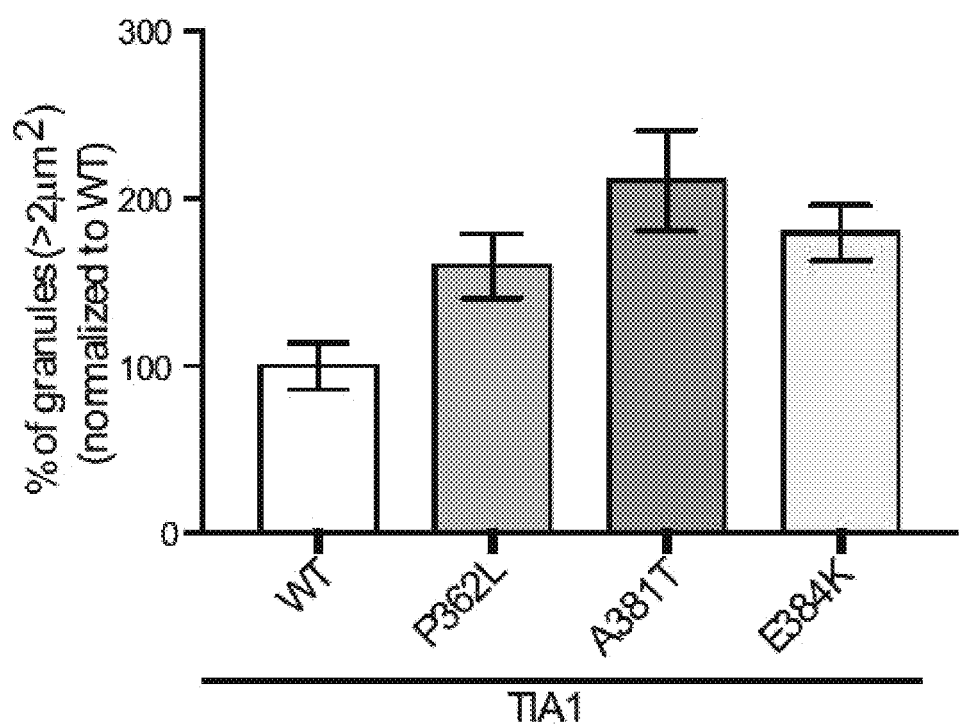
FIG. 5B shows quantification of the percentage of cells with TIA1-GFP puncta greater than 2 μm² area in transfected cells relative TIA1-WT-GFP expressing cells.
Figure 5C:
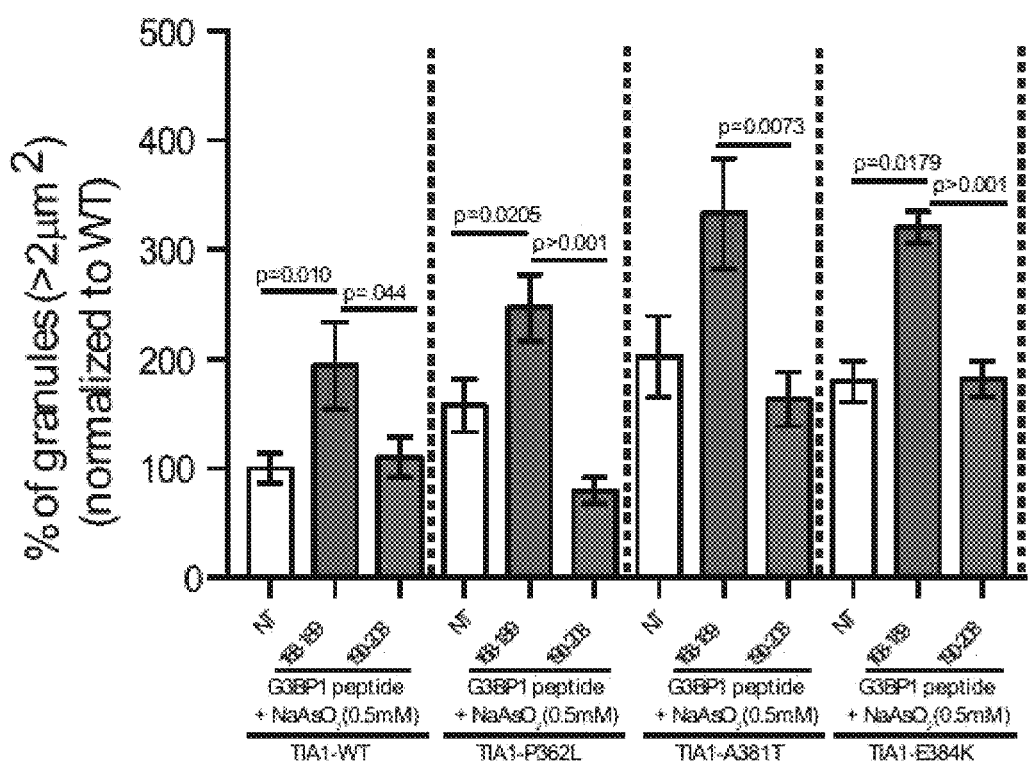
FIG. 5C shows HEK cells expressing TIA1-GFP or ALS/FTD-associated mutants TIA1-P362L, TIA1-A381T, TIA1-E384K treated with sodium arsenite (0.5 mM) for 30 minutes followed by treatment with either 10 μM 190-208 G3BP1 or 168-189 control peptide.

The inventors tested whether the G3BP1 190-208 peptide would prevent the aggregation of granules formed by TIA1 and TDP43 mutant proteins associated with ALS and FTD. The inventors expressed GFP-tagged wild-type or ALS/FTD-associated mutants (P362L, A381T, or E384K) TIA1 in HEK cells and the inventors imaging results show that consistent with previous studies, the ALS/FTD-associated mutants form larger TIA1 granules (>2 μm$^2$), see FIGS. 5A and 5B. Next, we treated HEK cells expressing wild-type and or ALS/FTD-associated mutants (P362L, A381T, or E384K)TIA1, with arsenite a potent inducer of SG aggregation, in addition to either G3BP1 190-208 peptide or control G3BP1 168-189 peptide. Treatment with arsenite increases size of TIA1 aggregates for wild-type and ALS/FTD-associated mutants, however, exposure to G3BP1 190-208 peptide was able to decrease the size of the TIA1 aggregates, while no such change in aggregate size was observed upon treatment with the control peptide, see FIG. 5C. These data suggest that G3BP1 190-208 peptide can affects the aggregation of both wild-type and ALS/FTD-associated TIA1.

To further evaluate whether mutant TIA1 and TDP43 protein aggregates are affected by G3BP1 190-208 peptide, the inventors expressed the mutant proteins in embryonic motor neurons and assessed granules formed in neurites with or without arsenite treatment either in the presence of G3BP1 190-208 or control 168-189 peptide. Arsenite-treatment of motor neurons results in an increase in the size of endogenous TIA1 and G3BP1 aggregates, and addition of G3BP1 190-208 peptide reverses the increase number of these larger granules. Consistent with results observed in HEK cells, arsenite treatment leads to an increase in the number of larger granules (>2 µm$^2$) for both wild-type and mutant TIA1-GFP proteins and the decrease in the number of large granules were observed upon addition of G3BP1 190-208 peptide, while no such effect was observed due to exposure to the control 168-189 peptide. Similar results were observed in neurons expressing flag-tagged wild-type and ALS-associated mutant TDP43, i.e., increased number of large flag-TDP43 aggregates (>2 µm$^2$) were observed in neurites treated with arsenite and this effect was reversed by addition of the G3BP1 190-208 peptide. Taken together, these results suggest that the G3BP1 190-208 not only effects the dynamics G3BP1 granules, but also other stress granule proteins like TIA1 and TDP43 as well as the disease-associated mutant alleles. Therefore, the data suggests that the G3BP1 190-208 peptide may provide an efficacious means to treat patients suffering for protein aggregation related neurodegenerative disorders.

Figure 1B:
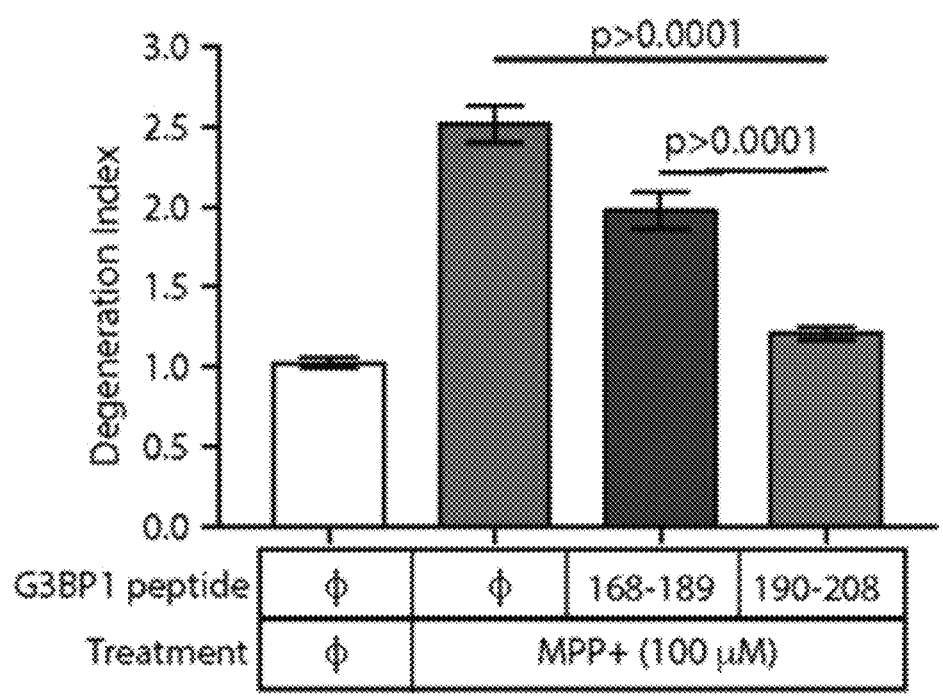
FIG. 1B shows quantification of neurite degeneration in midbrain neurons in control or 100 μM MPP+-treated neurons in the presence of 190-208 G3BP1 or control 168-189 peptides.

FIG. 1: Cell permeable G3BP1 190-208 peptide rescues MPP+-induced degeneration of midbrain neurons. (A) Representative images for NF-labeled (white) DIV7 E18 midbrain neurons. DIV7 midbrain cultures were treated with 10004 MPP+(ii) or control (i) and 10 µM 190-208 G3BP1 peptide (iv) or 168-189 control peptide (iii) [scale bar=100 µm]. (B) Quantification of neurite degeneration in midbrain neurons in control or 100 µM MPP+-treated neurons after addition of 190-208 G3BP1 or 168-189 control peptide. Results show that significant decrease in MPP+-induced degeneration for 190-208 peptide-treated cultures compared to 168-189 peptide exposure or MPP+-treated neurons. (N≥95 over 3 cultures; by one-way ANOVA with Tukey HSD post-hoc).

FIG. 2: Cell permeable G3BP1 190-208 peptide blocks pathological degeneration beta-amyloid-induced neurotoxicity in cortical neurons. (A) Representative images of NF-labeled (white) E18 cortical neurons. DIV7 cortical neurons were treated with 1 µM Aβpeptide (ii) or control (i) and 10 µM 190-208 G3BP1 peptide (iv) or 10 µM 168-189 control peptide (iii) [scale bar=100 µm]. (B) Quantitation of degeneration in cortical neurons treated with 1 µM Aβ peptide-treated neurons after addition of 190-208 G3BP1 or 168-189 control peptide. Solvent treated cells were used as control. A significant rescue from Aβ-induced neurite degeneration is observed in 190-208 peptide-treated neurons as compared to treatment with either 168-189 peptide or Aβ-treated controls. (N≥95 over 3 cultures; by one-way ANOVA with Tukey HSD post-hoc).

FIG. 3: Cell permeable G3BP1 190-208 peptide prevents mitotoxin-induced degeneration in motor neurons and axonal mRNA translation and causes disassembly of stress granules. (A) Quantification of mitotoxin/neurotoxin MPP+-induced degeneration of DIV7 E12.5 motor neuron neurites after exposure of cultures to 100 µM MPP+ and either 10 µM 190-208 G3BP1 or 168-189 control peptide. As controls, neurons treated with solvents were used. (B) Representative images of G3BP1 (green) and NF-labeled (red) E12.5 motor neurons under control or after treatment with 10004 MPP+ [scale bar=10 µm]. (C) distribution of sizes of endogenous G3BP1 aggregate per 100 µm neurite is shown as indicated bins from motor neurons cultures as treated in (B). (N≥80 neurites over three repetitions; by one-way ANOVA with Tukey HSD post-hoc). Results show a shift towards larger G3BP1 granule sizes in neurons treated with MPP+ as compared to controls. (D) Endogenous G3BP1 aggregate sizes per 100 µm neurite indicated as bins for motor neurons either untreated or treated with MPP+ alone or with addition of 10 µM 190-208 G3BP1 or 168-189 control peptide. Treatment with MPP+ results in formation of larger G3BP1 granules as compared to no treatment control. Addition of 190-208 G3BP1 peptide in the presence of MPP+ results in a decrease in the number of larger G3BP1 granules and reverses the G3BP1 granule distribution to those observed in the non-treated neurons. (N≥90 over 3 cultures; by one-way ANOVA with Tukey HSD post-hoc)

FIG. 4: Treatment of neurons with cell permeable G3BP1 190-208 peptide leads to disassembly of G3BP1 granules formed due to exposure of neurons to neurotoxins MPP+ and Aβpeptide. (A) Size of endogenous G3BP1 aggregates per 100 µm of neurite is shown as indicated bins from midbrain cultures under control conditions and after treatment with MPP+ alone or with 190-208 G3BP1 or 168-189 peptides. (B) Size distribution of endogenous G3BP1 aggregates per 100 µm of neurite is shown from cortical neurons treated with 104 Aβpeptide or with 10 µM 190-208 G3BP1 or 168-189 control peptide. Non-treated neurons were used as a control. The results show that treatment with 190-208 G3BP1 peptide leads to disassembly of G3BP1 granules. (N≥90 over 3 cultures; by two-way ANOVA with Tukey HSD post-hoc).

FIG. 5: Cell permeable G3BP1 190-208 peptide decreases TIA1-GFP puncta formed due to expression of disease causing TIA1 mutants. (A) Representative images of HEK cells transfected with GFP-tagged wild-type or ALS/FTD-associated mutants (P362L, A381T, or E384K) TIA1. Arrows show TIA1-GFP puncta. (B) Quantification of the percentage of cells with TIA1-GFP puncta greater than 2 µm$^2$ area in transfected cells relative TIA1-WT-GFP expressing cells. Consistent with previous studies, ALS/FTD-associated TIA1 mutants show increased number of TIA1-GFP puncta as compared to WT-TIA1. (C) HEK cells expressing TIA1-GFP or ALS/FTD-associated mutants TIA1-P362L, TIA1-A381T, TIA1-E384K were treated with sodium arsenite (0.5 mM) for 30 minutes followed by treatment with either 10☐M 190-208 G3BP1 or 168-189 control peptide. The number of cells containing TIA1-GFP puncta were measured and results are reported relative to non-treated controls. Number of HEK cells with TIA1-GFP granules both for WT and ALS/FTD mutants decreased after treatment with 10µM 190-208 G3BP1 as compared to the 168-189 control peptide treated cells. (N≥90 over 3 cultures; by two-way ANOVA with Tukey HSD post-hoc). Scale bar: 20 µm.

FIG. 6: Cell permeable G3BP1 190-208 peptide decreases granules formed by endogenous TIA1 and TDP43 and exogenous TDP43 and TIA1 mutants in motor neurons after sodium arsenite exposure. (A) Embryonic motor neurons isolated from E12.5 mouse embryos were exposed to sodium arsenite (0.5 mM) for 30 minutes and then treated with 10 µM 190-208 or 168-198 peptide. After fixation endogenous TIA1 was visualized by immunostaining. The number of TIA1 granules greater than 2 µm$^2$ per 100 µm of neurite were measured. (B) E12.5 motor neurons were treated as described in (A) and immunostaining was used to detect endogenous G3BP1 protein. The number of G3BP1 granules greater than 2 µm² per 100 µm of neurite were measured. The results show significantly decreased levels of TIA1 and G3BP1 granules in neurons treated with 190-208 treated neurons compared to 160-189 peptide treated neurons. (C) E12.5 motor neurons expressing TIA1-GFT or ALS/FTD-associated mutants TIA1-A381T, TIA1-E384K were treated with sodium arsenite (0.5 mM) for 30 minutes followed by treatment with either 10 µM 190-208 G3BP1 or 168489 control peptide. The number of cells containing TIA1-GFP puncta were measured. 2 µm² per 100 µm of neurite and results are reported relative to non-treated controls. The number of TIA1-AFP granules in neurites decreased for WT and ALS/ETD mutants after treatment with 1.90-208 G3BP1 as compared to the 168-189 control peptide treated cells. (D) E12.5 motor neurons expressing flag-tagged wildtype TDP43 or ALS-associated mutants TDP43-M337V and TDP43-Q331K were treated with sodium arsenite (0.5n ND for 30 minutes followed by treatment with either 10 µM 190-208 G3BP1 or 168-189 control peptide. Flag-TDP43 was detected by immunostaining using the anti-flag-antibody. The number of flag-TDP43 granules greater than 2 µm² were measured per 100 µm of neurite and the results are reported relative to non-treated controls. The number of Flag-TDP43 granules in neurites were decreased after treatment with 190-208 G3BP1 peptide as compared to the 168-189 control peptide in both WT and ALS/FTD mutants expressing cells. (N≥50 over 3 cultures; by two-way ANOVA with Tukey HSD post-hoc).

Critical functions of intra-axonally synthesized proteins are thought to depend on regulated recruitment of mRNA from storage depots in axons. Here the inventors show that axotomy of mammalian neurons induces translation of stored axonal mRNAs via regulation of the stress granule protein G3BP1, to support regeneration of peripheral nerves. G3BP1 aggregates within peripheral nerve axons in stress granule-like structures that decrease during regeneration, with a commensurate increase in phosphorylated G3BP1. Colocalization of G3BP1 with axonal mRNAs is also correlated with the growth state of the neuron. Disrupting G3BP functions by overexpressing a dominant-negative protein activates intra-axonal mRNA translation, increases axon growth in cultured neurons, disassembles axonal stress granule-like structures, and accelerates rat nerve regeneration in vivo.

Injured axons in the peripheral nervous system (PNS) use locally translated proteins for retrograde injury-signaling and regenerative growth. Translation of axonal mRNAs can be activated by different stimuli including axotomy in mature neurons and in response to guidance cues in developing neurons, indicating that a significant fraction of axonal mRNAs are stored until a particular stimulus activates their translation. Stress granules (SG) serve as storage depots for mRNAs in nonneuronal systems, providing a mechanism to respond to cellular stress by sequestering unneeded mRNAs from translation. Aggregation-prone mutations of the SG protein TIA1 and the RNA-binding protein TDP-43 have been shown to cause SG aggregation in neurons, but it is not known if SGs have roles in the normal function of neurons. Further, although SGs have been detected in dendrites, it is not clear if functional SGs are assembled in axons. The Ras GAP SH3 domain binding protein 1(G3BP1) interacts with the 48S pre-initiation complex when translation is stalled, and it assembles SGs by virtue of its NTF2-like domain. Murine G3BP1 knockout is embryonic lethal in 129/5v mouse strain with CNS apoptosis, but not a mixed Balb/c/129/Sv background where altered synaptic plasticity and neuronal calcium homeostasis were seen. This emphasizes roles for G3BP1 protein in the nervous system. Proteomics analyses recently reported G3BP1 interactomes from neurites of cultured motor neurons, where a core of SG-associated proteins was detected in the absence of stress. Thus, G3BP1 aggregates may have functions in axons.

Here the inventors show that translation of specific axonal mRNAs is negatively regulated in intact axons by G3BP1, and that this negative regulation is removed by dispersion of aggregated G3BP1 in regenerating peripheral nerves post injury to support accelerated axon growth. When phosphorylated on serine 149 ($G3BP1^{PS149}$), G3BP1's oligomerization is blocked and SGs disassemble, presumably releasing bound mRNAs for translation. Loss of G3BP1 aggregation in SG-like structures in regenerating axons is accompanied by an increase in phosphorylated G3BP1.

Disrupting G3BP1 function with a dominant-negative approach activates intra-axonal mRNA translation, increases axon growth in cultured neurons and accelerates nerve regeneration in vivo, and therefore represents a new pro-regenerative therapeutic approach.

Results

Figure 6A:
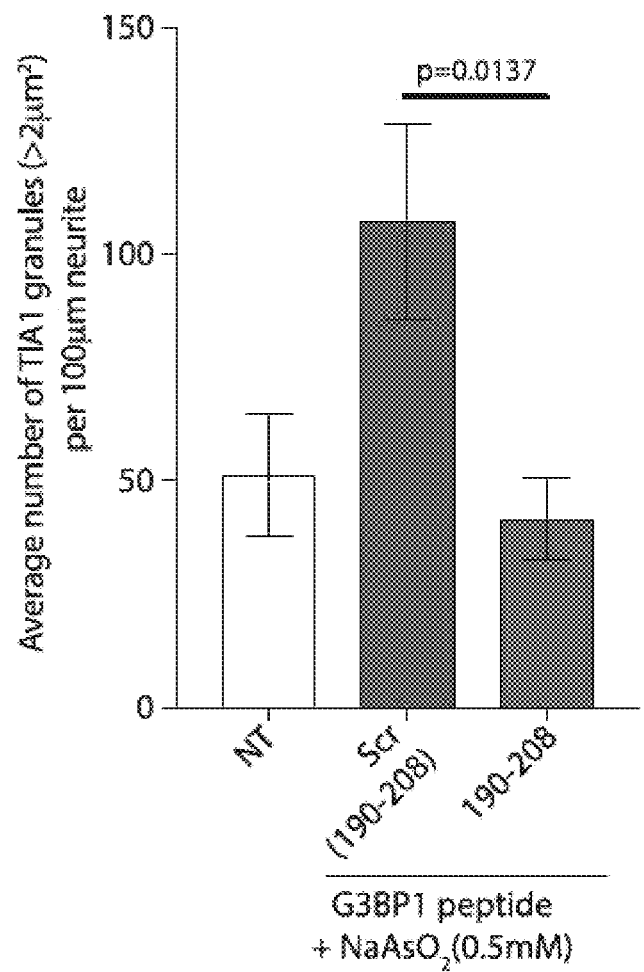
FIG. 6A shows embryonic motor neurons isolated from E12.5 mouse embryos exposed to sodium arsenite (0.5 mM) for 30 minutes and then treated with 10 μM 190-208 or 168-198 peptides at DIV7.
Figure 6B:
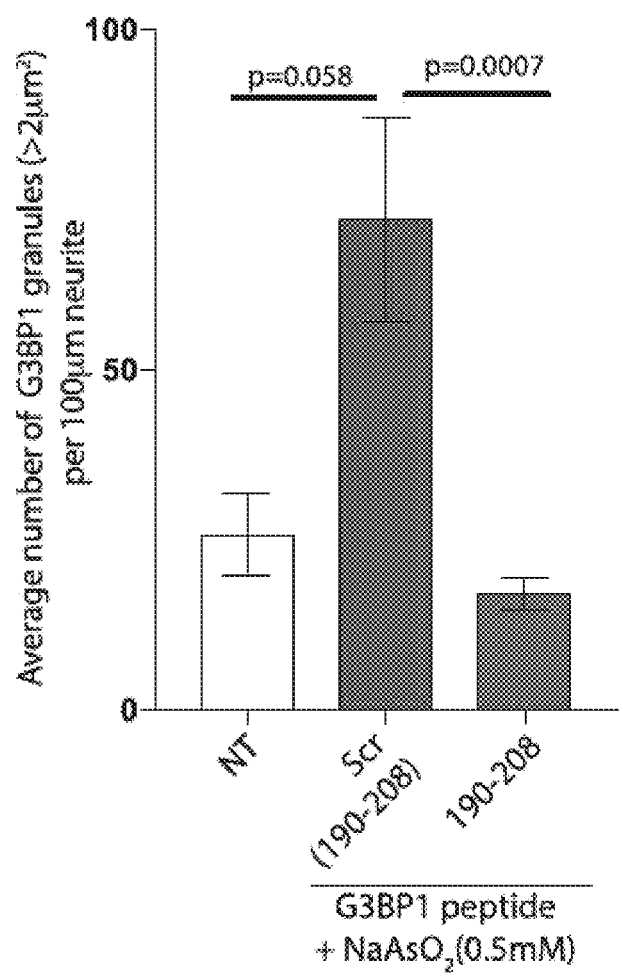
FIG. 6B shows E12.5 motor neurons treated as described in FIG. 5A and immunostaining used to detect endogenous G3BP1 protein.

Axonal G3BP1 aggregates decrease during nerve regeneration. The inventors initially asked if axons of cultured primary sensory neurons contain stress granule-associated protein G3BP1. Sensory neurons in dissociated cultures from adult rat dorsal root ganglia (DRG) show strong immunoreactivity for G3BP1 in cell bodies and focally along their axons (FIG. 6A). By confocal microscopy, axonal G3BP1 signals appeared to show higher colocalization with other SG components compared with components of processing bodies (PB) that are linked to RNA degradation (FIG. 6B).

Figure 6C:
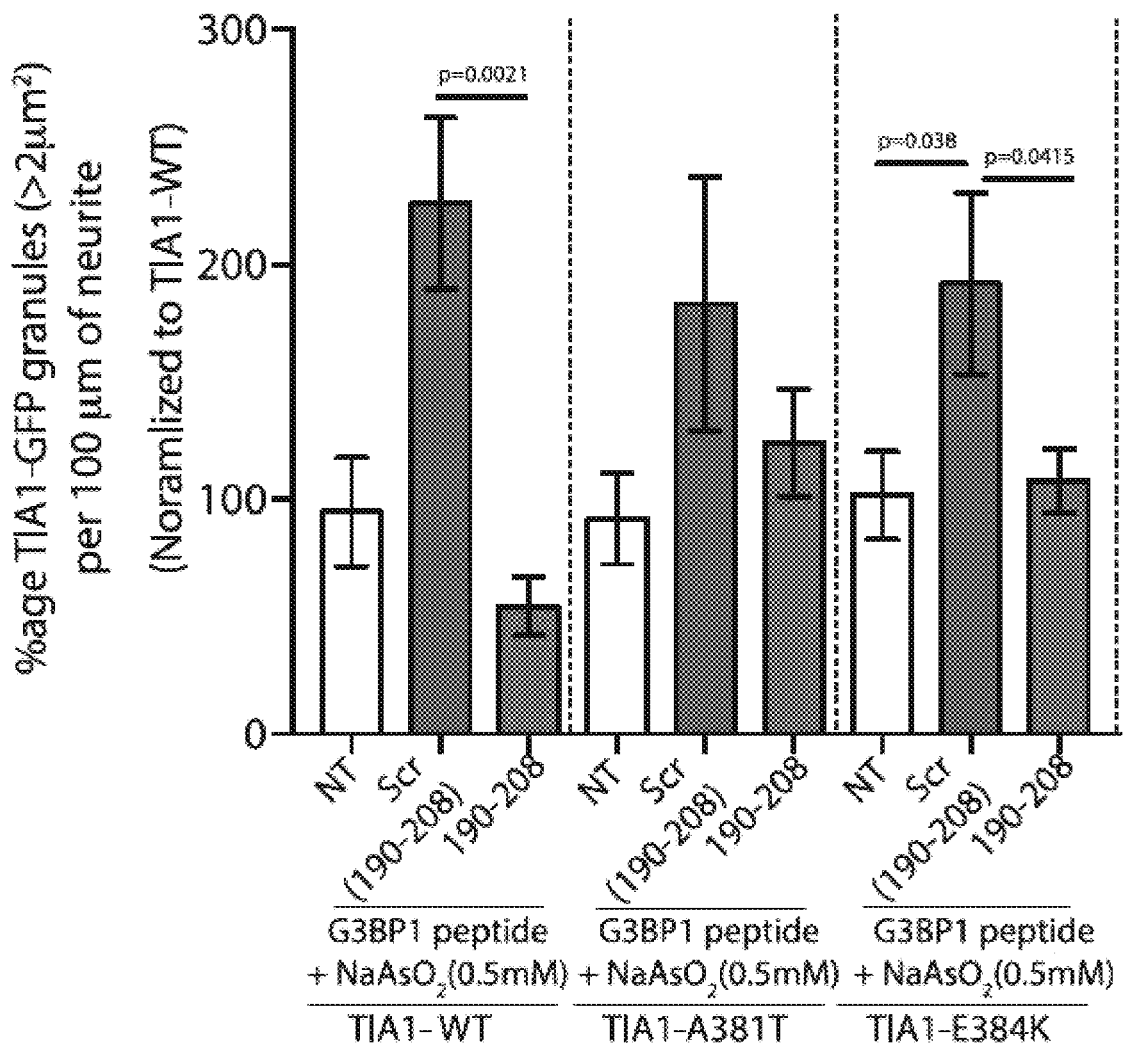
FIG. 6C shows DIV7 E12.5 motor neurons expressing TIA1-GFP or ALS/FTD-associated mutants TIA1-A381T, TIA1-E384K treated with sodium arsenite (0.5 mM) for 30 minutes followed.
Figure 6D:
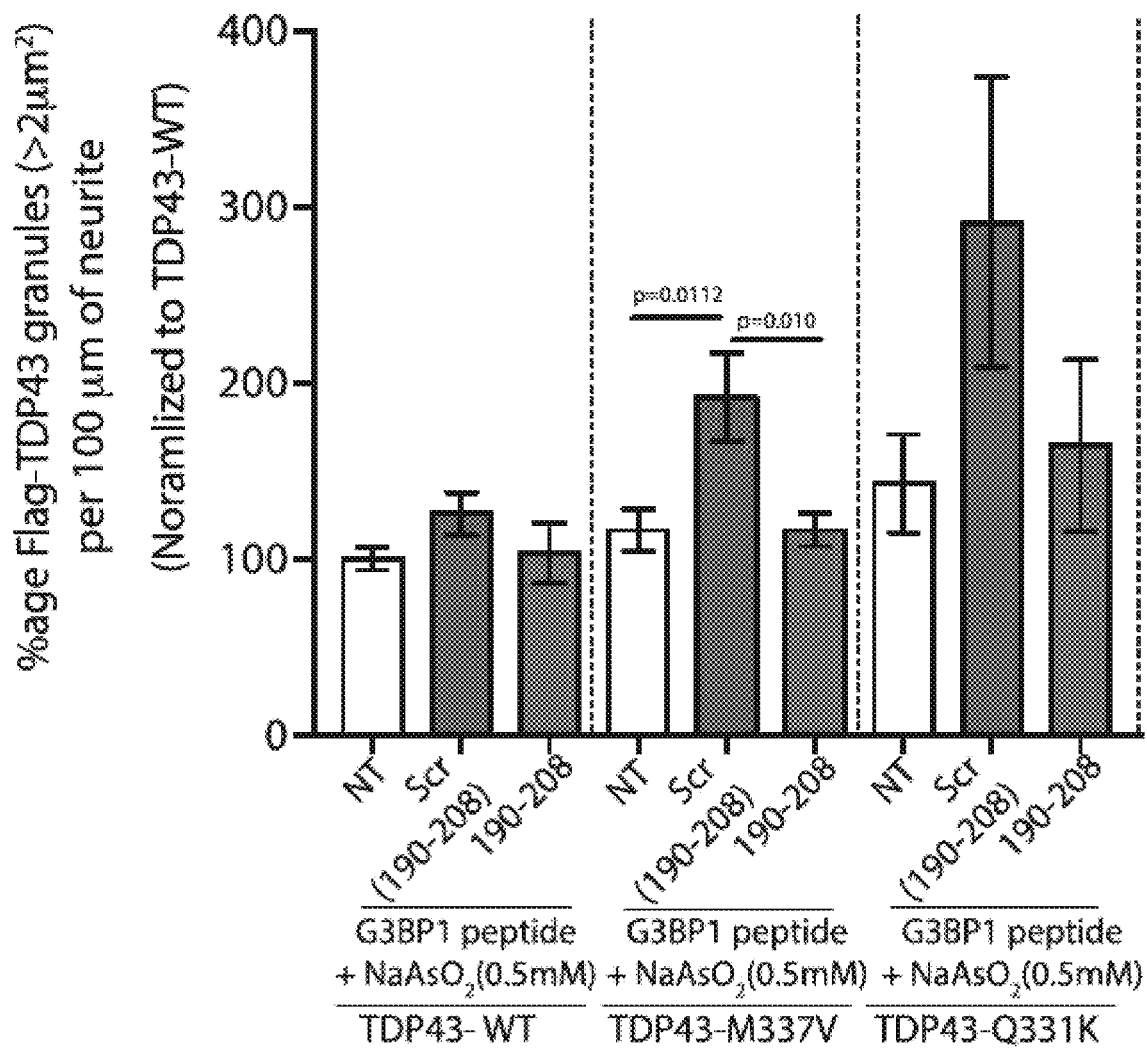
FIG. 6D shows DIV7 E12.5 motor neurons expressing flag-tagged wildtype TDP43 or ALS-associated mutants TDP43-M337V and TDP43-Q331K treated with sodium arsenite (0.5 mM) for 30 minutes followed by treatment with either 10 μM 190-208 G3BP1 or 168-189 control peptide.

Comparing Pearson's coefficients from these colabelings showed a significantly higher colocalization of axonal G3BP1 with SG markers than with PB markers (FIG. 6C). Colocalization of axonal G3BP1 with the SG protein HuR but not the PB protein DCP1a was further confirmed by proximity ligation assay (PLA; FIG. 6D). Overall, the axonal G3BP1 aggregates appeared smaller than those described for SGs in non-neuronal cells (diameter ~0.2-0.8 µm versus ≥1 µm for stress-induced aggregates), so the axonal SG-like entities approximate the ~250 nm diameter described for SG core structure.

Confocal microscopy of sciatic nerve sections showed robust, granular G3BP1 signals that overlapped with neurofilament (NF) across optical planes of the Z stacks (FIG. 6E). Signals for the SG protein TIA1 focally overlapped with G3BP1, including the granular intra-axonal G3BP1 signals, and the axonal signals for both G3BP1 and TIA1 appeared to decrease in 7 d post-crush sciatic nerve just proximal to the crush site (FIG. 6E). The imaging parameters for these analyses were selected to visualize only the granular G3BP1 signals; on highly over-exposing the granular G3BP1 signals, more diffuse signals were noted for G3BP1 along the axon (data not shown), suggesting that the granular signals represent aggregates of G3BP1 in axons. The inventors quantified the granular signals for G3BP1 and TIA1 in axons proximal to crush site at intervals over 3 h to 7 d after axotomy. Both proteins showed a striking increase in the intra-axonal signals at 3 h postcrush which fell to below the levels of the naive axons by 5 d postcrush; notably, the fold change for G3BP1 and TIA1 near perfectly overlapped across this time course (FIG. 6F). Axons are actively regenerating at 7 d after nerve crush (see below), and granular G3BP1 signals were largely excluded from the thin axons at the regenerating front of the injured nerve.

Immunoblotting of DRG neurons transfected with control versus G3BP1 targeting siRNAs confirmed the specificity of the anti-G3BP1 antibody used here. To gain a more quantitative assessment of G3BP1 protein levels in axons, the inventors used targeted mass spectrometry (MS) of sciatic nerve axoplasm taken over 3-28 d post injury. The MS analyses further confirmed presence of G3BP1 in axons and showed modest, but highly variable, declines in G3BP1 levels after an injury. Approximately 3 cm of nerve proximal to the crush site was used for axoplasm preparations in these MS studies. Immunoblotting axoplasm from shorter segments of injured sciatic nerve (0 to _1 cm and _1 to _2 cm proximal to the crush site) showed a clear reduction in G3BP1 signals in 7 d injured compared to naive sciatic nerves.

Taken together, these data indicate that axonal SG-like structures and G3BP1 protein levels change after axonal injury and subsequent regeneration of PNS nerves. Thus, the inventors wondered if the decrease in axonal SG-like aggregation might be a feature of growing axons. So the inventors asked if axonal SG-like structures show alterations in vitro in DRG neurons with different axon growth capacity. DRG neurons that are conditioned by an in vivo crush injury 7 d prior to culture show more rapid axonal outgrowth over 18-48 h in vitro compared to uninjured (naive) DRGs13, and the rapidly growing axons of those injury-conditioned neurons showed a decrease in G3BP1 aggregates compared to those of naive DRG cultures (FIGS. 6G and 6I1). Together, these data raise the possibility that aggregation of axonal G3BP1 in PNS axons is associated with a lower axon growth activity.

Figure 7A:
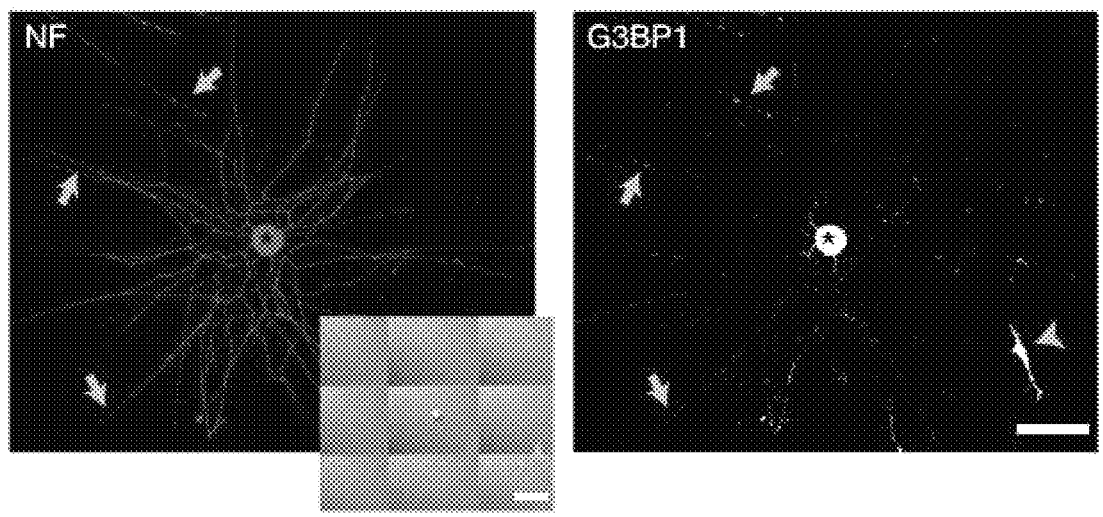
FIG. 7A shows immunofluorescence for G3BP1 signals in the cell body (asterisk) and axons (arrows) of a cultured DRG neuron.
Figure 7B:
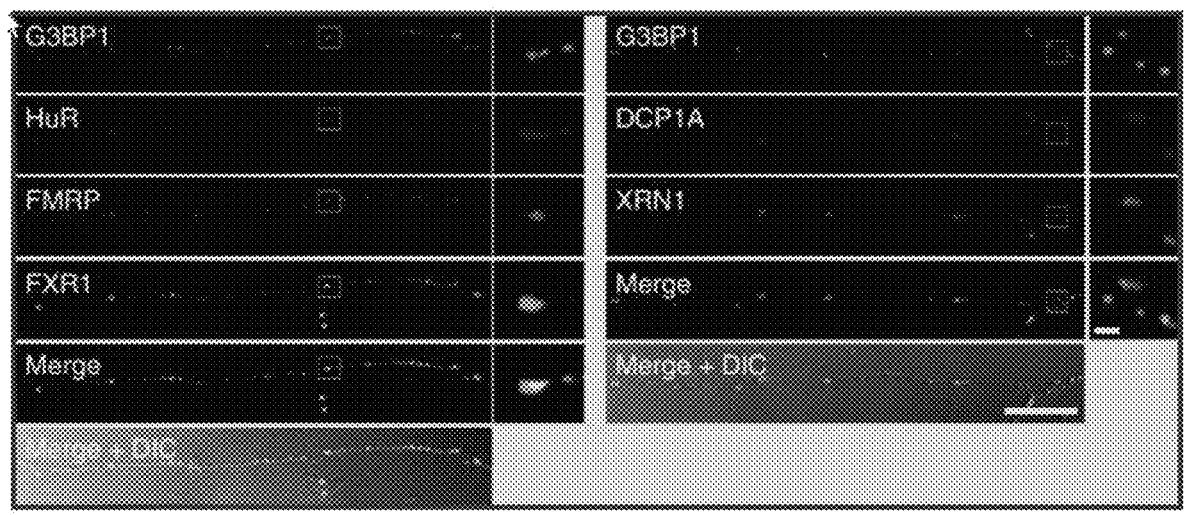
FIG. 7B shows single optical planes for axons of naive DRG cultures co-labeled for indicated proteins.
Figure 7C:
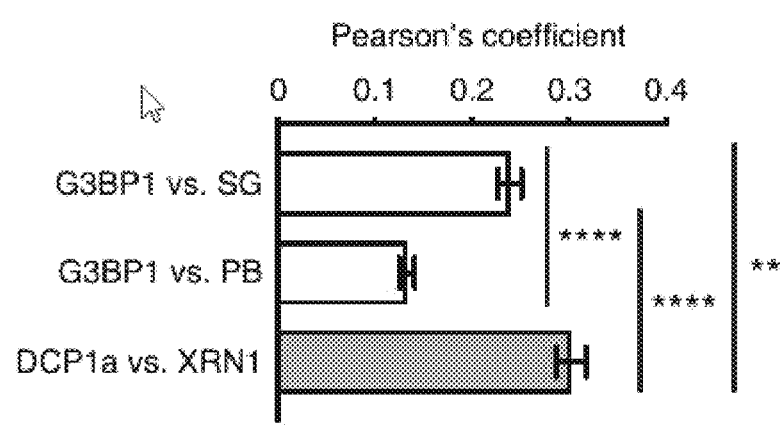
FIG. 7C shows axonal G3BP1 higher colocalization coefficients for SG than PB proteins by Fisher's Z transformation

G3BP1 is phosphorylated in regenerating axons. Phosphorylation of G3BP1 on Serine 149 has been shown to trigger disassembly of SGs. To determine if phosphorylation alters aggregation of axonal G3BP1, the inventors expressed nonphosphorylatable and phosphomimetic G3BP1 mutants (G3BP1$^{S149A}$-GFP and G3BP1$^{S149E}$-GFP, respectively) in cultured DRGs. Axonal G3BP1$^{S149A}$-GFP showed aggregated signals that overlapped with the SG-associated protein HuR, while axonal G3BP1$^{S149E}$-GFP appeared diffuse (FIGS. 7A and 7B). G3BP1$^{S149E}$-GFP also showed significantly higher mobility in axons than G3BP1$^{S149A}$-GFP, and G3BP1-GFP showed mobility intermediate between G3BP1$^{S149E}$-GFP and G3BP1$^{S149A}$-GFP (FIG. 7C). This is consistent with G3BP1$^{S149A}$-GFP aggregating into SG-like structures in axons.

The inventors next asked whether endogenous G3BP1 is phosphorylated in axons using phospho-specific G3BP1$^{PS149}$ antibodies.

FIGS. 6A-6H show G3BP1 localizes to axons in stress granule-like aggregates. Immunofluorescence for G3BP1 shows signals in the cell body (asterisk) and axons (arrows) of a cultured DRG neuron; arrowheads indicate Schwann cell with prominent G3BP1 immunoreactivity visible in the inset DIC image. Previous work has shown that neurites of these adult DRG neurons have axonal features and lack dendritic features; the inventors will use 'axon' for describing these hereafter [scale bar=50 µm]. b, c Single planes for axons of naive DRG cultures co-labeled for indicated proteins are shown; box represents the area for high magnification insets to right (b). Axonal G3BP1 shows higher colocalization coefficients for SG than PB proteins by Fisher's Z transformation (c; N≥30 axons over 3 repetitions; p≤0.01, **p≤0.001 by one-way ANOVA with Tukey HSD post-hoc) [scale bar=10 µm for large panels, 1 µm for insets]. d PLA shows higher colocalization for G3BP1 and HuR than G3BP1 and DCP1A (G3BP1+HuR PLA=0.038±0.003 and G3BP1+DCP1A PLA=0.027±0.002 signals/µm; N≥40 neurons over 6 repetitions, p=0.016 by Student's t-test) [scale bar=20 µm]. e, f Confocal images for G3BP1 and TIA1 in naive and 7 d post-injured ('regenerating') sciatic nerve are shown (e). Upper image panels of each pair show G3BP1 and TIA1 merged with NF signals in single plane. Lower panels of each pair show XYZ for G3BP1 and TIA1 signals that overlap with NF across the Z stack Quantitation of axonal G3BP1 and TIA1 signals are shown (f) as mean±SEM (N=6 animals; *p≤0.05, *p≤0.001 for G3BP1 and p≤0.01, p≤0.0001 for TIA1 by Student's t-test for versus naive) [scale bar=5 µm]. g, h Quantification of G3BP1 levels (g) and G3BP1 immunofluorescence (h) in axons of DRGs cultured from naive versus 7 d injury-conditioned animals are shown (mean±SEM for N≥66 neurons over 3 repetitions; *p≤0.001 by Student's t-test) [scale bar 20 µm]

Figure 7D:
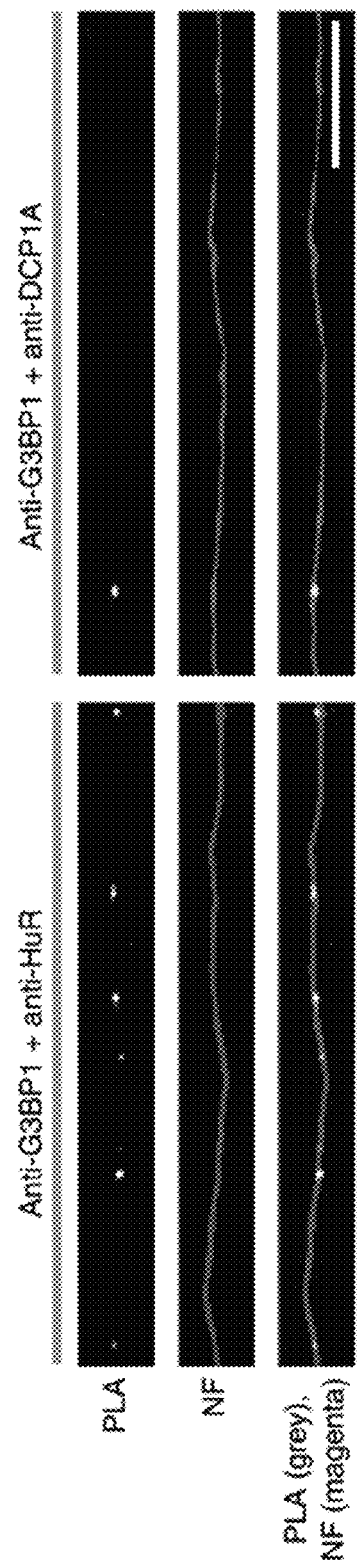
FIG. 7D shows that proximity ligation analyses (PLA) shows higher colocalization for G3BP1 and HuR than G3BP1 and DCP1A (G3BP1+HuR PLA=0.038±0.003 and G3BP1+DCP1A PLA=0.027±0.002 signals/m².
Figure 7E:
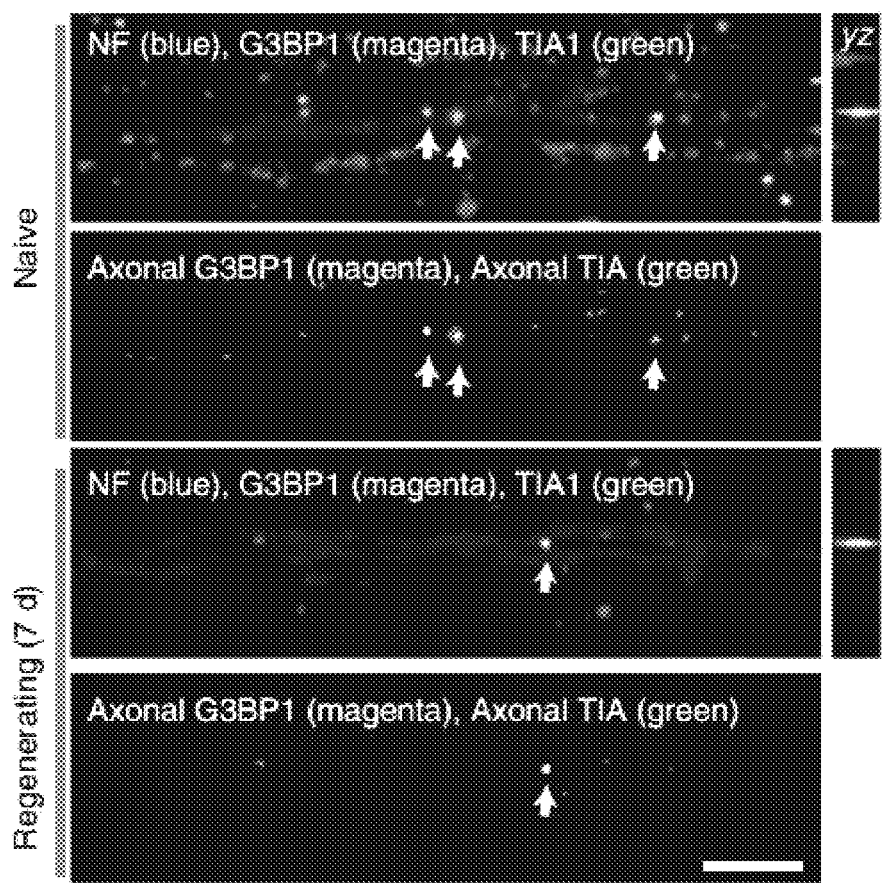
FIG. 7E shows confocal images for G3BP1 and TIA1 in naive and 7 d post-injured ('regenerating') sciatic nerve.
Figure 7F:
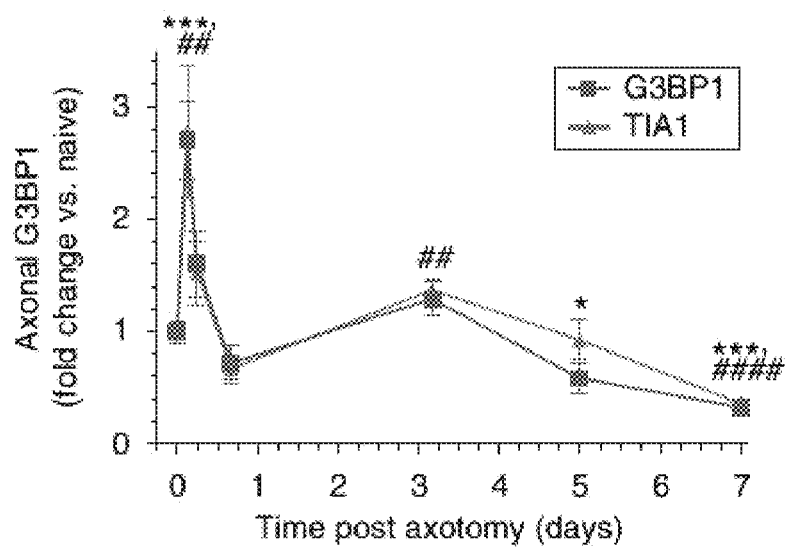
FIG. 7F shows upper image panels of each pair that show G3BP1 and TIA1 merged with NF signals in a single plane.
Figure 7G:
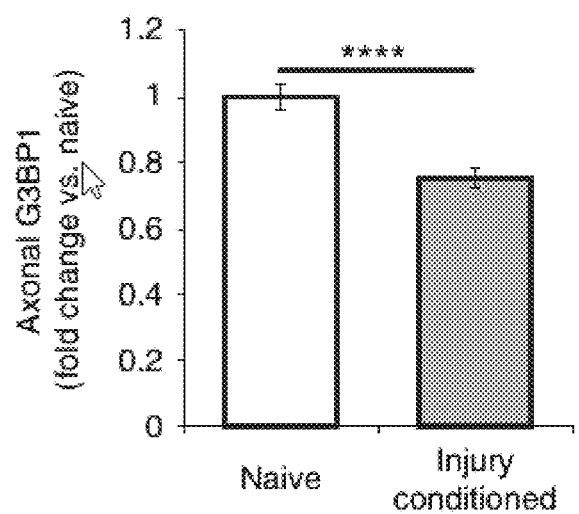
FIG. 7G shows quantification of G3BP1 levels in axons of DRGs cultured from naive versus 7 d injury-conditioned animals
Figure 7H:
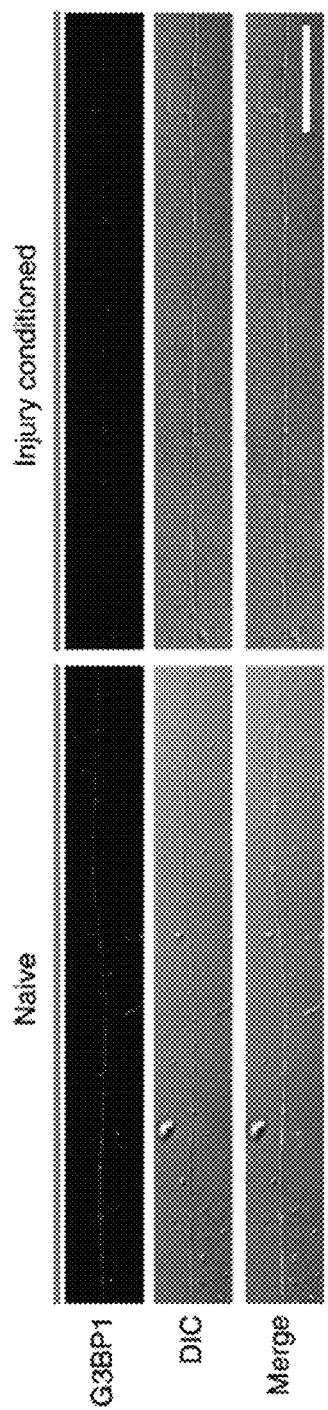
FIG. 7H shows G3BP1 immunofluorescence in axons of DRGs cultured from naive versus 7 d injury-conditioned animals.

Immunoblotting with lysates from control versus G3BP1 siRNA transfected DRGs showed a single band for anti-G3BP1$^{PS149}$. Treating DRG cultures with arsenic, a known inducer of SG aggregation, also decreased levels of G3BP1$^{PS149}$ without affecting overall G3BP1 levels by immunoblotting (data not shown). By immunofluorescence, intra-axonal signals for anti-G3BP1$^{PS149}$ increased in proximal sciatic nerves 7 d post-crush injury (FIGS. 7D and 7E). Thus, as the prevalence of axonal SG like structures decreased in regenerating axons, there was a corresponding increase in axonal G3BP1P$^{S149}$. Moreover, in cultured DRG neurons, the ratio of axonal G3BP1$^{PS149}$ to axonal G3BP1 aggregates increases in distal axons and growth cones (FIGS. 7F and 7G), suggesting that the axonal G3BP1 aggregation and phosphorylation are dynamically regulated along the growing axon.

Figure 8A:
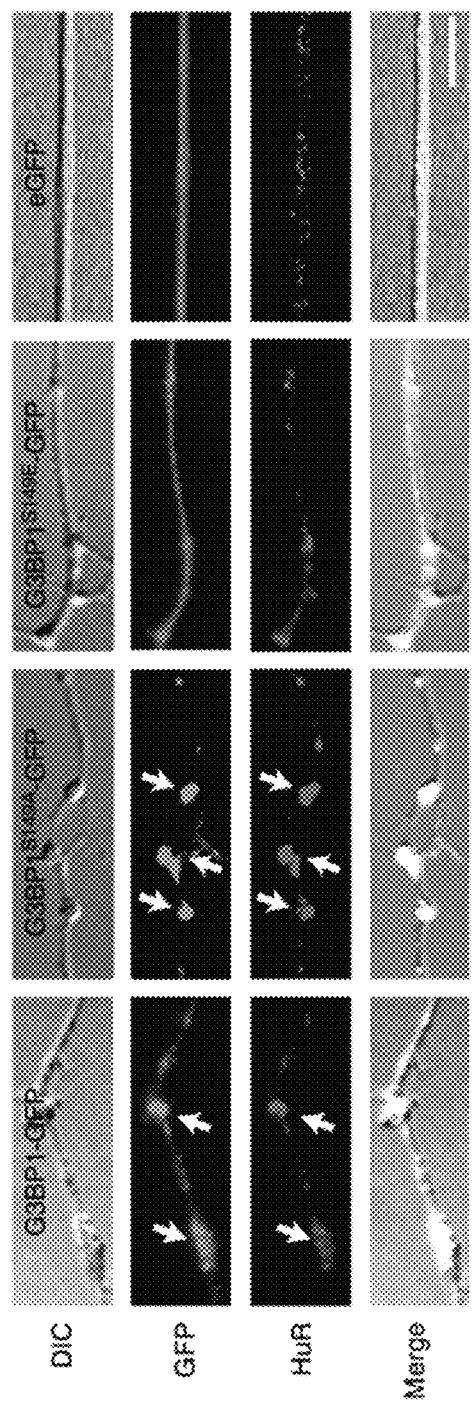
FIG. 8A shows representative images for axons of DRG neurons transfected with indicated G3BP1 constructs versus eGFP.
Figure 8B:
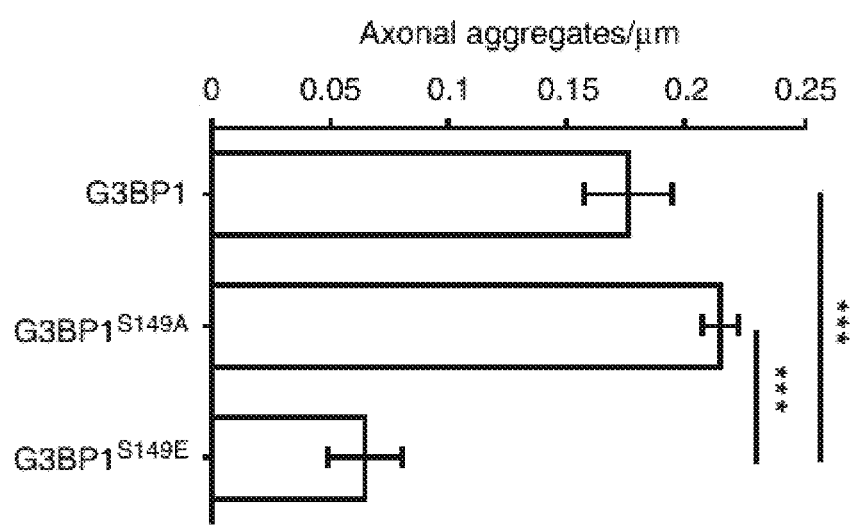
FIG. 8B shows quantification of axonal aggregates for G3BP1-GFP, G3BP1$^{S149A}$-GFP, and G3BP1$^{S149E}$-GFP.

Axonal G3BP1 modulates axonal mRNA translation. Previous studies detected ribosomes and translation factors in regenerating PNS axons in vivo, so the decrease in SG-like structures in distal axons could reflect increased protein synthesis in those axons. Thus, the inventors asked if axonal mRNAs colocalize with G3BP1 in cultured neurons. Endogenous Neuritin1 (Nrn1) and Importin 81 (Imp81) mRNAs showed clear colocalization with axonal G3BP1, but the mRNA encoding Growth-associated protein 43 (Gap43) did not (FIG. 8A). The more rapidly growing axons of injury-conditioned DRG neurons showed higher colocalization of Imp81 with G3BP1 than those of naive DRGs, while axonal Nrn1 showed the opposite (FIG. 8B). Axonal Gap43 showed overall lower G3BP1 colocalization coefficients that did not change with injury conditioning (FIG. 8B). IMP81 protein is used for injury response after axotomy and negatively regulates axon growth under basal conditions, while NRN1 protein supports regenerative growth of axons. Thus, these distinct colocalizations of axonal Imp81 and Nrn1 mRNAs with G3BP1 protein in naive versus injury-conditioned neurons may reflect different functions of the encoded proteins in these different growth states.

Figure 8C:
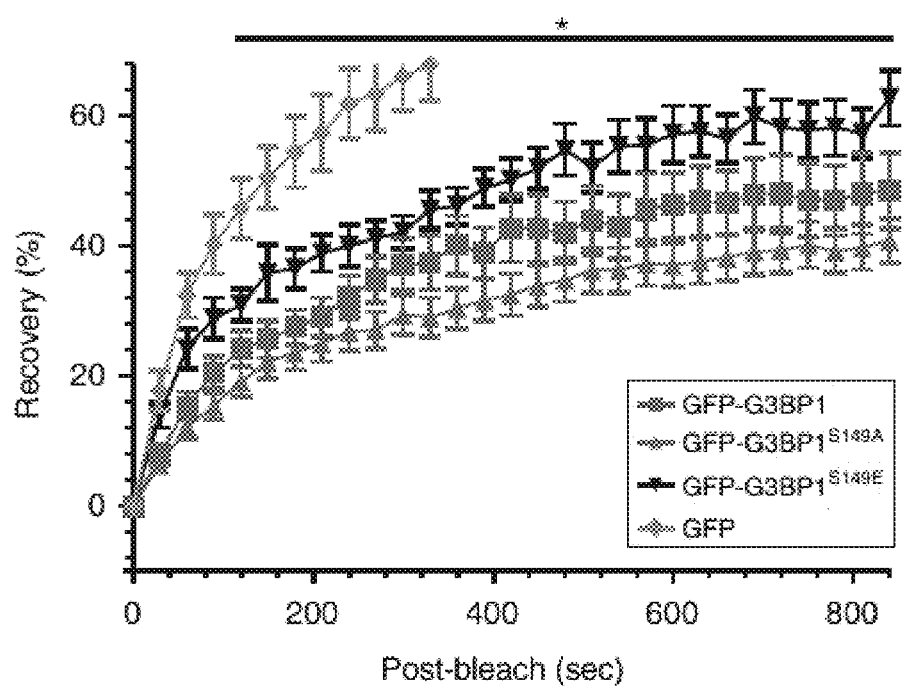
FIG. 8C shows FRAP analyses for neurons transfected with constructs as in FIG. 8A are shown as average normalized % recovery±standard error of the mean (SEM).
Figure 8D:
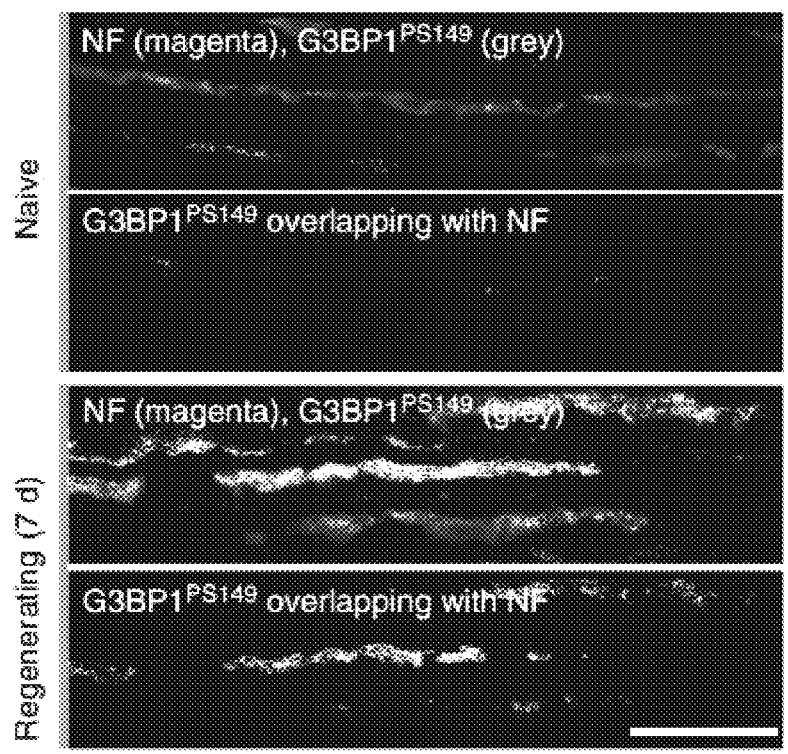
FIG. 8D shows exposure-matched confocal images for G3BP1$^{PS149}$ and NF.
Figure 8E:
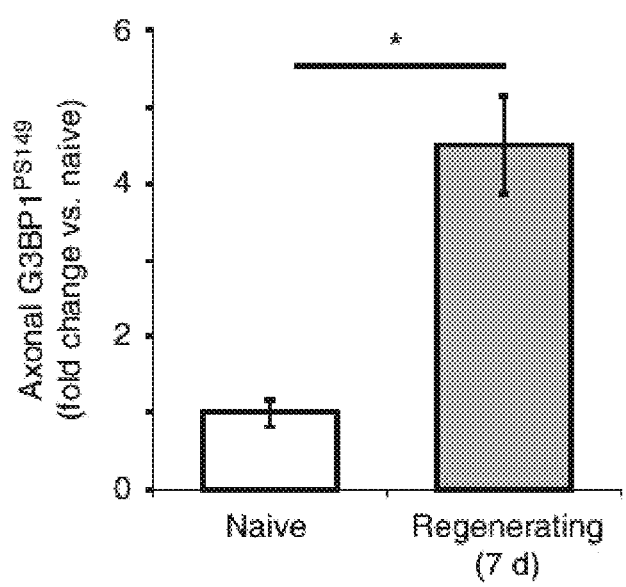
FIG. 8E shows quantifications of the signals shown in FIG. 7D as mean±SEM.
Figure 8F:
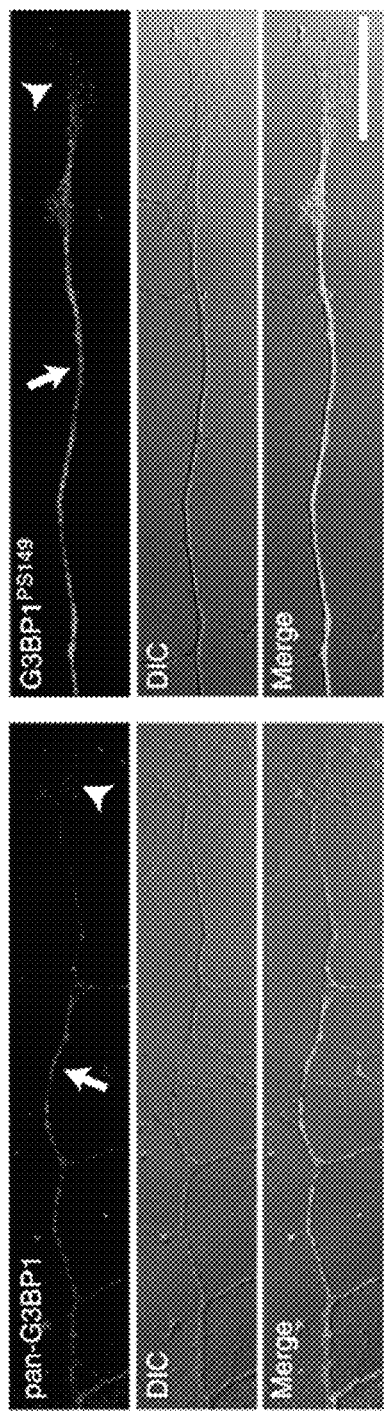
FIG. 8F shows distal axons of cultured DRGs immunostained with pan-G3BP1 versus G3BP1$^{PS149}$ antibodies.
Figure 8G:
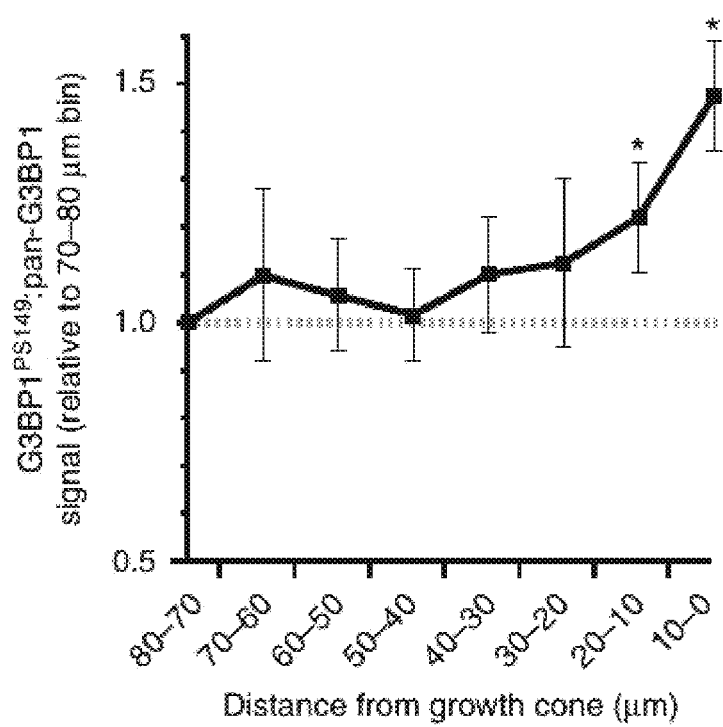
FIG. 8G shows quantification of the signals from FIG. 7F with a significant increase in the ratio of G3BP1$^{PS149}$ immunoreactivity to G3BP1 aggregates moving distally to the growth cone.

The inventors next used fluorescent reporters to determine if axonal SG like structures contribute to translation. For this, the inventors generated axonally targeted GFP$^{MYR}$ and mCherry$^{MYR}$ containing the 5' and 3' untranslated regions (UTR) of Impβ1, Nrn1, and Gap43 mRNAs (GFP$^{MYR}$ 5'/3'impβ1, GFPM$^{YR}$ 5'/3'nrn1, and mCh$^{MYR}$ 5'/3'gap43, respectively; FIG. 8C). The membrane localizing myristoylation (MYR) of the fluorescent reporter proteins dramatically limits their diffusion from sites of translation, so GFP$^{MYR}$ and mCherry$^{MYR}$ proteins provide versatile reporters for localized protein synthesis in dendrites and axons using fluorescence recovery after photobleaching (FRAP). The 3' (Impβ1 and Gap43) and 5' (Nrn1) UTRs provide axonal targeting for reporter mRNAs, and with both 5' and 3'UTRs, the reporters approximate the translational regulation of the endogenous mRNAs. Recovery of axonal GFP$^{MYR}$ 5'/3'nrn1 and GFP$^{MYR}$ 5'/3'impβ1 fluorescence was decreased in DRGs expressing G3BP1-BFP compared to the BFP control, but mCh$^{MYR}$ 5'/3'gap43 recovery was not significantly affected by G3BP1-BFP expression (FIGS. 8D-8G). Treatment with translation inhibitors confirmed that the fluorescence recovery in axons after photo bleaching represents new protein synthesis, and, interestingly, overexpression of G3BP1-BFP approximated the effect of protein synthesis inhibition for GFP$^{MYR}$ 5'/3'nrn1 and GFP$^{MYR}$ 5'/3'impβ1 fluorescence recovery (FIGS. 8E-8G). Additionally, RNA immunoprecipitation (RIP) analyses showed enrichment of GFP$^{MYR}$ 5'/3'impβ1 and GFP$^{MYR}$ 5'/3'nrn1, but not mCh$^{MYR}$ 5'/3'gap43, in G3BP1 immunoprecipitates (FIG. 8II). Taken together, these data suggest that G3BP1 binds to Nrn1 and Impβ1 mRNAs and attenuates their translation in axons.

FIGS. 7A-7G show G3BP1 is phosphorylated in regenerating axons. a Representative images for axons of DRG neurons transfected with indicated G3BP1 constructs versus eGFP are shown. G3BP1-GFP and G3BP1$^{S149A}$-GFP show prominent aggregates in axons that colocalize with HuR (arrows). In contrast, axonal signals for G3BP1$^{S149E}$-GFP and eGFP appear diffuse [scale bar=5 μm]. b Quantification of axonal aggregates for G3BP1-GFP, G3BP1$^{S149A}$-GFP, and G3BP1$^{S149E}$-GFP is shown as average±SEM (N≥10 neurons over 3 repetitions; ***p≤0.005 by one-way ANOVA with Tukey HSD post-hoc). c FRAP analyses for neurons transfected with constructs as in A are shown as average normalized % recovery±SEM. G3BP1$^{S149A}$-GFP shows much lower recovery than G3BP1$^{S149E}$-GFP; G3BP1-GFP is intermediate between G3BP1$^{S149A}$-GFP and G3BP1$^{S149E}$-GFP (N≥13 axons over 3 repetitions; *p≤0.05 between G3BP1$^{S149A}$-GFP versus G3BP$^{S6146E}$-GFP by one-way ANOVA with Tukey HSD post-hoc). Only the 0-320s. recovery signals for GFP are shown (at 840 s. GFP showed 85.5±4.7% recovery with p≤0.0001 versus G3Bp1$^{S149E}$-GFP by one-way ANOVA with Tukey HSD post-hoc). d-e Exposure-matched confocal images for G3BP1$^{PS149}$ and NF are shown for sciatic nerve (d) as in FIG. 6E. There is a striking increase in G3BP1$^{PS149}$ immunoreactivity in the regenerating axons. Quantifications of these signals are shown as mean±SEM (e; N=3; *p≤0.05 by one-way ANOVA with Tukey HSD post-hoc) [scale bar=20 μm]. f-g Distal axons of cultured DRGs immunostained with pan-G3BP1 versus G3BP1$^{PS149}$ antibodies are shown as indicated (f). Aggregates of G3BP1 are visible in the axon shaft (arrow), but decrease moving distally towards the growth cone (arrowhead).

G3BP1$^{PS149}$ signals are fairly consistent and extend into the growth cone (arrowhead). Quantification of signals (g) shows significant increase in ratio of G3BP1$^{PS149}$ immunoreactivity to G3BP1 aggregates moving distally to the growth cone (N≥9 neurons each over 3 repetitions; *p≤0.05 versus 70-80 μm bin by one-way ANOVA with Tukey HSD post-hoc) [scale bar=20 μm]

FIGS. 8A-8H show 3 G3BP1 regulates translation of axonal mRNAs. a Images of FISH/IF for Nrn1 mRNA and G3BP1 protein are shown for axons of naive and 7 d injury conditioned DRG neurons. Colocalization panel (Coloc) represents the mRNA:G3BP1 colocalization in a single optical plane [scale bar=5 μm]. b Quantification of colocalizations for Nrn1, Impβ1, and Gap43 mRNAs with G3BP1 in axons of neurons cultured from naive or 7 d injury-conditioned animals shown as average Pearson's coefficient±SEM (N≥21 neurons over 3 repetitions; p≤0.01 and *p≤0.005 by one-way ANOVA with Tukey HSD post-hoc). c Schematics of translation reporter constructs used in panels d-h. d Representative FRAP image sequences for DRG neurons co-transfected with GFP$^{MYR}$ 5'/3'nrn1 plus BFP or G3BP1-BFP. Boxed regions represent the photobleached ROIs. e-g Quantifications of FRAP assays from DRGs expressing GFP$^{MYR}$ 5'/3'nrn1 (e) or GFP$^{MYR}$ 5'/3'impβ1 (f) or mCh$^{MYR}$ 5'/3'gap43 translation reporters along with G3BP1-BFP or control BFP are shown as normalized, average % recovery±SEM (N≥11 neurons over 3 repetitions; *p≤0.05, and **p≤0.01 for BFP versus G3BP1-BFP, p≤0.05, p≤0.01, and p≤0.0001 for BFP versus translation inhibitors by one-way ANOVA with Tukey HSD post-hoc).

Figure 9A:
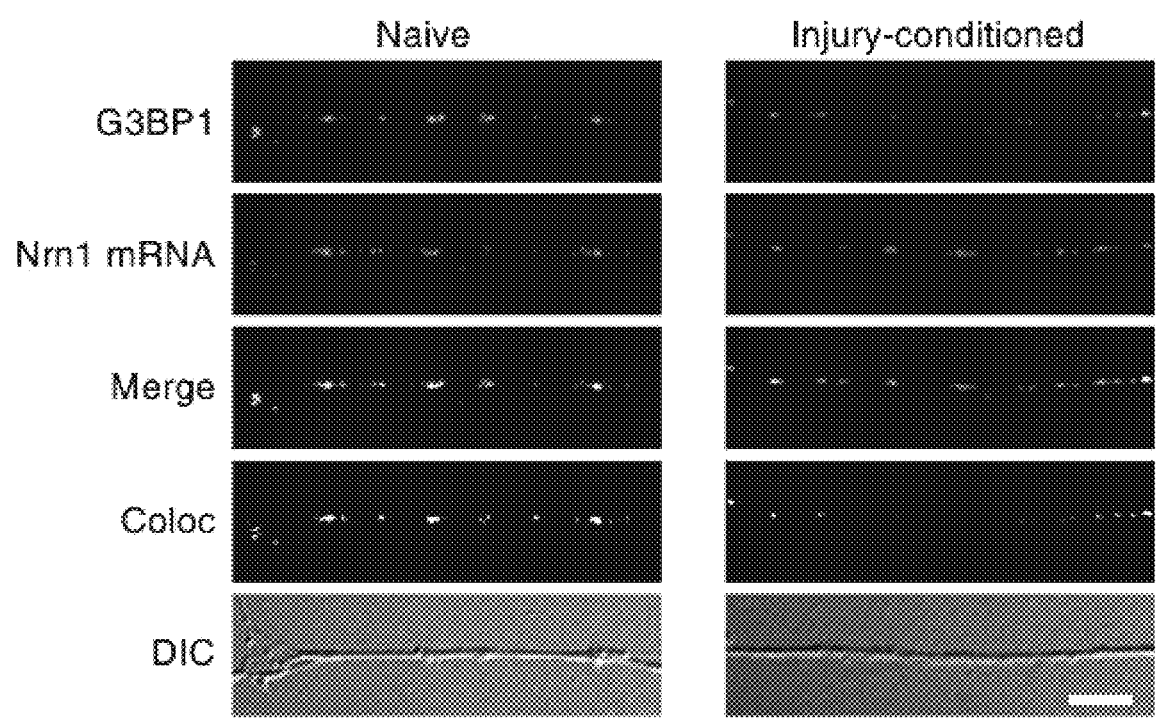
FIG. 9A shows images of FISH/IF for Nrn1 mRNA and G3BP1 protein shown for axons of naive and 7 d injury conditioned DRG neurons.

HEK293T cells transfected with GFP$^{MYR}$ 5'/3'nrn1, GFP$^{MYR}$ 5'/3' impβ1, and mCh$^{MYR}$ 5'/3'gap43 show significant enrichment of GFP$^{MYR}$ 5'/3'nrn1 and GFP$^{MYR}$ 5'/3' impβ1 mRNAs coimmunoprecipitating with G3BP1 versus control (N=4 culture preparations; *p≤0.05 by Student's t-test). Western blot validating G3BP1 immunoprecipitation shown as inset. Values shown as average percent bound mRNA relative to input±SEM. The acidic domain of G3BP1 increases axonal growth. Four domains have been defined for G3BP1 protein: an N-terminal NTF2-like 'A domain', a highly acidic 'B domain', a PxxP motif containing 'C domain', and a C-terminal RNA-binding motif containing 'D domain' (FIG. 9A).

Figure 9B:
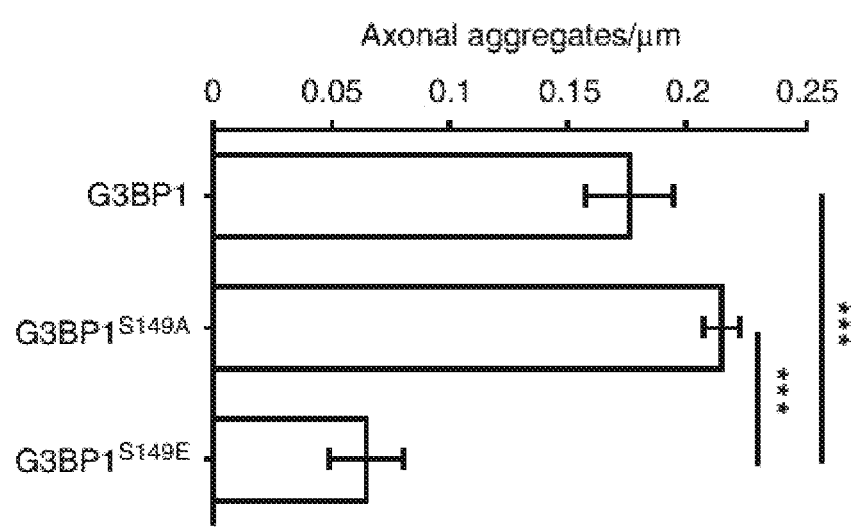
FIG. 9B shows quantification of colocalizations for Nrn1, Impβ1, and Gap 43 mRNAs with G3BP1 in axons of neurons cultured from naive or 7 d injury-conditioned animals shown as average Pearson's coefficient±SEM (N≥21 neurons over 3 repetitions.

The inventors acquired expression constructs for the B, C, and D domains and combinations of these to determine if they might affect the function of endogenous G3BP1 in the DRG neurons. Expression of these G3BP1 deletion constructs in naive DRG cultures showed that G3BP1 B, CD, BCD, and D domain proteins all localized to axons. Neurons expressing the G3BP1 B domain showed significantly longer axons, while those expressing the D or CD domains showed shorter axons (FIG. 9B).

The G3BP1 D domain was previously shown to reduce protein synthesis in non-neuronal cells by triggering phosphorylation of the translation initiation factor eIF2α. Interestingly, a combined construct of the B domain with the CD domain significantly increased axon outgrowth, pointing to a dominant-negative effect of the B domain in absence of G3BP1's aggregating NTF-2 like region. Though the G3BP1 B domain contains Ser 149 whose phosphorylation causes SG disassembly, neither G3BP1$^{S149E}$-GFP nor G3BP1$^{S149A}$-GFP altered axon growth in the DRGs compared to GFP. DRGs expressing the B domain- and CD domain-GFP showed modest decline in neurites per neuron, as did the expression of full-length G3BP1-GFP. However, overexpression of full length G3BP1 had no significant effect on axon growth, perhaps indicating that G3BP1 is at saturating levels in DRG neurons. Consistent with this, siRNA-mediated G3BP1 depletion significantly increased axon growth and this was completely reversed by co-transfection with a siRNA-resistant G3BP1-GFP. Co-transfecting with the G3BP1 B domain did not further increase axon length in the G3BP1 depleted neurons, suggesting that the B domain inhibits function of endogenous G3BP1.

Figure 9C:
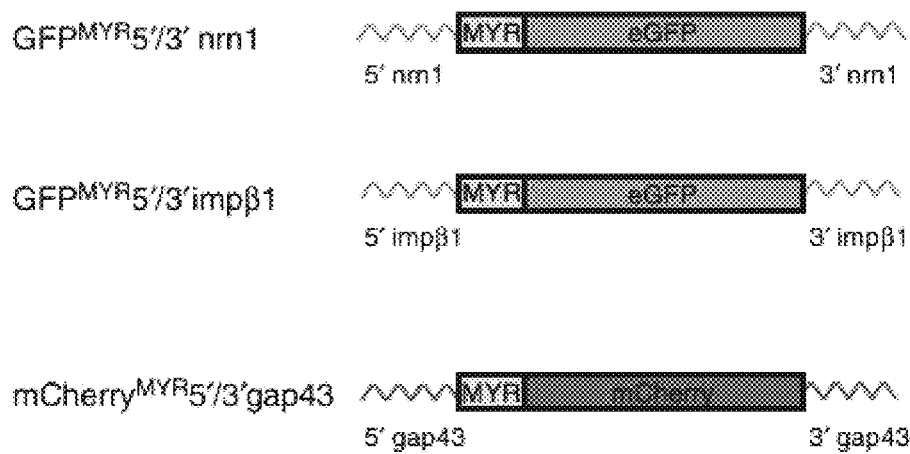
FIG. 9C shows schematics of translation reporter constructs used in FIGS. 9D-H.

In light of the axon growth-promoting effect of the G3BP1 B domain, the inventors asked if introducing the G3BP1 B domain might alter axon regeneration in vivo. For this, adult rats were transduced with adeno-associated virus (AAV) expressing B domain, D domain, or full length G3BP1 and then subjected to sciatic nerve crush 7 d later. At 7 d after crush injury (14 d post-transduction), G3BP1-BFP, G3BP1 B domain-BFP, and G3BP1 D domain-BFP were visible in the regenerating sciatic nerve axons. The G3BP1 B domain-BFP transduced animals showed significantly increased axon regeneration compared to G3BP1-BFP, and G3BP1 D domain-BFP, and GFP transduced animals (FIG. 9C). To test for the possibility of accelerated regeneration, the inventors measured compound muscle action potentials (CMAP) in lateral gastrocnemius (LG) and tibialis anterior (TA) muscles to assess functional reinnervation after axotomy in control versus B domain-transduced animals.

Figure 9D:
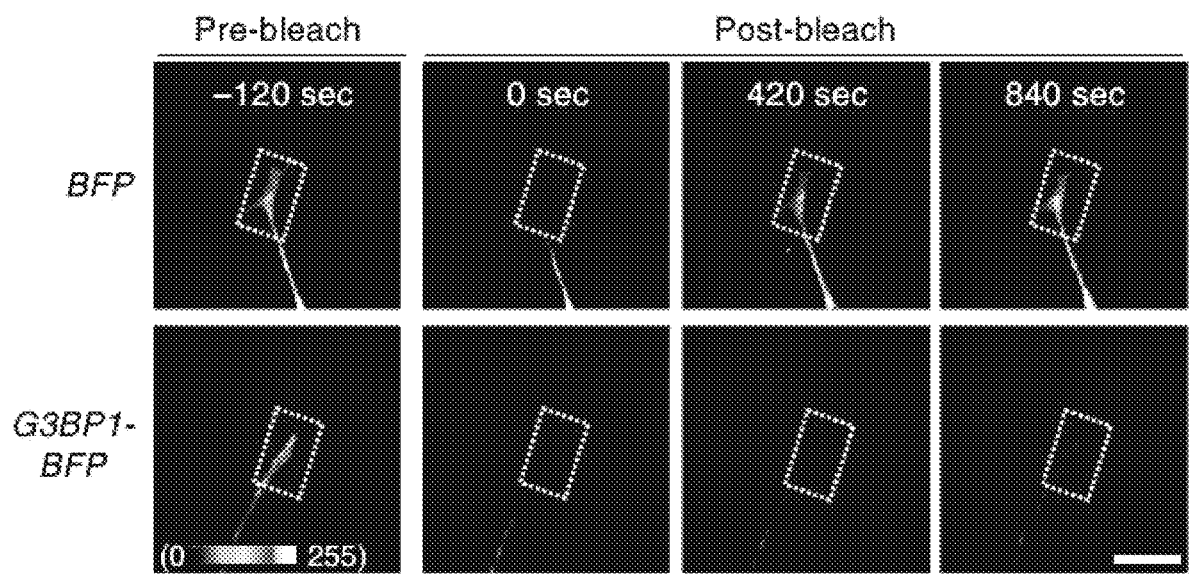
FIG. 9D shows representative FRAP image sequences for DRG neurons co-transfected with GFP$^{MYR}$ 5'/3'nrn1 plus BFP or G3BP1-BFP.

Significantly accelerated recovery of CMAPs was seen with G3BP1 B domain expression in the LG at 4 and 6 wks and the TA at 4 wk after sciatic nerve crush, with control catching up by 8 wk in LG and 6 wk in TA (FIG. 9D). The apparent faster recovery in the TA likely relates to the shorter regeneration distance and smaller muscle mass compared to the LG. Taken together, these data indicate that expression of the G3BP1 B domain accelerates peripheral nerve regeneration.

To determine if a smaller region of the G3BP1 B domain is sufficient to increase axon growth, the inventors generated fluorescently labeled, cell-permeable Tat fusion peptides corresponding to residues 147-166, 168-189, and 190-208 of rat G3BP1. These peptides each penetrated the neurons in DRG cultures by 30 min. after application. When added to DRG cultures immediately after plating, both the 147-166 and 190-208 peptides increased axon length; the 190-208 peptide also increased the number of neurites per neuron. Since the 190-208 peptide showed the longest axons and increased the overall number of neurites extended from each neuron, the inventors focused their efforts on this peptide, in comparison to the 168-189 peptide that lacked activity.

Figure 9E:
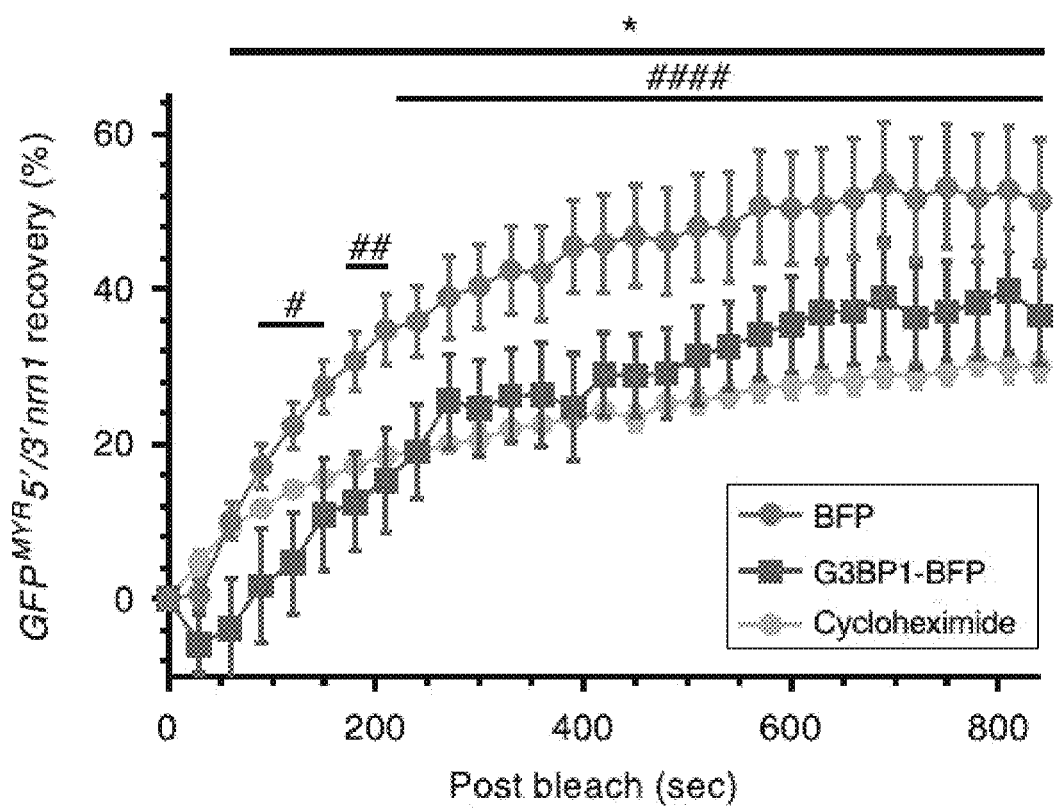
FIG. 9E shows quantifications of FRAP assays from DRGs expressing GFP$^{MYR}$ 5'/3'nrn1.
Figure 9F:
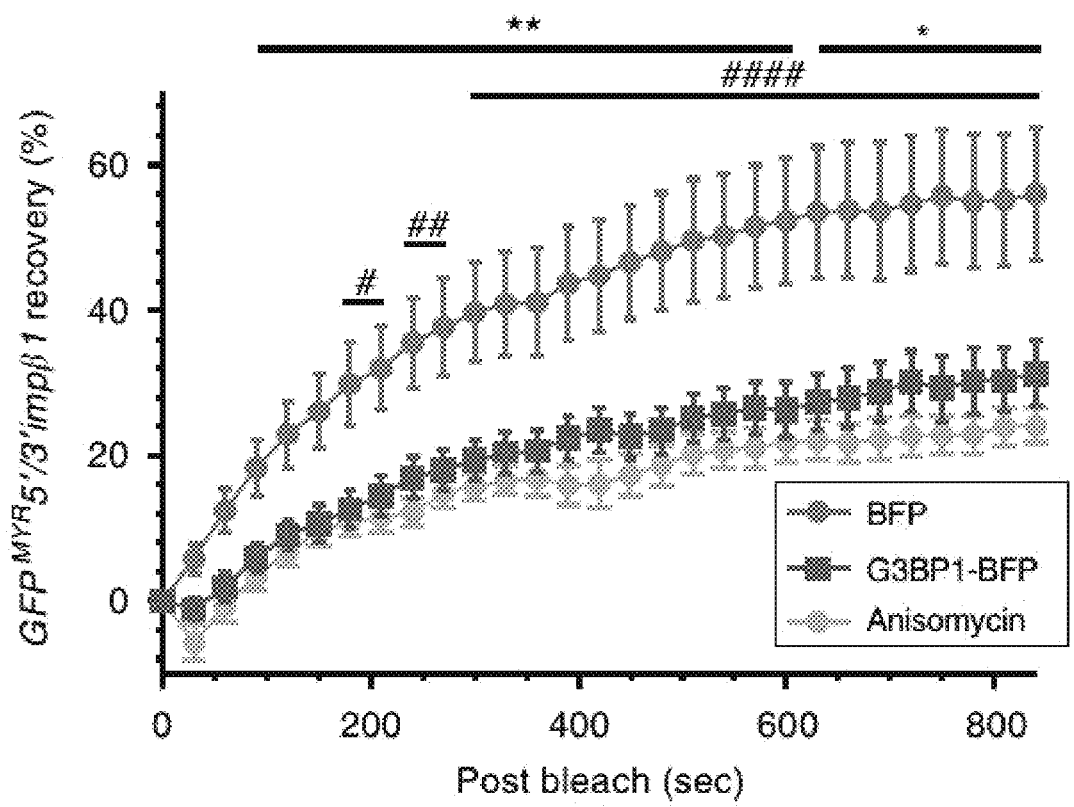
FIG. 9F shows quantifications of FRAP assays from DRGs expressing GFP$^{MYR}$ 5'/3'impβ1.
Figure 9G:
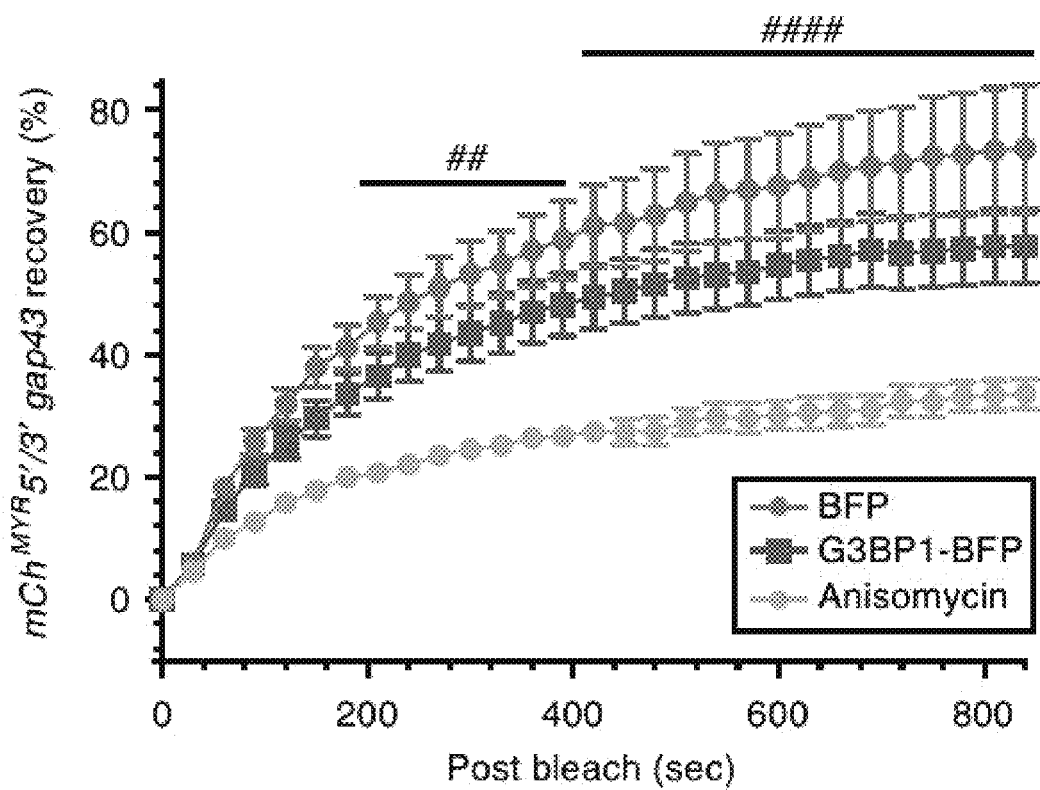
FIG. 9G shows quantifications of FRAP assays from DRGs expressing mCh$^{MYR}$ 5'/3'gap43.
Figure 9H:
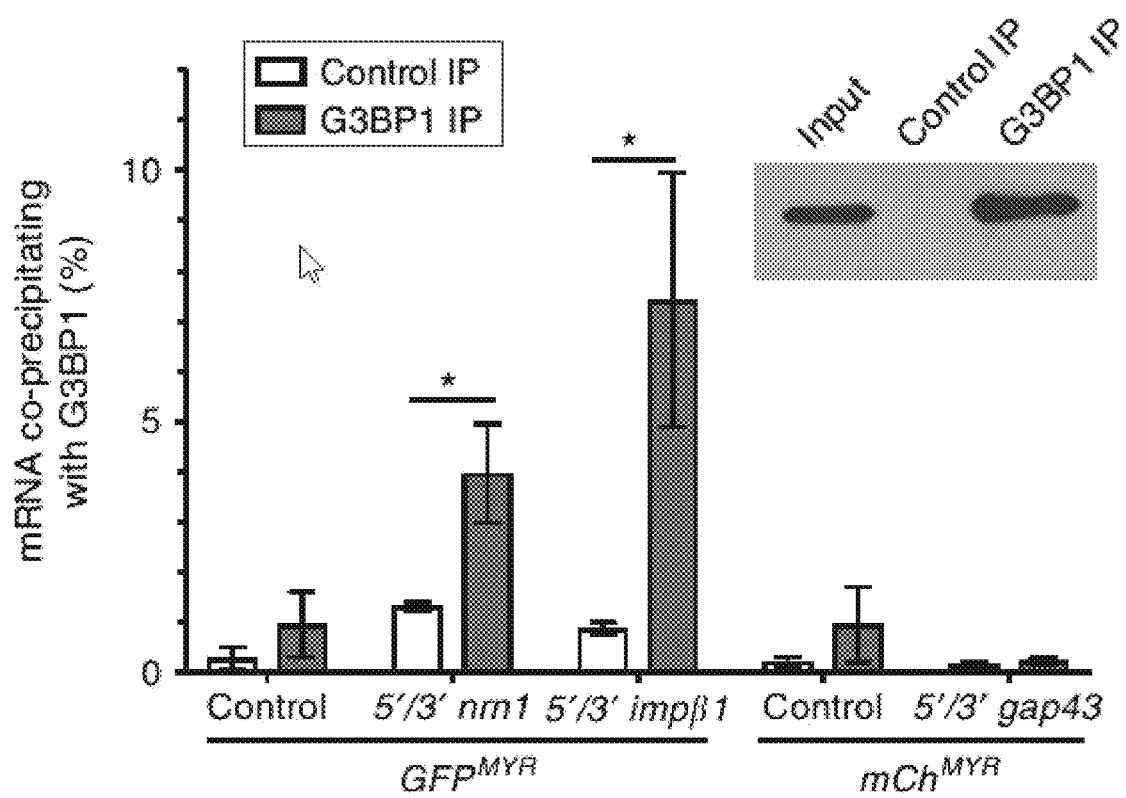
FIG. 9H shows HEK293T cells transfected with GFP$^{MYR}$ 5'/3'nrn1, GFP$^{MYR}$ 5'/3' impβ1, and mCh$^{MYR}$ 5'/3'gap43 show significant enrichment of GFP$^{MYR}$ 5'/3'nrn1 and GFP$^{MYR}$ 5'/3' impβ1 mRNAs coimmunoprecipitating with G3BP1 versus control.

To discriminate between increased axon extensions versus earlier initiation of axon growth, the inventors exposed DRG cultures to peptides after the neurons had fully initiated axonal growth. With delayed application, the 190-208 peptide significantly increased axon length in both naive and preinjured DRG neurons (FIG. 9E). E18 cortical neuron cultures also showed a significant increase in axon growth when the 190-208 peptide was applied to the axonal compartment of microfluidic culture devices (FIG. 9E). Finally, the 190-208 peptide significantly increased neurite length in cultures of motor neurons generated from human induced pluripotent stem cells. These data indicate that introducing amino acids 190-208 of rat G3BP1 increases axon growth in rodent and human neurons, and likely does so through an axon intrinsic mechanism(s).

Figure 10A:
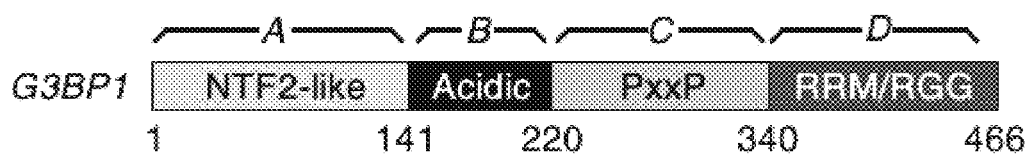
FIG. 10A shows a schematic of G3BP1 domains.
Figure 10B:
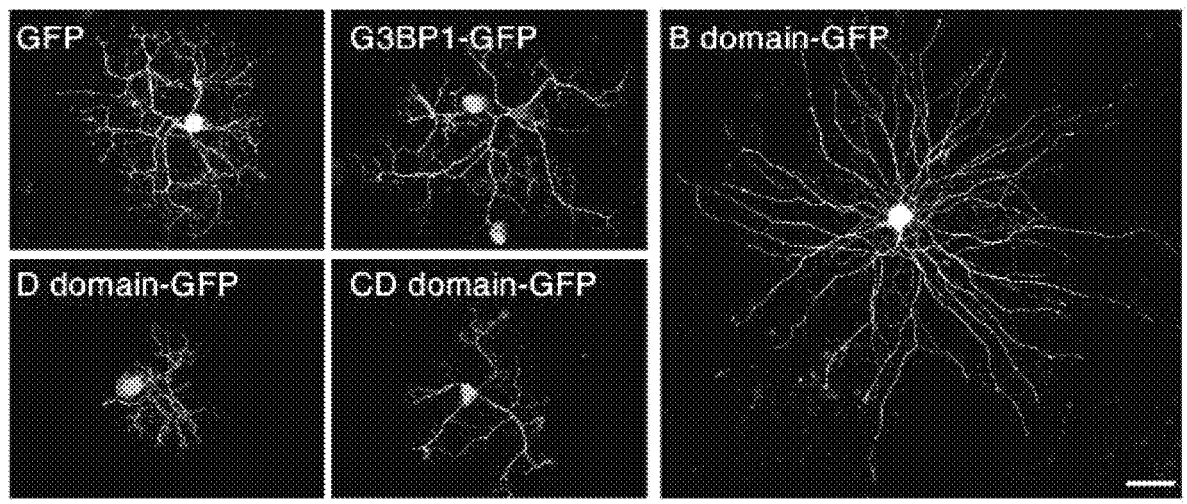
FIG. 10B shows representative images for NF-labeled DRG neurons transfected with indicated constructs.
Figure 10C:
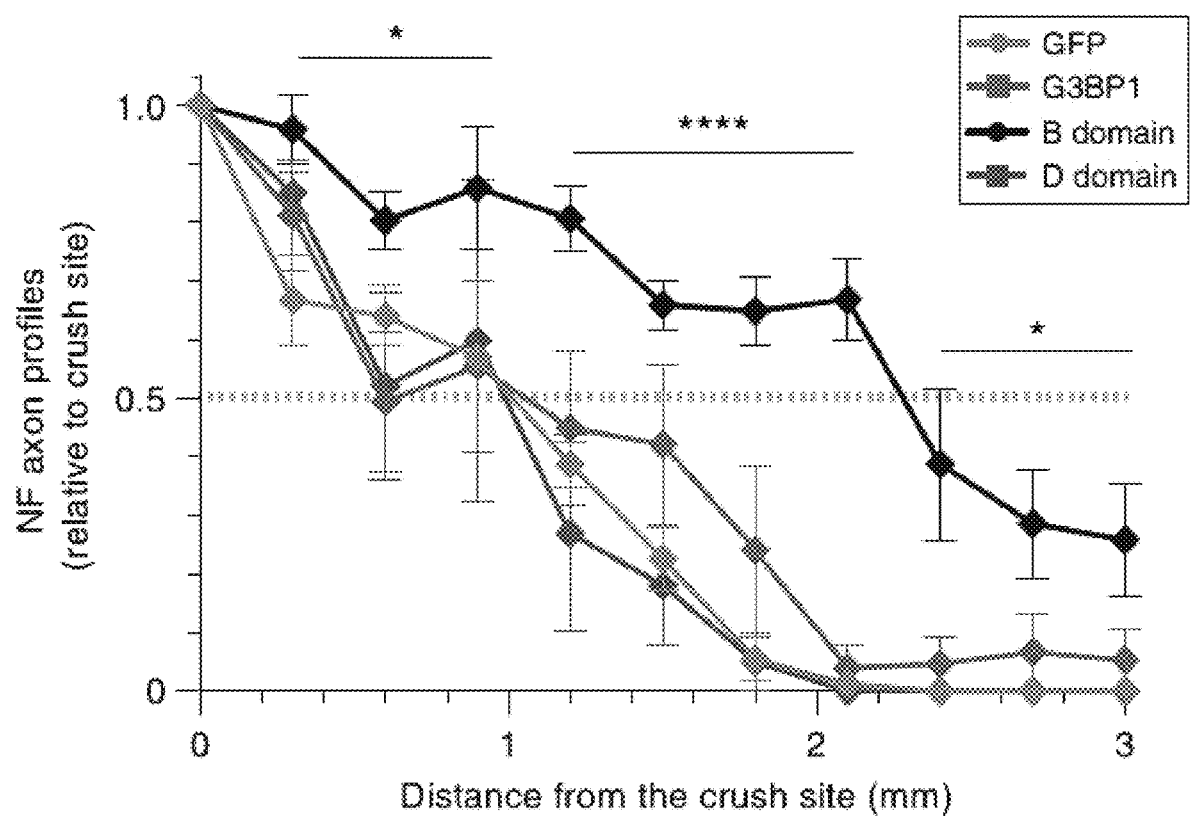
FIG. 10C shows the extent of axon regeneration at 7 d post sciatic nerve crush in adult rats transduced with AAV5 encoding G3BP1-BFP, G3BP1 B domain-BFP, G3BP1 D domain-BFP, or GFP control.

The G3BP1 acidic domain disassembles stress granule protein aggregates. To determine if expression of the G3BP1 B domain interrupts the function of endogenous G3BP1, the inventors asked if expressing the B domains alters axonal mRNA translation. Using a puromycinylation assay to test for translation of endogenous mRNAs, G3BP1 B domain expression led to significantly higher protein synthesis in axons but not cell bodies of cultured DRGs (FIGS. 10A and 10B). Depletion of G3BP1 similarly increased protein synthesis in the DRG axons with no significant effect on protein synthesis in the cell bodies (FIG. 10C).

Figure 10D:
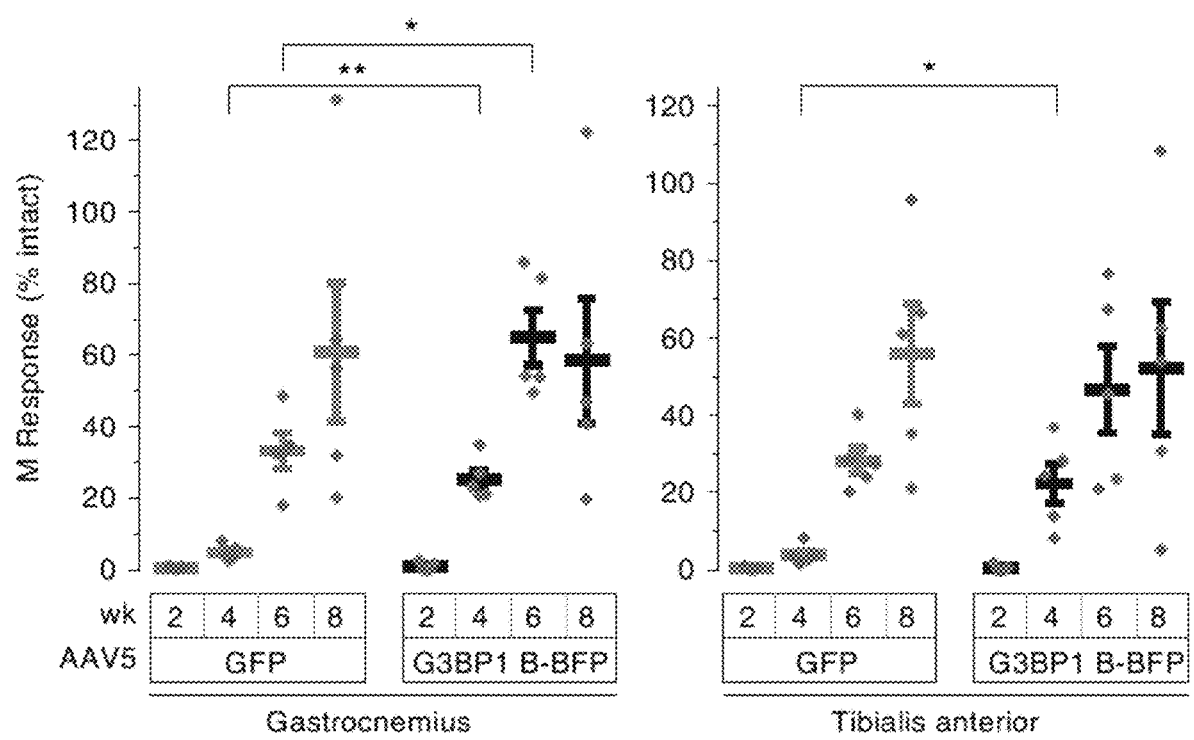
FIG. 10D shows animals transduced with AAV5 encoding G3BP1 B domain-BFP versus GFP were subjected to sciatic nerve crush and regeneration was assessed by muscle M response in tibialis anterior and gastrocnemius.

Expression of the G3BP1 B domain also leads to increases in axonal but not in cell body levels of Nrn1 protein, without affecting axonal or cell body levels of Impβ1 or Gap43 proteins (FIG. 10D). Overexpression of full-length G3BP1 caused a decrease in axonal levels of both Nrn1 and Impβ1 proteins. Since both Nrn1 and Impβ1 mRNAs colocalized with G3BP1 and the GFP$^{MYR}$ 5'/3'nrn1 and GFP$^{MYR}$ 5'/3'impb1 reporter mRNAs coprecipitated with G3BP1, the inventors asked if endogenous Nrn1 and Impβ1 mRNA binding to G3BP1 might be affected by the introduction of the B domain. Co-precipitation of these mRNAs with G3BP1-BFP was significantly reduced in neurons co-transfected with B domain-BFP construct (FIG. 10E).

Figure 10E:
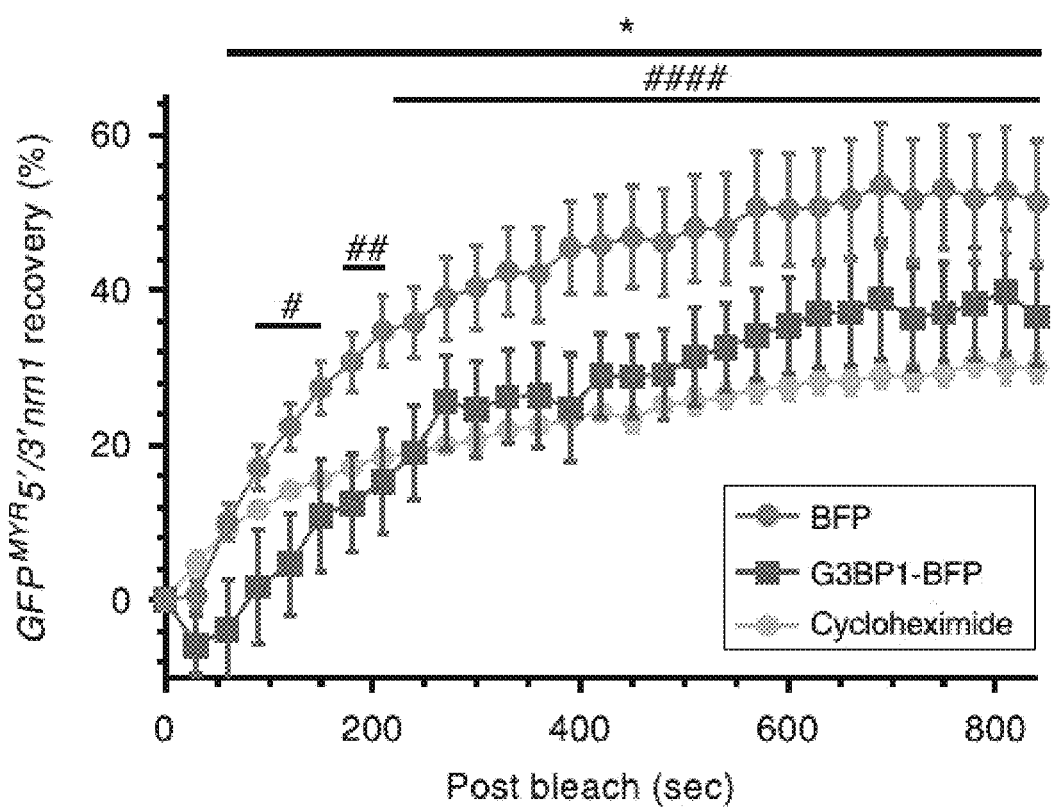
FIG. 10E shows quantitation of axon growth from DRGs (left) and cortical neurons (right) treated with cell-permeable 168-189 or 190-208 G3BP1 peptides.

GAP43 mRNA did show some binding to G3BP1-BFP, but this was not affected by the B domain expression, and none of these mRNAs precipitated with G3BP1 B domain-GFP or the control GFP (FIG. 10E). These data suggest that the G3BP1 B domain increases axonal protein synthesis by causing release of mRNAs from axonal G3BP1 aggregates.

Figure 11A:
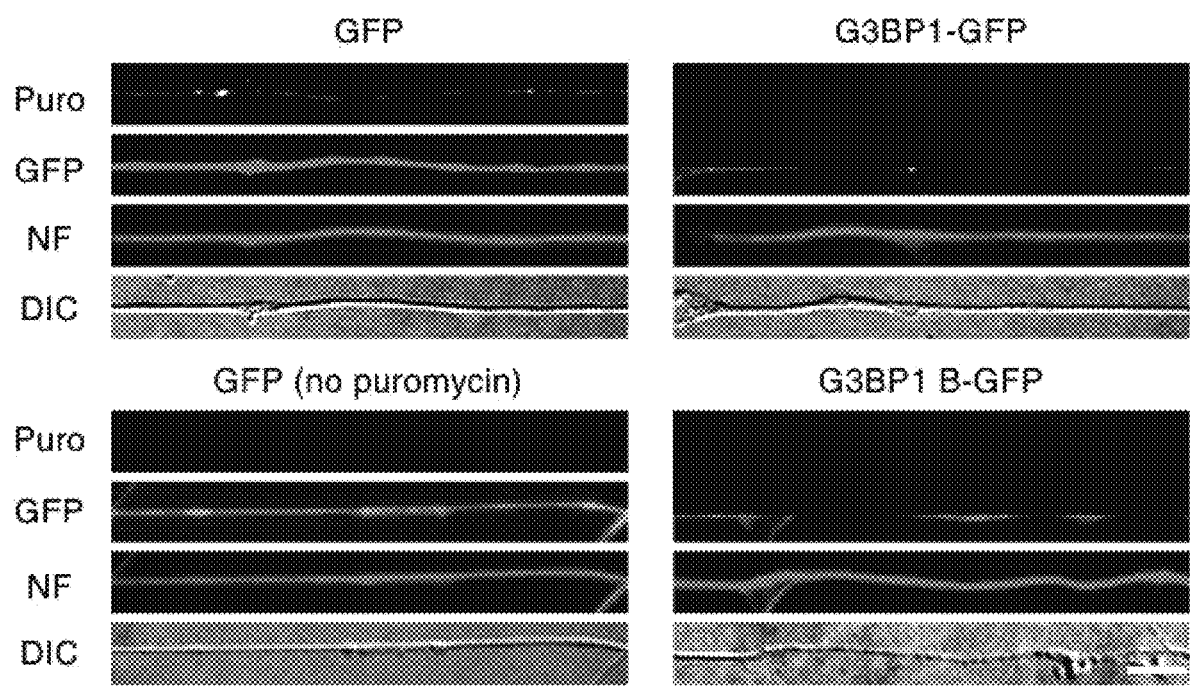
FIG. 11A shows representative images for puromycin (Puro) incorporation in DRG neurons transfected with the indicated constructs.
Figure 11B:
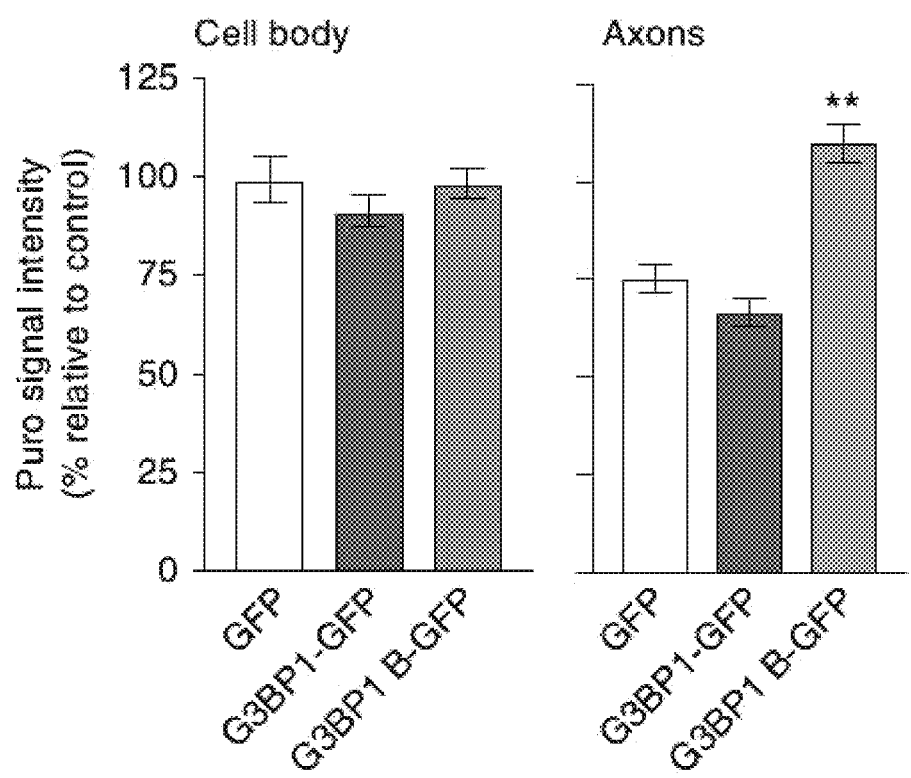
FIG. 11B shows significant increase in axonal puromycin signals in the G3BP1 B domain-expressing neurons with no significant change in the cell body puromycin incorporation.
Figure 11C:
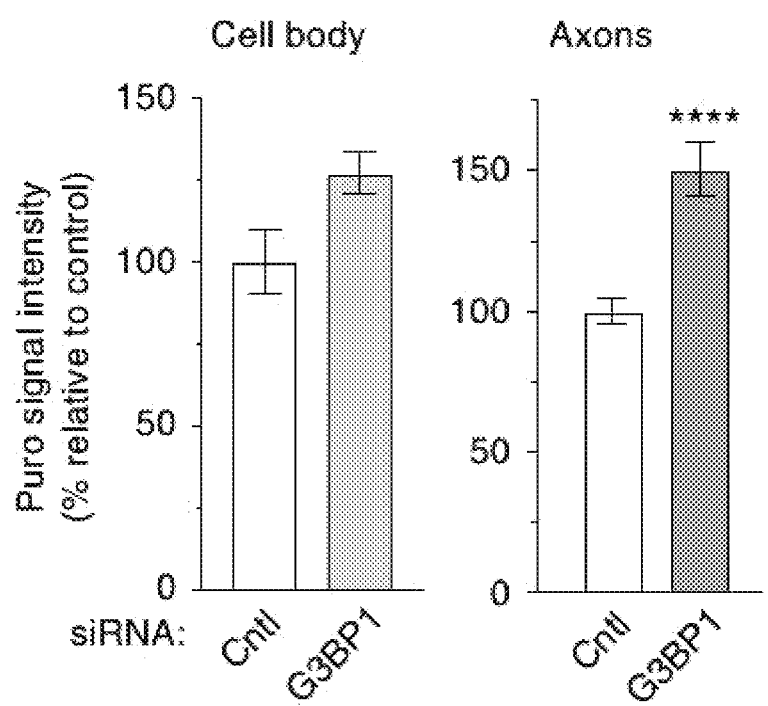
FIG. 11C shows that G3BP1 depleted DRG cultures similarly show increased puromycin incorporation in axons with no significant change in cell body puromycin incorporation.

In light of the changes in translation upon expression of the G3BP1 B domain, the inventors asked if the growth-promoting 190-208 peptide might also affect axonal protein synthesis. Treatment with the cell-permeable G3BP1 190-208 peptide significantly increased puromycin incorporation in DRG axons compared to untreated and G3BP1 168-189 peptide-treated cultures (FIGS. 11A and 11B). The 190-208 peptide also significantly increased axonal recovery of GFP$^{MYR}$ 5'/3'nrn1 fluorescence after photobleaching under control conditions and reversed the decrease in axonal translation seen with G3BP1 overexpression (FIG. 11C). The lack of effect previously observed for B domain expression on endogenous Impβ1 protein levels in axons was mirrored by the 190-208 peptide effects on GFP$^{MYR}$ 5'/'impβ1 and mCh$^{MYR}$ 5'/3' gap43 translation in axons under control conditions. Moreover, the 190-208 peptide did not rescue the decline in axonal translation of GFP$^{MYR}$ 5'/3'impβ1 seen with G3BP1 overexpression (FIG. 11C). Together, these data indicate that disrupting G3BP1 function with overexpression of the B domain or the 190-208 G3BP1 peptide can specifically increase intra-axonal translation of some mRNAs. Considering the effects of the G3BP1 B domain and 190-208 peptide on axonal mRNA translation, the inventors reasoned that these agents might disrupt SGs. Indeed, G3BP1 B domain expression attenuated SG aggregation in NIH 3T3 cells exposed to sodium arsenite.

Figure 11D:
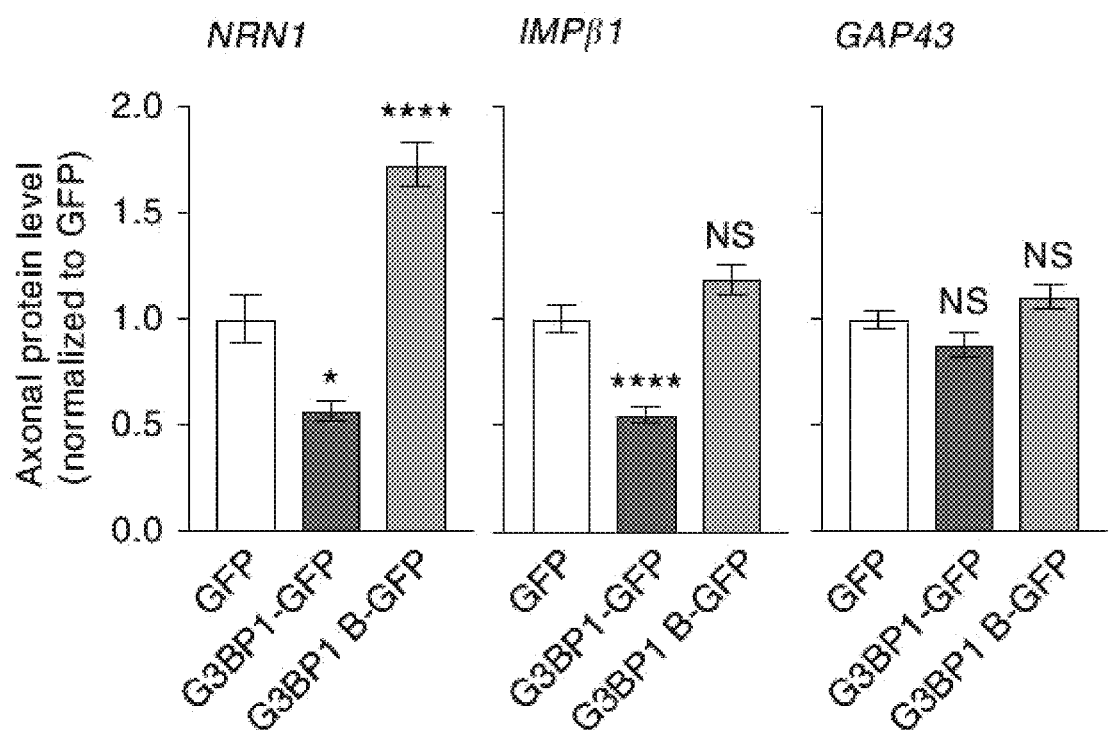
FIG. 11D shows quantitation of endogenous axonal NRN1, IMPβ1, and GAP43 protein levels in DRG cultures transfected with GFP, G3BP1-GFP, and G3BP1 B domain-GFP.
Figure 11E:
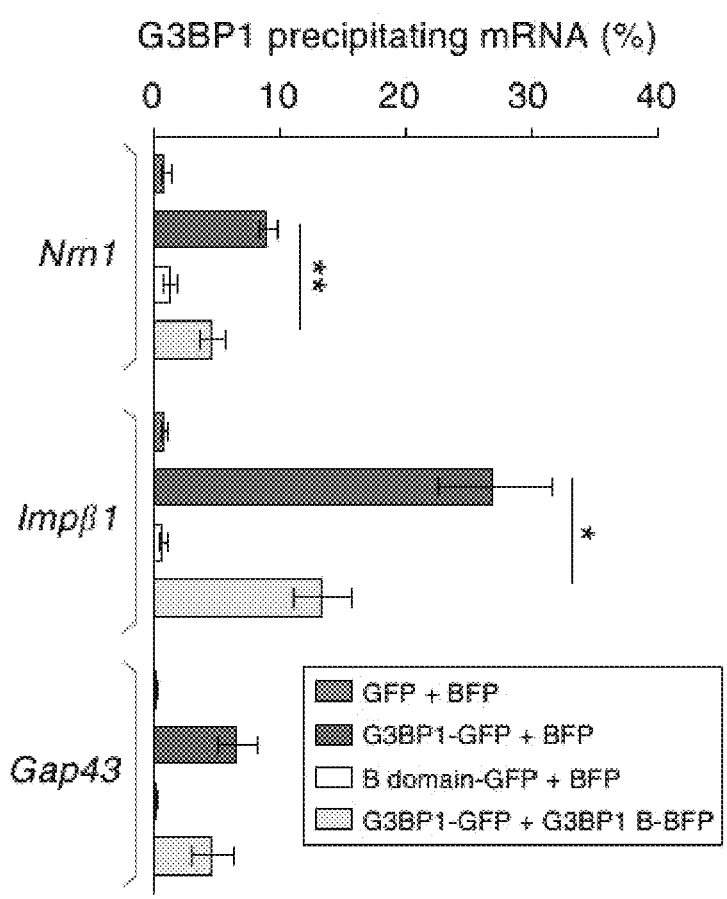
FIG. 11E shows RTddPCR for axonal mRNAs co-precipitating with G3BP1-GFP in DRG neurons.
Figure 12A:
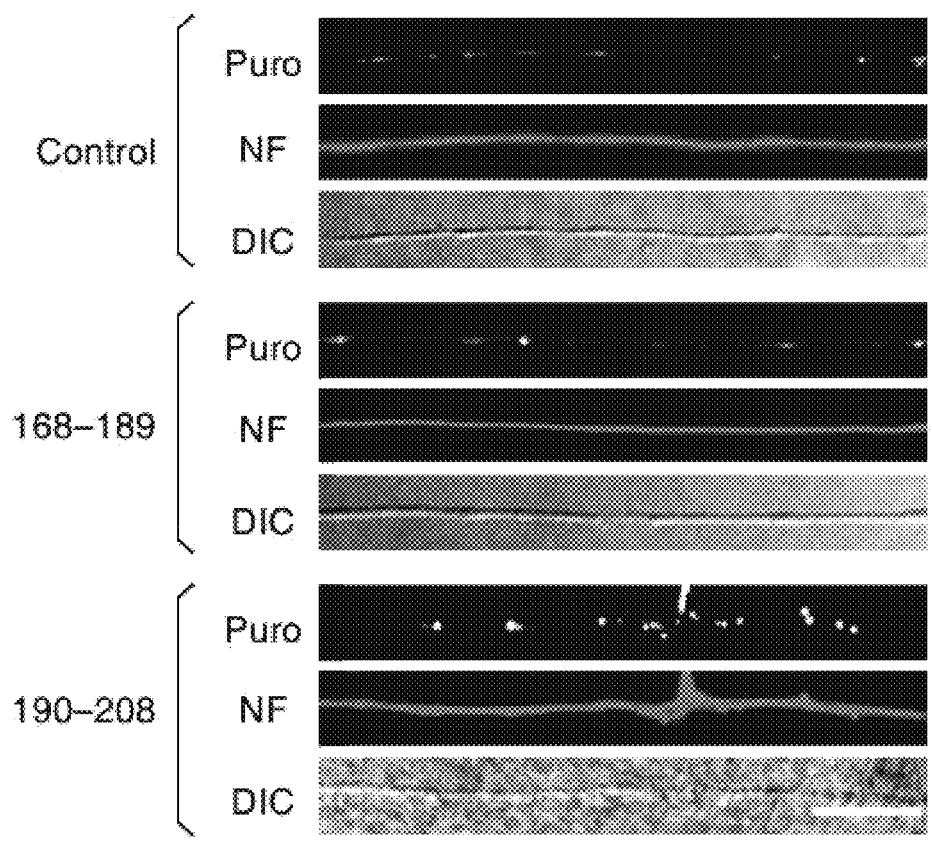
FIG. 12A shows representative images for puromycin incorporation in axons of control, 168-189 peptide and 190-208 peptide-treated DRG cultures are shown
Figure 12B:
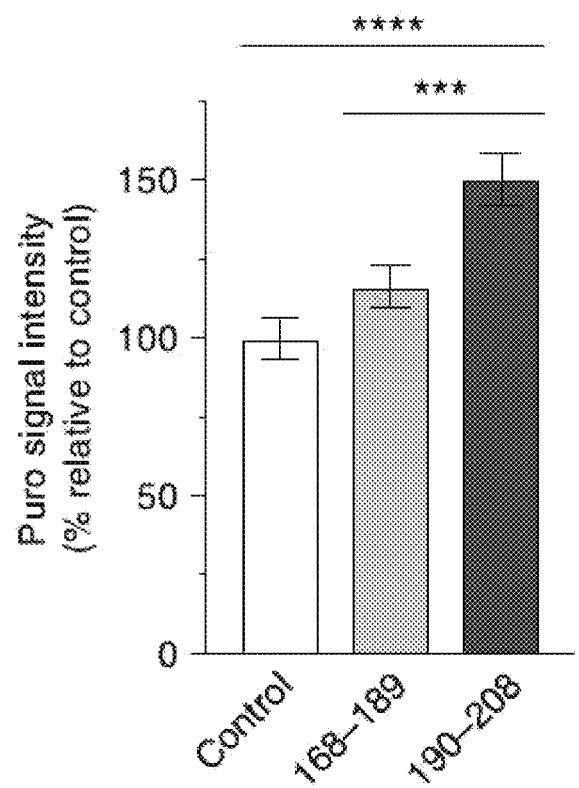
FIG. 12B shows quantitation of puromycin incorporation into distal DRG axons under these conditions shows a significant increase in axonal protein synthesis for the 190-208 peptide-treated cultures compared to control and 168-189 peptide exposure.
Figure 12C:
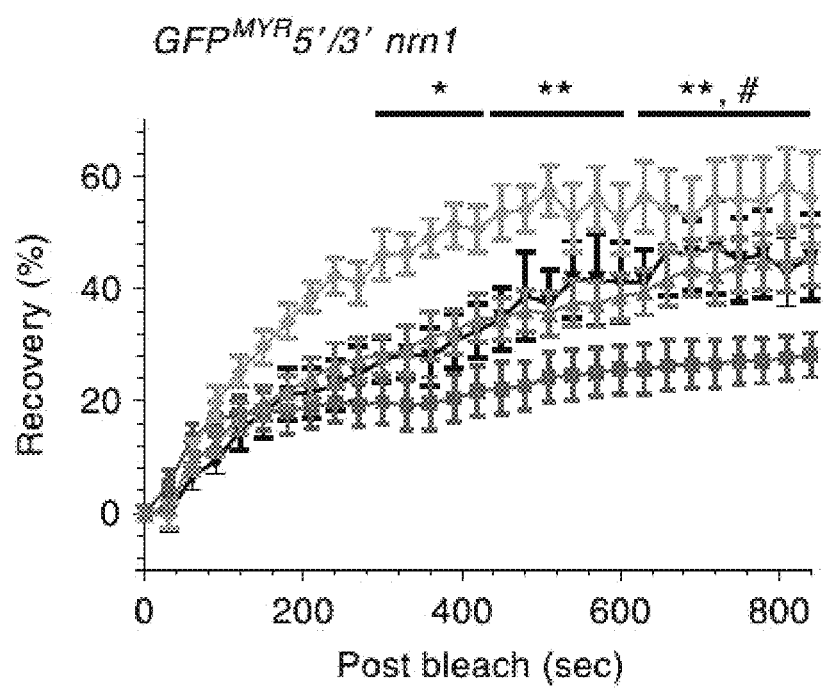
FIG. 12C shows FRAP analyses for DRGs for GFP$^{MYR}$ 5'/3'nrn1, GFP$^{MYR}$ 5'/3'impβ1 and GFP$^{MYR}$ 5'/3'gap43 in axons of DRGs expressing BFP or G3BP1-BFP±10 μM 190-208 G3BP1 peptide.
Figure 12D:
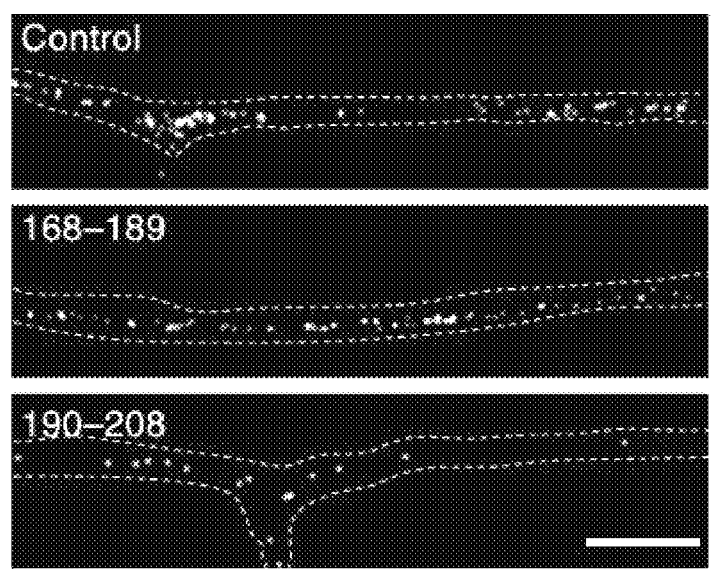
FIG. 12D shows representative images of G3BP1-mCh in DRG axons under control conditions and after treatment with 190-208 G3BP1 or 168-189 peptides for 15 min.
Figure 12E:
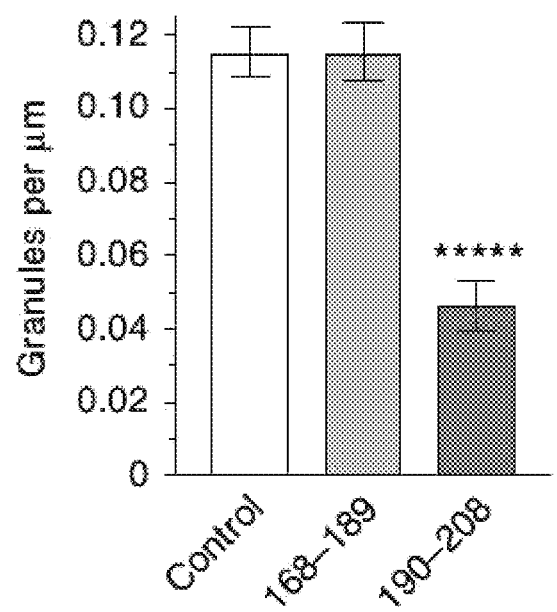
FIG. 12E shows density of G3BP1-mCh aggregates along 100 μm length axons from DRG cultures treated as in FIG. 12D.
Figure 12F:
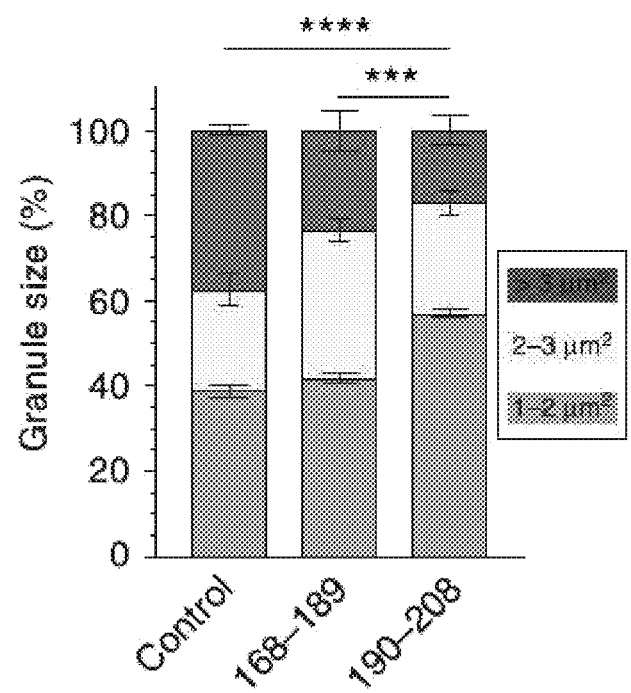
FIG. 12F shows the size of G3BP1-mCh aggregates from DRG cultures treated as in FIG. 12D.

As noted above, arsenite is a potent inducer of SG aggregation, so the inventors performed time-lapse imaging on DRG cultures to determine if the G3BP1 B domain affects the axonal SG-like structures. To this end, the inventors treated DRG cultures with the cell-permeable 190-208 G3BP1 peptide, and monitored G3BP1-mCherry aggregates. The 190-208 peptide caused a striking decrease in axonal G3BP1-mCherry aggregates after 15 min. (FIGS. 11D and 11E). Moreover, the remaining SG-like structures in axons were significantly smaller after 190-208 peptide treatment (FIG. 11F), and the remaining aggregates showed greater motility than in control conditions. In contrast, the 168-189 G3BP1 peptide caused no change in SG density along the axons (FIGS. 11D and 11E), and only modest but insignificant decrease in SG size (FIG. 11F). Together, these data indicate that the B domain expression and treatment with the 190-208 G3BP1 peptide disrupt aggregation of SG-like structures.

FIGS. 9A-9E show G3BP1 acidic domain expression accelerates nerve regeneration. a Schematic of G3BP1 domains as defined by Tourriere et al. (2003). b Representative images for NF-labeled DRG neurons transfected with indicated constructs are shown. Images were acquired at 60 h post-transfection [scale bar=100 μm]. c Extent of axon regeneration at 7 d post sciatic nerve crush in adult rats transduced with AAV5 encoding G3BP1-BFP, G3BP1 B domain-BFP, G3BP1 D domain-BFP, or GFP control is shown as mean axonal profiles relative to crush site (0 mm)±SEM. *=p≤0.05 and ****=p≤0.0001 between B domain-BFP versus GFP transduced animals by one-way ANOVA with Tukey HSD post-hoc). d Animals transduced with AAV5 encoding G3BP1 B domain-BFP versus GFP were subjected to sciatic nerve crush and regeneration was assessed by muscle M response in tibialis anterior and gastrocnemius. Values are shown as average % intact M responses±SEM (lines) with data points for individual animals plotted (*p≤0.05 and p≤0.01 for B domain versus GFP by Student's t-test for indicated data pairs). e Quantitation of axon growth from DRGs (left) and cortical neurons (right) treated with cell-permeable 168-189 or 190-208 G3BP1 peptides is shown. For DRGs, peptides were added to dissociated naive or 7 d injury-conditioned DRGs at 12 h and axon growth was assessed at 36 h in vitro. For cortical neurons, peptides were added to the axonal compartment of microfluidic devices at 3 d in vitro (DIV), and axon growth was assessed at 6 DIV. *p≤0.005 by one-way ANOVA with Tukey HSD post-hoc)

FIGS. 10A-10E show G3BP1 acidic domain increases axonal mRNA translation and disassembles stress granules. a, b Representative images for puromycin (Puro) incorporation in DRG neurons transfected with the indicated constructs are shown (a). Significant increase in axonal puromycin signals in the G3BP1 B domain-expressing neurons is seen, with no significant change in the cell body puromycin incorporation (b; N≥23 axons over three repetitions; p≤0.01, p≤0.0001 by one-way ANOVA with Tukey HSD post hoc) [scale bar=5 µm]. c G3BP1 depleted DRG cultures similarly show increased puromycin incorporation in axons with no significant change in cell body puromycin incorporation (N≥23 axons over three repetitions; p≤0.01, ****p≤0.0001 by one-way ANOVA with Tukey HSD post hoc). d Quantitation of endogenous axonal NRN1, IMPβ1, and GAP43 protein levels in DRG cultures transfected with GFP, G3BP1-GFP, and G3BP1 B domain-GFP is shown.

Axonal NRN1 and IMPβ1 but not GAP43 levels are significantly reduced in G3BP1 overexpression. G3BP1 B domain-expressing neurons show significantly higher axonal NRN1, but no change in axonal IMPβ1 and GAP43 levels (N≥33 axons over three repetitions; *p≤0.05, ****p≤0.0001 by one-way ANOVA with Tukey HSD post hoc). e RTddPCR for axonal mRNAs co-precipitating with G3BP1-GFP in DRG neurons are shown as average % mRNA associated with G3BP1-GFP±SEM. Nrn1 and Impβ1 mRNAs association with G3BP1-GFP significantly reduced by cotransfection with the G3BP1 B domain, but neither RNA coprecipitates with the B domain (N=4 culture preparations; *p≤0.05, **p≤0.01 by Student's t-test for the indicated data pairs)

Studies have now documented mRNA translation in axons, and this is particularly prominent in the PNS where intra-axonal protein synthesis contributes to axon regeneration after injury. Some SG proteins have been detected in axons of PNS nerves, but intra-axonal functions for these proteins were only inferred from known functions of these proteins in other cellular systems. The inventors' data indicate that blocking G3BP1's function in the assembly of axonal S and accelerates PNS axon regeneration. Thus, axonal G3BP1 is a negative modulator of intra-axonal protein synthesis and axon growth. Since several thousand mRNAs have been identified in axons of cultured neurons, it is likely that translation of many axonal mRNAs could be regulated by G3BP1, as the inventors show here for Impβ1 and Nrn1 mRNAs. The colocalization of different mRNAs G-like structures increases intra-axonal protein synthesis with these G3BP1 aggregates correlates with the growth status of neurons, and blocking G3BP1 aggregation provides a novel strategy to accelerate regeneration.

Assembly of SGs has been well characterized in response to different metabolic and oxidative stressors in non-neural systems. The rapid increase in SG-like structures seen here by 3 h after axotomy could reflect a stress response by the PNS axons, with a decrease in SG-like aggregates during axon growth at later time points. The decrease in G3BP1 aggregation was accompanied by an increase in phospho-G3BP1. Casein kinase 2 and AKT have recently been reported to phosphorylate G3BP1 on Ser 149 in other cellular systems. Both of these proteins are present in axons, and it will be of interest for future work to determine their roles in intra-axonal signaling cascades regulating G3BP1 phosphorylation. Notably, the inventors see aggregates of G3BP1 and TIA1 in uninjured PNS axons and G3BP1 aggregates in axon shafts of cultured neurons with growing axons. The inventors suspect that these structures correspond to the 'core SGs' that have been defined in other cell types. Recent proteomics analyses for SG protein interactomes, including the G3BP1 protein analyzed herein, point to pre-assembly of some SG proteins under non-stress conditions. These interactomes also included HuR (also known as ELAVL1), FXR1, FMRP, and TIA1 proteins that the inventors show colocalize with axonal G3BP1 protein. Consistent with the possibility of a core SG present in uninjured and growing axons, as the inventors' work suggests, core SG components were recently shown to interact in neurites of human IPSC-derived motor neurons before application of arsenic.

The inventors study notably shows that axonal G3BP1 and TIA1 do not always colocalize. Likewise, the Pearson's coefficient for colocalization of G3BP1 with SG components is low despite being statistically higher than the coefficients for G3BP1 with PB proteins. Overexpression of G3BP1 was shown to precipitate SG assembly in the absence of any stress in non-neuronal cells. Only some of the aggregates seen with overexpressed G3BP1 colocalize with TIA1, but G3BP1-associating mRNAs were found in both TIA1-positive and TIA1-negative G3BP1 aggregates. Thus, it is likely that the axonal G3BP1 aggregates seen here that are separate from TIA1 can also interact with mRNAs.

Regardless of whether the axonal G3BP1 aggregates are classic SGs or even core SG aggregates, the inventors' data clearly show these axonal aggregates attenuate axonal protein synthesis and limit rates of axon growth, so the axonal G3BP1 aggregates are biologically significant. Future studies will be needed to compare and contrast the constituents of these axonal G3BP1 aggregates to those of classic SGs.

The translation of different axonal mRNAs will undoubtedly show a high degree of regulatory complexity, and it is likely that numerous axonal mRNAs could be regulated by G3BP1 interactions.

Interestingly, all axonal mRNAs were not regulated by the G3BP1 aggregates, since Gap43 showed comparatively low interaction with G3BP1 and its translation was not affected by G3BP1 overexpression or B domain manipulations. This may reflect differences in post-transcriptional regulation between Gap43, Nrn1 and Impβ1 mRNAs in axons. Impβ1 mRNA is constitutively transported into axons, where its localized translation is activated through $Ca^{2+}$-dependent pathways after axotomy. In contrast, Nrn1's transport into axons is increased after axotomy, with the mRNA shifting from soma-predominant to axon-predominant during regeneration. On the other hand, Gap43's transcription is increased approximately 5 fold after axotomy, with increased axonal localization commensurate with an overall increase in Gap43 levels. Based on the low colocalization of Gap43 with G3BP1 and the lack of effect of G3BP1 on its translation, Gap43 mRNA does not seem to be regulated by the axonal SG-like structures. It is intriguing to speculate that differences in transcriptional versus post-transcriptional regulation contribute to whether individual mRNAs are regulated by the axonal SG-like structures. Such distinctions would segregate the axonal transcriptome into mRNA cohorts based on the mechanisms of their transcriptional and/or translational regulation and axonal transport.

The difference between Impβ1 and Nrn1 colocalization with G3BP1 in naive versus injury-conditioned neurons likely reflects different needs for the corresponding proteins in different growth states. DRG neurons that are pre-injured by an in vivo axotomy days prior to culturing show rapid elongation of relatively unbranched axons that is transcription independent. This rapid axonal growth occurs through translational control of existing mRNAs, and the injury-conditioned neurons show higher intra-axonal protein synthesis than naive DRG neurons. Nrn1 protein promotes neurite growth, and increasing axonal targeting of Nrn1 mRNA increases axon growth. Hence, the decrease in Nrn1 mRNA associated with SG-like aggregates in axons of injury-conditioned neurons would free the mRNA for translation to promote axon growth. On the other hand, Impβ1 mRNA translation is induced by axotomy, with its protein product providing a retrograde signal to activate regeneration-associated gene expression in the soma. Continued translation of Impβ1 mRNA likely decreases axon elongation due to its role in axon length sensing. Consequently, rapid axon growth after injury conditioning could also be facilitated by sequestering Impβ1 mRNA from translation.

Both Nrn1 and Impβ1 mRNAs were released from interaction with G3BP1 when the G3BP1 B domain was introduced. Since the B domain did not co-precipitate these mRNAs, the release of mRNAs from G3BP1 interaction is not via a competitive interaction for mRNA binding by the B domain with full length G3BP1. Though axonal translation of both Nrn1 and Impβ1 was decreased by overexpression of G3BP1, only Nrn1 showed increased translation in response to B domain expression and 190-208 peptide treatment. This indicates that the release of stored mRNAs in axons is not sufficient for their translation.

Additional stimuli are undoubtedly needed to translate Impβ1 mRNA compared to Nrn1 mRNA. Impβ1 mRNA was initially shown to be translated in axons after injury and this requires an increase in axoplasmic $Ca_{2+}$ levels. Increased $Ca_{2+}$ is known to trigger phosphorylation of eIF2α, and phosphomimetic eIF2α was shown to increase the translation of axonal Calr and Hspa5 mRNAs in cultured DRG neurons. Thus, axoplasmic $Ca_{2+}$ levels may provide one regulatory mechanism for determining which mRNAs are translated upon release from the axonal SG-like structures. Differential susceptibility to mTOR regulation may provide an additional layer of regulation, as frequently reported for survival promoting retrograde injury signals in peripheral nerve.

In summary, the inventors study points to axonal G3BP1 as a specific modulator of intra-axonal protein synthesis and axon growth. Since G3BP1 is aggregated in uninjured PNS axons, the inventors' data point to unrealized functions for SG-like aggregates in axons under non-stress conditions. Preventing this SG-like aggregation of axonal proteins during regeneration increases the rate of axon regrowth. Considering that Tat fusion peptides for NR2B9c have been used in a clinical trial for ischemic protection during endovascular repair for intracranial aneurysms, the growth promoting effects of the cell-permeable 190-208 G3BP1 peptide may represent a novel therapeutic lead for accelerating nerve regeneration. Since peripheral nerves typically regenerate at only 1-2 mm per day, accelerating axon growth rates by interfering with axonal G3BP1 function could significantly shorten recovery times and allow axons to reach a more receptive environment to reinnervate target tissues.

FIGS. 11A-11F show Cell permeable G3BP1 190-208 peptide increases axonal mRNA translation and disassembles stress granules. a, b, Representative images for puromycin incorporation in axons of control, 168-189 peptide and 190-208 peptide-treated DRG cultures are shown (a). Quantitation of puromycin incorporation into distal DRG axons under these conditions shows a significant increase in axonal protein synthesis for the 190-208 peptide-treated cultures compared to control and 168-189 peptide exposure (b; N≥83 axons over 3 DRG cultures; *p≤0.005, **p≤0.0001 by one-way ANOVA with Tukey HSD post-hoc). c FRAP analyses for DRGs for $GFP^{MYR}$ 573'nrn1, $GFP^{MYR}$ 5'/3'impβ1 and $GFP^{MYR}$ 5'/3'gap43 in axons of DRGs expressing BFP or G3BP1-BFP±10 μM 190-208 G3BP1 peptide (30 min. treatment). Only translation of $GFP^{MYR}$ 5'/3'nrn1 is increased by the 190-208 peptide with G3BP1 overexpression (N≥11 axons over three culture repetitions; all statistics were done by one-way ANOVA with Tukey HSD post-hoc: *p≤0.05, **p≤0.01 for BFP versus BFP+190-208 peptide; *p≤0.05 for G3BP1-BFP versus G3BP1-BFP+190-208; p≤0.05 for BFP versus G3BP1; and, *p≤0.05 for BFP versus G3BP1-BFP+190-208 peptide; no values for $GFP^{MYR}$ 5'/3'gap43 were statistically significant). d Representative images of G3BP1-mCh in DRG axons under control conditions and after treatment with 190-208 G3BP1 or 168-189 peptides for 15 min. are shown. Axon tracing was generated from DIC images [scale bar=10 μm]. e Density of G3BP1-mCh aggregates along 100 μm length axons from DRG cultures treated as in d is shown (N≥38 axons over three repetitions; **p≤0.0001 by ANOVA with Tukey HSD post-hoc). f Size of G3BP1-mCh aggregate is shown as indicated bins for from DRG cultures treated as in d (N≥221 aggregates over three repetitions; p≤0.0005, ***p≤0.0001 for entire population distributions by Kolmogorov-Smirnov test)

Methods

Animal use and survival surgery. Institutional Animal Care and Use Committees of University of South Carolina, Emory University, and Weizmann Institute of Science approved all animal procedures. Male Sprague Dawley rats (175-250 g) were used for all sciatic nerve injury and DRG culture experiments. Embryonic day 18 (E18; male and female) rat pups were used for cortical neuron culture experiments.

Isofluorane was used for anesthesia for AAV transduction and peripheral nerve injuries, and ketamine plus xylazine was used for electrophysiology studies (see below).

For peripheral nerve injury, anesthetized rats were subjected to a sciatic nerve crush at mid-thigh as described. In cases where animals were transduced with virus prior to injury, AAV5 was injected into the proximal sciatic nerve 7 d prior to crush injury (at sciatic notch level; $9\text{-}14 \times 10_{10}$ particles in 0.6 M NaCl).

Axoplasm was obtained from sciatic nerve at 3-28 d after crush injury at mid-thigh level. Approximately 3 cm segments of nerve proximal to the injury site (or equivalent level on contralateral [naive] side) were dissected and axoplasm extruded into 20 mM HEPES [pH 7.3], 110 mM potassium acetate, and 5 mM magnesium acetate (nuclear transport buffer) supplemented with protease/phosphatase inhibitor cocktail (Roche) and RNasin Plus (Promega). After clearing by centrifugation at 20,000×g, 4° C. for 30 min., supernatants were mixed with 3 volumes of Trizol LS (Invitrogen) and processed for mass spectrometry (see below). Three animals were used for each time point.

Cell culture. For primary neuronal cultures, L4-5 DRG were harvested in Hybernate-A medium (BrainBits) and then dissociated as described. After centrifugation and washing in DMEM/F12 (Life Technologies), cells were resuspended in DMEM/F12, 1×N1 supplement (Sigma), 10% fetal bovine serum (Hyclone), and 10 µM cytosine arabinoside (Sigma). Dissociated DRGs were plated immediately on laminin/poly-L-lysine-coated coverslips or transfected (see below) and then plated on coated coverslips.

For cortical neuron cultures, E18 cortices were dissected in Hibernate E (BrainBits) and dissociated using the Neural Tissue Dissociation kit (Miltenyi Biotec). For this, minced cortices were incubated in a pre-warmed enzyme mix at 37° C. for 15 min; tissues were then triturated and applied to a 40 µm cell strainer.

After washing and centrifugation, neurons were seeded at a density of $1\times10^5$ cells per poly-$_D$-lysine-coated microfluidic device (Xona Microfluidics). NbActive-1 medium (BrainBits) supplemented with 100 U/ml of Penicillin-Streptomycin (Life Technologies), 2 mM L-glutamine (Life Technologies), and 1×N21 supplement (R&D Systems) was used as culture medium.

Human induced pluripotent stem cells (hiPSCs) were maintained in dishes coated with Matrigel (Corning) in Flex8 media (ThermoFisher). hiPSCs were differentiated into human motor neurons using a directed differentiation protocol optimized by Kevin Eggan. 7000 neurons/well were plated on laminin—or CSPG coated 96 well plates. 100 µl at 10 µg/ml Laminin (ThermoFisher) and 25 ng CSPGs (Millipore) were used per well.

NIH-3T3 and HEK293T cells were maintained in DMEM (Life Technologies) supplemented with 10% FBS (Gibco) and 100 U/ml of Penicillin-Streptomycin (Life Technologies).

For DRG neuron transfection, dissociated ganglia were pelleted by centrifugation at 100×g for 5 min and resuspended in 'nucleofector solution' (Rat Neuron Nucleofector kit; Lonza). 5-7 µg plasmid was electroporated using an AMAXA Nucleofector apparatus (program SCN-8; Lonza). For siRNA transfection, 100 nM siRNAs (Dharmacon) were used with DharmaFECT 3 reagent and incubated for 36 h. A 3'UTR targeted siRNA (5'CCACAUAGGAGCUGG-GAAUUU 3') [SEQ ID NO: 7] was used for depleting G3BP1 for experiments assessing axon growth where siRNA-resistant G3BP1 constructs were used for rescue. Dharmacon On-target plus-SMART pool siRNA (Cat no. L101659-02-0005) against G3bp1 was used in antibody specificity testing and Puromycinylation assays. Non-targeting siRNAs were as control. RTddPCR and immunoblotting was used to test the efficiency of G3BP1 depletion (see below).

HEK293T cells were transfected using Lipofectamine® 2000 per manufacturer's instructions (Invitrogen). AAV5 preparations were titrated in DRG cultures by incubating with $1.8\text{-}2.8\times10^{10}$ particles of AAV5 overnight.

For arsenic treatment to induce SG aggregation, transfected NIH3T3 cells were grown to 60-80% confluence and were then treated with 0.5 mM sodium arsenite (Sigma) for 30 min.

For peptide treatments, 10 µM Tat-fused peptides were added to dissociated DRG cultures at 2 or 12 h after plating. Neurite outgrowth was assessed 24 h after addition of peptides. For the cortical cultures, 10 µM peptide was applied to the axonal compartment at 3 d in vitro (DIV) and axonal growth was assessed at 6 DIV. For iMotor neurons, 20 µM peptides were immediately added and neurite growth was assessed 24 h later.

Plasmid and viral expression constructs. All fluorescent reporter constructs for analyses of RNA translation were based on eGFP with myristoylation element ($GFP^{MYR}$; originally provided by Dr. Erin Schuman, Max-Plank Inst., Frankfurt) or mCherry plasmid with myristoylation element ($mCh^{MYR}$). Reporter constructs containing 5' and 3'UTRs of rat Nrn1 and Gap43 mRNAs have been published. For Impβ1, the rat 5'UTR was cloned by PCR and inserted directly upstream of the initiation codon in $GFP^{MYR}$ 3'impβ1.

Human G3BP1 wild type, S149A, S149E and deletion constructs as GFP-tagged proteins were generously provided by Dr. Jamal Tazi, Institut de Génétique Moléculaire de Montpellier. The G3BP1-mCherry construct was generated by PCR, amplifying G3BP1 coding sequence with 5' NheI and 3' HindIII restriction sites. After NheI+HindIII digestion, G3BP1 CDS was subcloned into NheI+HindIII-digested pmCherry-N1 vector (Clontech).

AAV5 preparations were generated in UNC Chapel Hill Viral Vector Core. All plasmid inserts were fully sequenced prior to generating AAV. BglII+XhoI digested human G3BP1 cDNA (from pGFP-G3BP1) was subcloned into BamHI+XhoI digested pAAV-cDNA6-V5His vector (Vector Biolabs). G3BP1 deletion constructs were amplified by PCR with terminal HindIII and XhoI restriction sites (primer sequences available on request). After digestion with HindIII and XhoI, products were cloned into HindIII+XhoI-digested pAAV-cDNA6-V5His vector.

BFP was excised from the pTagBFP-N vector (Evrogen) using EcoRI+NotI and ligated in-frame directly 3' to the G3BP1 sequences in pAAV-cDNA6-V5His.

Generation of Tat-tagged G3BP1 B domain peptides. Three peptides were generated from the rat G3BP1 B domain sequence (amino acids 140-220; UniProt ID #D3ZYS7_RAT) by Bachem Americas, Inc. Peptides were synthesized with Nterminal dansyl chloride or FITC and N- or C-terminal HIV Tat peptide for cell permeability; the Tat sequence was placed at the least conserved end of the sequence based on P-BLAST of vertebrate G3BP1 sequences available in UniProt database. Peptide sequences were: 147-166, EESEEEVEEPEENQQSPEVV-YGNK-KNNQNNN [SEQ ID NO: 1]; 168-189, DDSGTFYDQTVSNDLEEHLEEP-YGNKKNNQNNN [SEQ ID NO: 3]; and 190-208, YGNKKNNNQNNN-VVE-PEPEPEPEPEPEPVSE [SEQ ID NO: 4]. Meanwhile, human G3BP1 peptide, NCBI Reference Sequence: NP_005745.1, is 189-209, EPVAEPEPDPEPEPEEEPVSE [SEQ ID NO: 2] and may be applied as a treatment method for patients as described herein.

Immunofluorescent staining. All procedures were performed at room temperature (RT) unless specified otherwise. Cultured neurons were fixed in 4% paraformaldehyde (PFA) in phosphate-buffered saline (PBS) and processed as described. Primary antibodies consisted of: rabbit anti-G3BP1 (1:200, Sigma), RT97 mouse anti-neurofilament (NF; 1:500, Devel. Studies Hybridoma Bank), goat anti-NRN1 (1:100, Novartis), rabbit anti-IMM (1:100, My Biosciences), rabbit anti-GAP43 (1:5000, Novus), and rabbit anti-G3BP1$^{S149}$ (1:300, Sigma). FITC conjugated donkey anti-rabbit and Cy3-conjugated donkey anti-mouse (both at 1:200, Jackson ImmunoRes.) were used as secondary antibodies.

For G3BP1 colocalization with SG and PB proteins, Zenon antibody labeling kit (Life Technologies) was used to directly label antibodies with fluorophores.

Combinations of rabbit anti-G3BP1 (Sigma)+Alexa-488, rabbit anti-HuR (Millipore)+Alexa-405, rabbit anti-FMRP (Cell Signaling Tech)+Alexa-555, and rabbit anti-FXR1 (a kind gift from Dr. Khancliah, Institut Universitaire en Santé Mentale de Quebec)+Alexa-633 or rabbit anti-G3BP1+Alexa-488, rabbit anti-DCP1A (Abcam)+Alexa-405, and rabbit anti-XRN1 (Bethyl Lab)+Alexa-633 were used at 1:50 dilution for each antibody. Equal amounts of rabbit-IgG labeled with Alexa-405, -488, -555 and -633 were used as control.

For quantifying axonal content of G3BP1, TIA1, and G3BP1$^{PS149}$ in peripheral nerve, sciatic nerve segments were fixed for 4 h in 4% PFA and then cryoprotected overnight in 30% sucrose, PBS at 4° C. 10 μm cryostat sections were processed for immunostaining as previously described. Primary antibodies consisted of rabbit anti-G3BP1 (1:100), rabbit anti-phospho-G3BP1$^{PS149}$ (1:100), and RT97 mouse anti-NF (1:300). Secondary antibodies were FITC-conjugated donkey anti-rabbit and Cy3-conjugated donkey anti-mouse (both at 1:200, Jackson ImmunoRes.).

Immunoblotting confirmed the specificity of the anti-G3BP1 and -G3BP1$^{PS149}$ antibodies and by immunofluorescence signals for both antibodies were decreased in DRGs transfected with siRNAs to G3BP1.

Paraffin sections were used for analyses of nerve regeneration. For this, 10 μm thick paraffin sections of sciatic nerve were deparaffinized in 100% xylene (2×10 min) followed by 100% ethanol (2×10 min). Sections were rehydrated by sequential incubations in 95, 75 and 50% ethanol for 5 min each, and then rinsed in deionized water. Sections were permeabilized in 0.3% Triton X-100 in PBS, and then rinsed in PBS for 20 min and equilibrated in 50 mM Tris [pH 7.4], 150 mM NaCl, 1% heat-shock bovine serum albumin (BSA), and 1% protease-free BSA (Roche) ('IF buffer'). Sections were then blocked in IF buffer plus 2% heat-shock BSA, and 2% fetal bovine serum for 1.5-2 h. After blocking, samples were incubated overnight at 4° C. in a humidified chamber with the primary antibodies in IF buffer. Samples were washed in IF buffer three times and then incubated with secondary antibodies diluted in IF buffer for 45 min. Samples were washed in IF buffer three times followed by a rinse in PBS and deionized water. Primary antibodies consisted of: RT97 mouse anti-NF (1:300) and rabbit anti-RFP (1:100, Rockland Immun. Chem.). The RFP antibody was confirmed to detect BFP by immunoblotting (see below) and immunolabeling of transfected DRG neurons (data not shown). Secondary antibodies were used as above.

All samples were mounted with Prolong Gold Antifade (Invitrogen) and analyzed by epifluorescent or confocal microscopy. Leica DMI6000 epifluorescent microscope with ORCA Flash ER CCD camera (Hamamatsu) or Leica SP8X confocal microscope with HyD detectors was used for imaging unless specified otherwise. For quantitation between samples, imaging parameters were matched for exposure, gain, offset and post-processing. For protein-protein colocalizations, HyVolution (Leica/Huygens) deconvolution was used to optimize optical resolution in confocal image stacks acquired with parameters optimized for this post-processing.

Fluorescence in-situ hybridization (FISH). For FISH, DRG cultures were fixed for 15 min in 2% PFA in PBS. RNA-protein colocalization was performed using custom 5' Cy3-labeled Stellaris' probes (probe sequences available upon request; BioSearch Tech.). Scrambled probes were used as control for specificity; samples processed without the addition of primary antibody were used as control for antibody specificity. Primary antibodies consisted of rabbit anti-G3BP1 (1:100) and RT97 mouse anti-NF (1:200). FITC-conjugated donkey anti-rabbit and Cy5-conjugated donkey anti-mouse (both at 1:200) were used as secondaries. Samples were mounted as above and analyzed using a Leica SP8X confocal microscope.

Samples were post-processed with HyVolution integrated into the Leica LAX software and analyzed as outlined below for RNA-protein colocalization.

Proximity ligation assay (PLA). PLA has been used to show protein colocalization within a range of approximately 40 nm. For this, the inventors used Duolink kit per the manufacturer's instructions (Sigma). Briefly, dissociated DRGs were cultured for 48 h, fixed with 4% PFA in PBS. Samples were blocked and permeabilized in PBS plus 0.1% Triton X-100, 5% donkey serum, 1% BSA for 30 min. Samples were incubated with the following primary antibodies overnight at 4° C. in PBS plus 1% donkey serum: rabbit anti-G3BP (1:100), mouse anti-HuR (1:100), and mouse anti-DCP1a (1:100). After washing in PBS, samples were incubated with PLA reagent±probes for 1 h at 37° C. Following three washes in 0.01 M Tris [pH 7.4], 0.15 M NaCl and 0.05% Tween 20 (buffer A'), ligation-ligase mix was applied and samples were incubated for 30 min at 37° C. Subsequently, samples were washed 2×in buffer A, then the amplification-polymerase mix was added and samples were incubated for 110 min at 37° C. Finally, coverslips were washed three times in 0.2 M Tris-Cl [pH 7.5], 0.1 M NaCl (buffer B') and then incubated with chicken anti-NF H antibody (1:2000; Abcam) for 45 min at RT. Coverslips were washed in buffer B three times, incubated for 45 min with Alexa 488-conjugated donkey anti-chicken (Jackson ImmunoRes., 1:1000), washed and mounted with Mowiol. PLA with only one of the two primary antibodies (but adding both PLA probes) was used as a technical control.

Imaging was performed using an Olympus FV1000 confocal microscope (60×/NA 1.35 UPLSAPO oil immersion objective). Only NFH positive neurites at >200 μm distances from the cell body were analyzed using Fiji software. Ostu thresholding was applied to generate a binary mask of the NFH signal, and PLA signal was then detected using the "Find Maxima . . . " function.

Fluorescence recovery after photobleaching (FRAP). FRAP was used to test for axonal mRNA protein synthesis using diffusion-limited GFP$^{MYR}$ and mCherry$^{MYR}$ reporters as described with minor modifications. In each case, DRG neurons were co-transfected with GFPMR 5'/3'nrn1+mCherry$^{MYR}$ 5'/3'gap43 or GFP$^{MYR}$ 5'/3' impβ1+mCherry$^{MYR}$ 5'/3'gap43 so that recovery of both reporters could be analyzed simultaneously. Cells were maintained at 37° C., 5% CO$_2$ during imaging sequences. 488 nm and 514 nm laser lines on Leica SP8X confocal microscope were used to bleach GFP and mCherry signals, respectively (Argon laser at 70% power, pulsed every 0.82 s for 80 frames). Pinhole was set to 3 Airy units to ensure full thickness bleaching and acquisition (63×/1.4 NA oil immersion objective). Prior to photobleaching, neurons were imaged every 60 s for 2 min to acquire baseline fluorescence the region of interest (ROI; 15% laser power, 498-530 nm for GFP and 565-597 nm for mCherry emissions, respectively). The same excitation and emission parameters were used to assess recovery over 15 min post-bleach with images acquired at 30 s intervals. To determine if fluorescence recovery in axons was from translation, cultures were treated with 150 μg/ml cycloheximide (Sigma) or 100 μm anisomycin (Sigma) for 30 min prior to photobleaching for GFP$^{MYR}$ 5'/3'nrn1+mCherry$^{MYR}$ 5'/3'gap43 and GFP$^{MYR}$ 5'/3'impβ1+mCh$^{MYR}$ 5'/3'gap43 transfected DRGs, respectively. For peptide treatments, G3BP1-mCh transfected DRG neurons were treated with 10 μM G3BP1 peptides after acquiring the baseline expression values. Photobleaching followed by analyses of recovery was performed after 30 min of peptide exposure.

For testing G3BP1 protein mobility in axons, DRG neurons were transfected with G3BP1$^{S149A}$-GFP or G3BP1$^{S149E}$-GFP and imaged as above but only the 488 nm laser was used for photobleaching (Argon laser at 70% power, pulsed every 0.82 s for 80 frames). Fluorescent intensities in the ROIs were calculated by the Leica LASX software.

For normalizing across experiments, fluorescence intensity value at t=0 min postbleach from each image sequence was set as 0%. The percentage of fluorescence recovery at each time point after photobleaching was then calculated by normalizing relative to the pre-bleach fluorescence intensity (set at 100%).

Live cell imaging for G3BP1-mCherry granules. DRG neurons were transfected with G3BP1-mCherry, and 36 h later distal axons were imaged using Leica SP8X confocal microscope with environmental chamber maintained at 37° C., 5% $CO_z$ (with 63×/1.4 NA oil immersion objective). G3BP1-mCherry signals were imaged as single optical planes in the axon shaft every 2 s for 100 frames (at 540 nm excitation and 23% white light laser power; 565-597 nm emission). To study the effect of the G3BP1 190-208 or 168-189 peptide, 10 μM FITC-conjugated peptide was added to the media and 15 min later imaging was continued.

For quantitation of G3BP1-mCherry aggregates density and size, a 100 μm of the axon shaft was considered (≥200 μm from cell body). Thresholding was applied to acquired image sequences using ImageJ to generate binary masks.

ImageJ particle analyzer was used for analysis. G3BP1 aggregates with area ≥1 μm$^2$ were considered as SG-like structures. For analyzing the G3BP1 aggregate velocity, ImageJ Trackmate plug-in was used.

Puromycinylation assay. To visualize newly synthesized proteins in cultured neurons, the inventors used the Click-iT® Plus OPP Protein Synthesis Assay Kit per manufacturer's instructions (Invitrogen/Life Technologies). Briefly, 3 DIV cultures were incubated with 20 μM$_o$-propargyl-puromycin (OPP) for 30 min at 37° C. OPP labeled proteins were detected by crosslinking with Alexa Fluor-594 picolyl azide molecule. Coverslips were then mounted with Prolong Gold Antifade (Invitrogen) and imaged with Leica DMI6000 epifluorescent microscope as above. ImageJ was used to quantify the Puromycinylation signals in distal axons and cell bodies.

Immunoblotting. For immunoblotting, protein lysates or immunoprecipitates were denatured by boiling in Laemmle sample buffer, fractionated by SDS-PAGE, and transferred to nitrocellulose membranes. Blots were blocked for 1 h at room temperature with 5% non-fat dry milk in Tris-buffered saline with 0.1% Tween 20 (TBST) for anti-tagBFP, -GAPDH and -G3BP1 antibodies; 5% BSA in TBST was used for blocking anti-G3BP1$^{PS149}$ antibody. Primary antibodies diluted in appropriate blocking buffer were added to the membranes and incubated overnight incubation at 4° C. with rocking. Primary antibodies consisted of: rabbit anti-G3BP1 (1:2000; Sigma), rabbit anti-G3BP1P$^{S149}$ (1:1000; Sigma), rabbit anti-TagBFP (1:2000; Evrogen), and rabbit anti-GAPDH (1; 2,000; CST). After washing in TBST, blots were incubated HRP-conjugated anti-rabbit IgG antibodies (1:5000; Jackson lab) diluted in blocking buffer for 1 h at room temperature. After washing signals were detected using ECL Prime™ (GE Healthcare).

Mass spectrometry by parallel reaction monitoring (PRM). Protein extraction was carried out according to the standard manufacturer's protocol using axoplasm samples suspended in 0.5 ml of TrIzol LS. Protein pellets were then reconstituted in urea, reduced, alkylated, digested with trypsin and desalted as previously described. PRM was performed using nano-Acquity UPLC system (Waters) online with Q Exactive Plus mass spectrometer (Thermo-Fisher). Digested peptides were loaded at 0.5 μg per sample and separated by low pH, two-buffer reverse phase chromatography on a 200 cm monolithic silica-C18 column (GL Sciences, Japan) over a 6 h gradient as previously described. Q Exactive Plus instrument was used in PRM mode with the following parameters: positive polarity, R=17,500 at 200 m/z, AGC target 1e6, maximum IT 190 ms, MSX count 1, isolation window 3.0 m/z, NCE 35%. Unique previously detected tryptic peptide DFFQSYGNVVELR [SEQ ID NO: 6] from rat G3BP1 (Uniprot ID D3ZYS7) was targeted (as part of a set of 184 target peptides from 84 proteins with possible roles in axonal mRNA transport; subject of a separate study). PRM data analysis was performed using Skyline v. 3.5.

RNA immunoprecipitation (RIP). HEK293T cells or DRG neurons were lysed in 100 mM KCl, 5 mM $MgCl_2$, 10 mM HEPES [pH 7.4], 1 mM DTT, and 0.5% NP-40 (RIP buffer) supplemented with 1×protease inhibitor cocktail (Roche) and RNasin Plus (Invitrogen). Cells were passed through 25 Ga needle 5-7 times and cleared by centrifugation at 12,000×g for 20 min. Cleared lysates were pre-absorbed with Protein A-Dynabeads (Invitrogen) for 30 min. Supernatants were then incubated with primary antibodies for 3 h and then immunocomplexes precipitated with Protein G-Dynabeads (Invitrogen) for additional 2 h at 4° C. with rotation. Mouse anti-G3BP1 (5 μg, BD Biosciences) and rabbit anti-GFP (5 μg, Abcam) antibodies were used for immunoprecipitation. Beads were washed six times with cold RIP buffer. Bound RNAs were purified and analyzed by RTddPCR (see below).

RNA isolation and PCR analyses. RNA was isolated from immunoprecipitates and cultures using the RNeasy Microisolation kit (Qiagen). Fluorimetry with Ribogreen (Invitrogen) was used for RNA quantification. For analyses of total RNA levels and inputs for RIP analyses, RNA yields were normalized across samples prior to reverse transcription using Sensifast (Bioline). For RIP assays, an equal proportion of each RIP was used for reverse transcription with Sensifast. ddPCR products were detected using Evagreen or Taqman primer and probe sets (Biorad or Integrated DNA Tech; sequences available on request) and QX200™ droplet reader (Biorad). In GFP RIP experiment, B domain-BFP expression consistently increased G3BP1-GFP levels in the DRG neurons. So the level of mRNA precipitating with G3BP1-GFP was normalized to the G3BP1-GFP signals from immunoblotting across each sample in each experiment.

Assessment of muscle reinnervation. AAV5 encoding GFP or B domain-BFP was injected into the sciatic nerve near the sciatic nerve notch (left and right nerves, respectively). 7 d post-virus injections, bilateral sciatic nerve crushes were performed at mid-thigh level. The extent of innervation of the LG and TA muscles was evaluated using in vivo electromyography (EMG). For this, animals were anesthetized by IP injection with Ketamine HCl (80 mg/kg, Hospira) and AnaSed (10 mg/kg, LLOYD Laboratories) to achieve a surgical plane of general anesthesia; additional IP injections of Ketamine HCl (40 mg/kg) were given to maintain this plane throughout the experiment.

Bipolar fine wire EMG electrodes were constructed from insulated nickel alloy wire (California Fine Wire, Stablohm 800). The insulation over the distal 1 mm of the tips was removed by scraping with a scalpel blade and the tips of the two wires were staggered by 1 mm. Electrodes were then placed into the lateral head of LG and the mid-belly of the TA muscles using a 25 Ga hypodermic needle. Once in place, the needle was removed and the wires were connected to the differential amplifiers. To stimulate the sciatic nerve, a small skin incision was made just inferior to the ischial tuberosity, exposing the sciatic nerve as it coursed between the gluteal and hamstring muscles, proximal to the crush injury site. A small rectangle of Paraffinc) was wrapped loosely around the nerve and pierced by two unipolar needle electrodes (Neuroline monopolar, 28 G, Ambu/AS). The tips of the two needle electrodes were separated from each other by approximately 1 mm.

Lead wires from the needles were connected to an optically isolated constant voltage stimulator under computer control.

Evoked EMG activity from LG and TA was then recorded after sciatic nerve stimulation. Stimulation and recording were controlled by a laboratory computer system running custom software written in Labview®. Ongoing EMG activity in the LG was sampled at 10 kHz; when the rectified and integrated voltage over a 20 ms period fell within a user-defined range, a 0.3 ms duration stimulus pulse was delivered to the nerve via the needle electrodes. Muscle activity was sampled from 20 ms prior to the stimulus until 100 ms after the stimulus and recorded to disc.

Stimuli were delivered no more frequently than once every 3 s to avoid fatigue. A range of stimulus intensities was applied in each experiment to sample evoked muscle activity from sub-threshold to supramaximal. In a typical experiment approximately 200 stimulus presentations were studied. At the end of each experiment, all electrodes were removed and the skin incisions closed with sutures.

The recorded compound muscle action potentials (M waves) in LG and TA evoked by sciatic nerve stimulation were analyzed off-line. The amplitude of the evoked M waves was measured as the average rectified voltage within a defined time window after the stimulus application. In intact anesthetized animals, this window is 0.5-2.0 ms, as described. After nerve crush, M waves evoked from sciatic nerve stimulation are, by definition, generated by reinnervated muscle fibers.

The latency and duration of these potentials are longer than those found in intact animals. Thus, the time window used to measure the amplitude of the M waves was adjusted to accommodate this change. Recordings were made from intact animals, immediately following and 1, 2, 4, 6, and 8 wk after nerve crush. At each time point, the amplitude of the largest evoked M wave (Mmax) was determined and scaled to Mmaxrecorded from that animal prior to nerve crush. Means of these scaled responses recorded from muscles in which motor neurons were induced to express B domain-BFP and those in which motor neurons expressed only GFP were compared at each time studied.

Image analyses and processing. For protein-protein and protein-mRNA colocalization, xyz image sequences captured 100 μm segments of the axon shaft (separated from the cell body and growth cone by ≥200 μm) were deconvolved using Huygens HyVolution software. Colocalization was analyzed using ImageJ JACoP plug-in—imagej nih gov ij plugins track jacop—to calculate Pearson's coefficient. These coefficient calculations were independently validated with Volocity software (Perkin Elmer).

For analyses of protein levels in tissues, z planes of the xyz tile scans from 3-5 locations along each nerve section were analyzed using ImageJ. Colocalization plug-in was used to extract protein signals that overlap with axonal marker (NF) in each plane, with the extracted 'axon-only' signal projected as a separate channel.

For calculating axonal G3BP1 aggregate and G3BP1$^{PS149}$ signal intensities, absolute signal intensity was quantified in each xy plane of the 'Colocalization' extracted images for axonal only G3BP1 and G3BP1$^{PS149}$ using ImageJ. Protein signal intensities across the individual xy planes were then normalized to NF immunoreactivity area. The relative protein signal intensity was averaged for all image locations in each biological replicate.

For neurite outgrowth, images from 60 h DRG cultures were analyzed for neurite outgrowth using WIS-Neuromath. Axon morphology was visualized using GFP and/or NF immunofluorescence as described. Differentiated hiPSC neuron image acquisition and neurite length quantification was performed using Arrayscan XTI (Thermo Fisher).

To assess regeneration in vivo, tile scans of NF-stained nerve sections were post-processed by Straighten plug-in for ImageJ—imagej nih gov ij—. NF positive axon profiles were then counted in 30 μm bins at 0.3 mm intervals distal from crush site. Number of axon profiles present in the proximal crush site was treated as the baseline, and values from the distal bins were normalized to this to calculate the percentage of regenerating axons.

Statistical analyses. Kaleidagraph (Synergy), Prism (GraphPad), and Excel (Microsoft) software packages were used for statistical analyses. One-way ANOVA was used to compare means of independent groups and Student's t-test was used to compare smaller sample sizes of the in vivo analyses. p values of ≤0.05 were considered as statistically significant. For statistical analyses of Pearson's coefficients, Fishers Z-transformation was used to compare: G3BP1+ HuR, FXR1, and FMRP colocalization versus DCP1a+ XRN1 coefficients and G3BP1+DCP1a and XRN1 versus DCP1a+XRN1 coefficients.

The current disclosure provides evidence that blocking stress granule aggregation by treatment with cell permeable G3BP1 190-208 peptide effectively prevents MPP$^+$-induced (PD model) and A3-mediated neurotoxicity (AD model), as well as prevents protein aggregation associated with expression of mutant TIA1 and TDP43 proteins that cause ALS. Here, we provide data indicating that the cell permeable G3BP1 190-208 peptide not only triggers disassembly of pre-existing stress granule protein aggregates in these neurodegenerative disease models, but also effectively blocks neurodegenerative disease associated axon degeneration.

Cell permeable G3BP1 190-208 peptide prevents neurodegeneration-associated aggregation of endogenous stress granule protein in axons.

The current disclosure first tested whether treatment of E18 cortical or midbrain neurons with neurotoxins Aβ and MPP$^+$, respectively, induces protein aggregations of endogenous stress granule and neurodegeneration-associated proteins preceding axon degeneration and cell death. For cortical neurons, a 6-hour exposure to 1 μM Aβ oligomer significantly increased aggregate size for the stress granule proteins G3BP1, TIA1, FMRP and FXR as well as the ALSand FTD-associated proteins TDP43 and FUS-TLS along axons (see FIGS. 13A, 13B, 13C, and 13D).

Figure 13A:
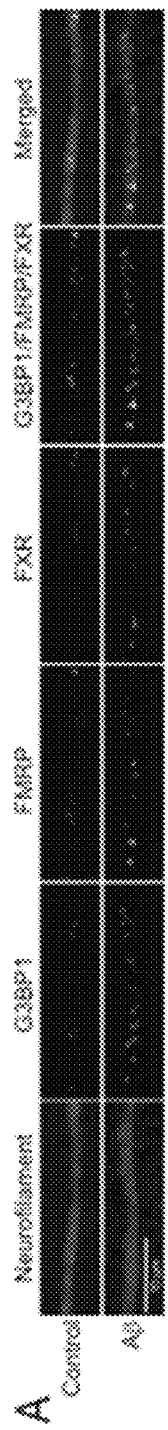
FIG. 13A shows representative conlocal images for G3BP1 (magenta), FMRP (green), FXR (red) and neurofilament (blue) immunoreactivity along axons for E18 cortical neuron cultures (7 DIV)±1 μM Aβ oligomer for 6 hours.
Figure 13B:
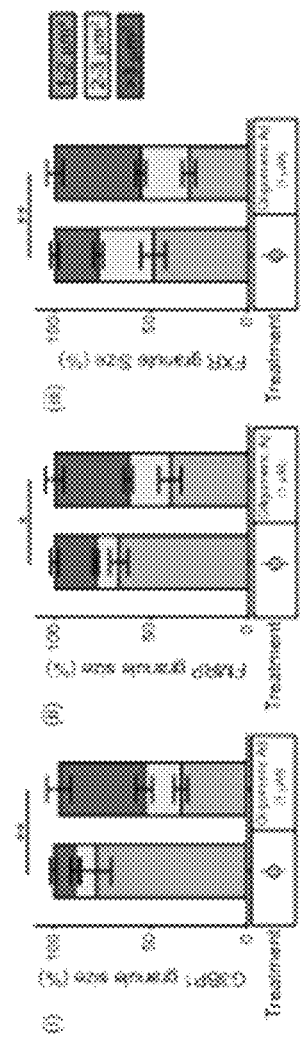
FIG. 13B shows the size distribution for aggregates of G3BP1 (i), RIP (ii) awl FXR (iii) along control vs. A13 oligomer treated axons as in FIG. 13A.
Figure 13C:
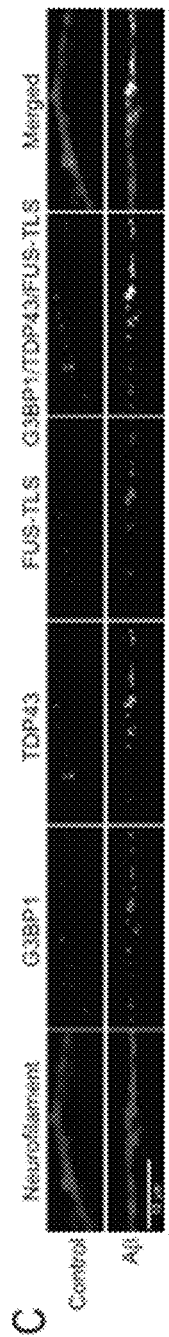
FIG. 13C shows confocal images for G3BP1 (magenta), FUS-TLS (green), TDP43 (red) and neurofilament (blue) immunoreactivity along axons for cortical neurons treated as in FIG. 13A.
Figure 13D:
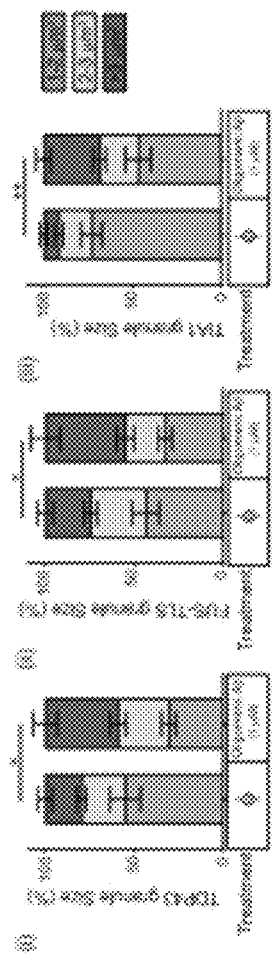
FIG. 13D shows the size distribution for TDP43 (i), FUS-TLS (ii), TIA1 (iii) aggregates along control vs. Aβ oligomer-treated axons as in FIG. 13C.
Figure 13E:
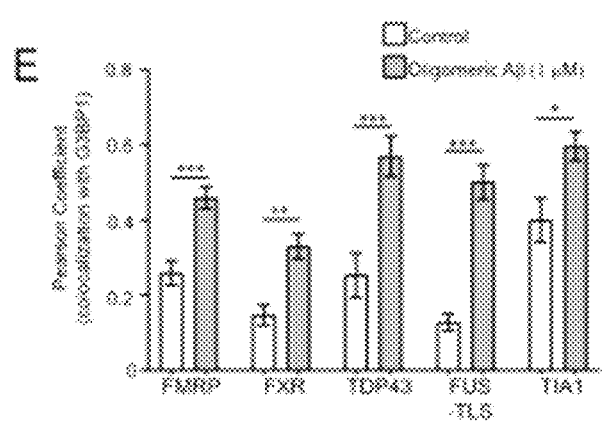
FIG. 13E shows quantification for colocalization of FMRP, FXR, TDP43, FUS-TLS and TIA1 with G3BP1 in axons of E18 cortical neurons treated as in 13A shown as average Pears coefficient±SEM.
Figure 13F:
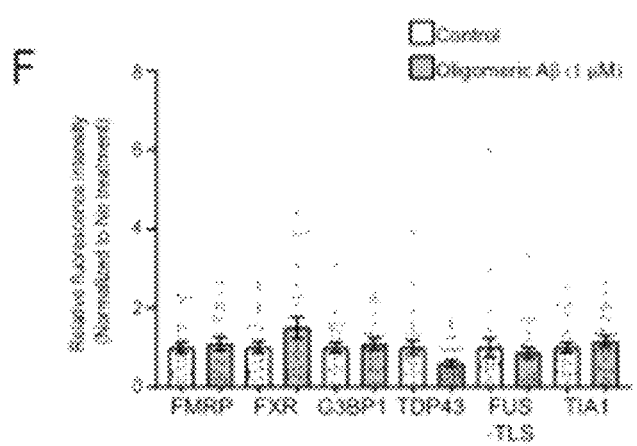
FIG. 13F shows the overall levels of these proteins based in exposure matched images (N≥1.00 aggregates over three repetitions and *p≤0.01, p≤0.005, *p≤0.001 for entire population distributions by Fishers exact test for B and D; N≥25 neurons over 3 repetitions and *p≤0.01, p≤0.005, *p≤0.001 by one-way ANOVA with Tukey HSD post-hoc for FIGS. 13E-13F).

FIGS. 13A-13F show Amyloid beta oligomer treatment increases in RNA binding protein aggregation. FIGS. 13A and 13B show representative confocal images for G3BP1 (magenta), FMRP (green), FXR (red) and neurofilament (blue) immunoreactivity along axons for E18 cortical neuron cultures (7 WV)±1 µM Aβ oligomer for 6 hours are shown in FIG. 13A. FIG. 13B shows the size distribution for aggregates of G3BP1 (i), (ii) and FXR (iii) along control vs. Aβ oligomer treated axons as in 13A. FIGS. 13C and 13D show representative confocal images for G3BP1 (magenta), FUS-TLS (green), TDP43 (red) and neurofilament (blue) immunoreactivity along axons for cortical neurons treated as in A are shown in FIG. 13C. FIG. 13D shows the size distribution for TDP43 (i). FUS-TLS (ii). TIA1 (iii) aggregates along control vs. AP oligomer-treated axons as in 13G. FIGS. 13E and 13F show quantification for colocalization of FMRP, FXR, TDP43, FUS-TLS and TIM with G3BP1 in axons of E18 cortical neurons treated as in A shown as average Pearson's coefficient±SEM shown in FIG. 1:3E. FIG. 13F shows the overall levels of these proteins based in exposure matched images (N≥100 aggregates over three repetitions and *p≤0.01, p≤0.005, *p≤0.001 for entire population distributions by Fishers exact test fir B and D; N≥25 neurons over 3 repetitions and *p≤0.01, p≤0.005, *p≤0.001 by one-way ANOVA with Tukey HSD post-hoe for FIG. 13E and FIG. 13F).

This treatment duration is well before we observe axon degeneration and cell death, so this is a 'pre-neurodegeneration' response to A6 peptide. The A6 peptide treatment also significantly increased colocalization of TIA1, FMRP, FXR, TDP43 and FUS-TLS with G3BP1 aggregates with no overall change in the levels of these proteins (FIGS. 13E-13F). In midbrain neurons, MPP+ treatment for 6 hours also significantly increases the aggregate sizes for G3BP1, TIA1, FMRP, FXR, TDP43 and FUS-TLS aggregates along axons (FIGS. 14A-14D). Similar to Aβ results above, this MPP+ treatment duration is well before we observe axon degeneration and cell death, so this is a 'pre-neurodegeneration' response to the neurotoxin MPP+. Also, MPP+ treatment causes a significant increase in TIA1, FMRP, FXR, TDP43 and FUS-TLS colocalization with G3BP1 without any change in overall levels for any of these proteins (FIG. 14E-14F). These data point to aggregation of stress granule and neurodegeneration-associated RNA binding proteins as a pathophysiological event shared between different neurodegeneration-associated stressors.

Figure 14A:
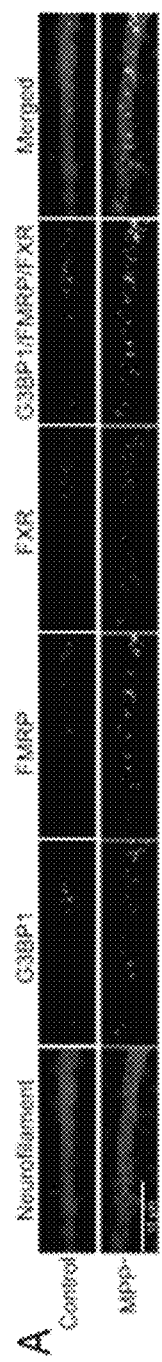
FIG. 14A shows confocal images for G3BP1 (magenta), FMRP (green), FXR (red) and neurofilament (blue) it immunoreactivity along axons for E18 midbrain neuron cultures (7 DIV)±100 μM MPP+ for 6 hours.
Figure 14B:
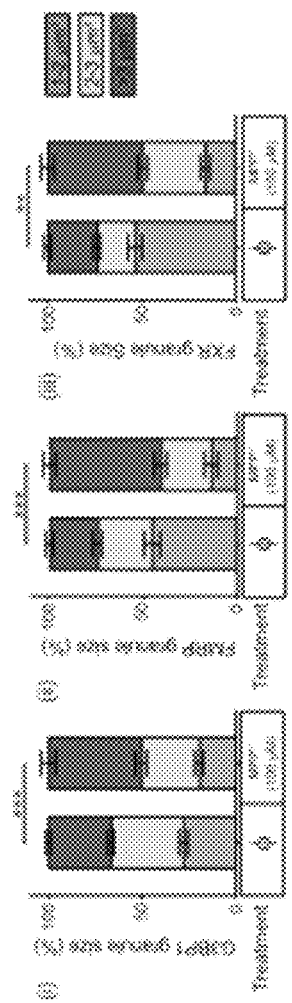
FIG. 14B shows the size distribution for aggregates of G3BP1 (i), FMRP (ii) and FXR (iii) along control vs. MPP$^+$-treated axons.
Figure 14C:
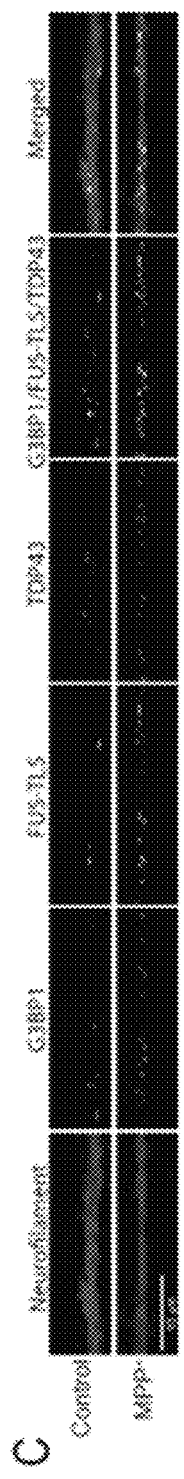
FIG. 14C shows representative confocal images for G3BP1 (magenta), FUS-TLS (green), TDP43 (red) and neurofilament (blue) immunoreactivity along axons for midbrain neurons treated as in FIG. 13A.
Figure 14D:
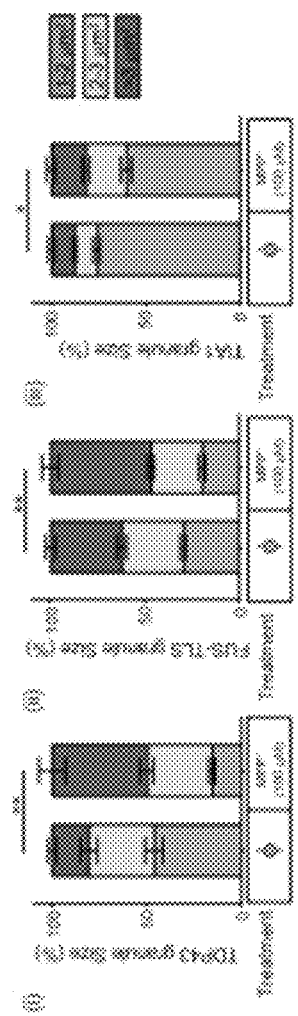
FIG. 14D shows the size distribution for TDP43 (i), FUS-TLS (ii), TIA1 (iii) aggregates along control vs. MPP$^+$-treated axons as in FIG. 14C.
Figure 14E:
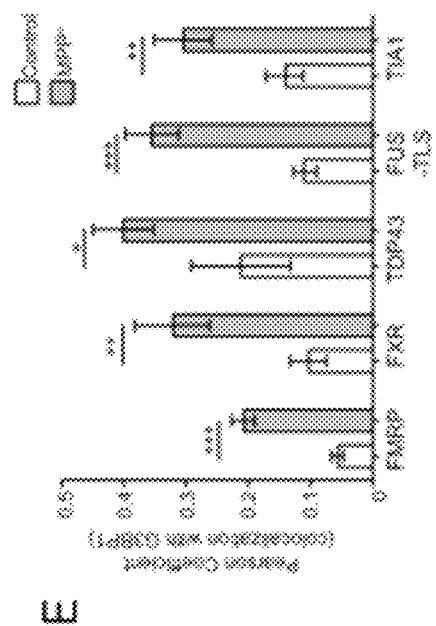
FIG. 14E shows quantifications for colocalization of FMRP, FXR, TDP43, FUS-TLS and TIA1 with G3BP1 in axons of E18 midbrain neurons treated as in A are shown as average Pearson's coefficient±SEM.
Figure 14F:
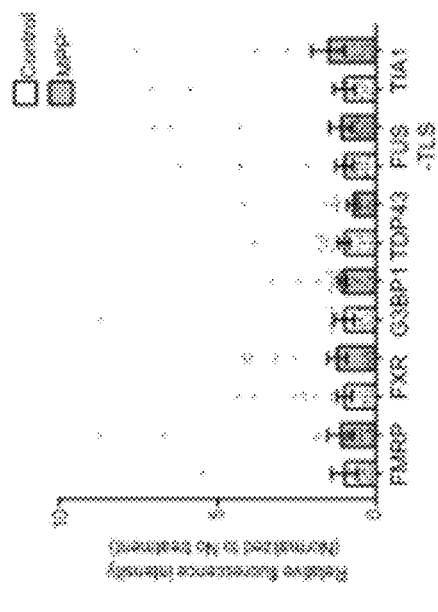

FIGS. 14A-14F show PD-causing MPP+ increases RNA binding protein aggregation. Representative confocal images for (ABM (magenta), FMRP (green), FXR (red) and neurofilament (blue) immunoreactivity along axons for E18 midbrain neuron cultures (7 DIV)±100 µM MPP+ for 6 hours are shown in FIG. 14A, FIG. 14B shows the size distribution for aggregates of G3BP1 FMRP (ii) and FXR (iii) along control vs. MPP+-treated axons as in A. Representative confocal images for G3BP1 (magenta), FUS-TLS (green), TDP43 (red) and neurofilament (blue) immunoreactivity along axons for midbrain neurons treated as A are shown in FIG. 14C, FIG. 14D shows the size distribution for TDP43 (i), FUS-TLS TIA1 (iii) aggregates along control vs. MPP+-treated axons as in FIG. 14C. Quantifications for colocalization of FMRP, FXR, TDP43, FUS-TLS and TIA1 with G3BP1 in axons of E18 midbrain neurons treated as in FIG. 14A are shown as average Pearson's coefficient±SEM shown in FIG. 14E. FIG. 14F shows the overall levels of these proteins based in exposure matched images (N≥100 aggregates over three repetitions and *p≤0.01, p≤0.005, *p≤0.001 for entire population distributions by Fishers exact test for FIG. 14B and FIG. 14D; N≥25 neurons over 3 repetitions and *p≤0.01, p≤0.005, *p≤0.001 by one-way ANOVA with Tukey HSD post-hoc for FIGS. 14E-14F).

The data in FIGS. 13A-F and 14A-F raise the possibility that stress granule targeting therapies like the cell permeable G3BP1 190-208 peptide may decrease or even prevent loss of neurons across different types of neurodegenerative diseases. To address this possibility, the current disclosure asked if the cell permeable G3BP1 190-208 peptide could disassemble pathological protein aggregates in neurons. For this, 7 day cortical neuron cultures were treated with 1 µM Aβ oligomer for 2 hours and then treated with cell permeable G3BP1 190-208 peptide or a scramble sequence cell permeable peptide for an additional 4 hours. As above, the Aβ oligomer treated cultures showed a significantly increased size of G3BP1, TIA1, FMRP, FXR, TDP43 and FUS-TLS aggregates along axons (FIGS. 15A-15D). Cell permeable G3BP1 190-208 peptide significantly decreased size of these aggregates (FIGS. 15A-15D) and TIA1, FMRP, FXR, TDP43 and FUS-TLS colocalization with G3BP1 compared to Aβ without peptide treatment as well as Aβ plus the scrambled peptide control (see FIG. 15E). Thus, the cell permeable G3BP1 190-208 peptide can not only prevent RNA binding protein aggregation in axons after exposure to neurotoxins associated AD and PD, but it can also trigger disassembly of these pathological aggregates after they begin to form.

Figure 15A:
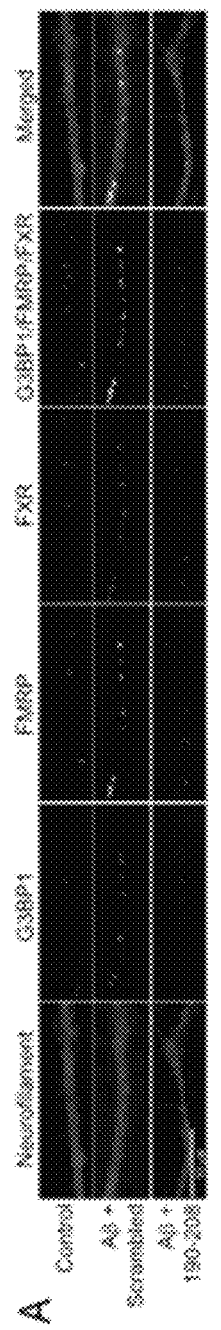
FIG. 15A shows confocal images for G3BP1 (magenta), FMRP (green), FXR (red) and neurofilament (blue) immunoreactivity along axons for control and 1 μM Aβ oligomer-treated E18 cortical neurons (7 DIV)±cell permeable G3BP1 190-208 peptide.
Figure 15B:
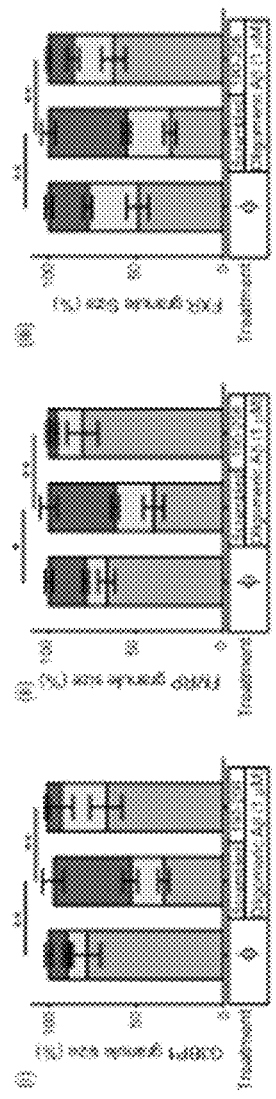
FIG. 15B shows the size distribution for aggregates of G3BP1 (i), FMRP (ii) and FXR (iii) along control vs. Aβ-treated axons and Aβ treated+G3BP1 190-208 or cell permeable peptide with scrambled sequence.
Figure 15C:
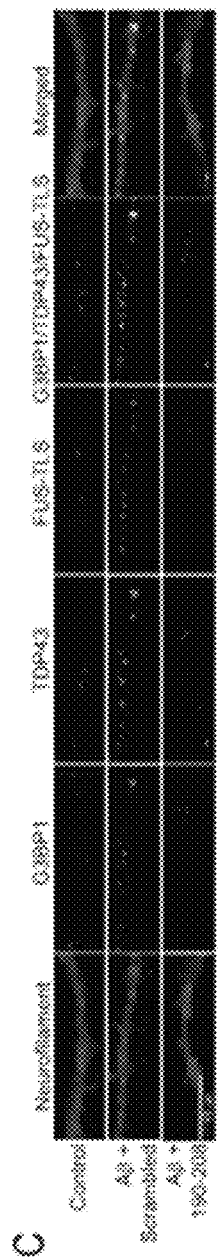
FIG. 15C confocal images for G3BP1 (magenta), FUS-TL (green), TDP43 (red) and neurofilament (blue) immunoreactivity along axons for cortical neurons treated as in A.
Figure 15D:
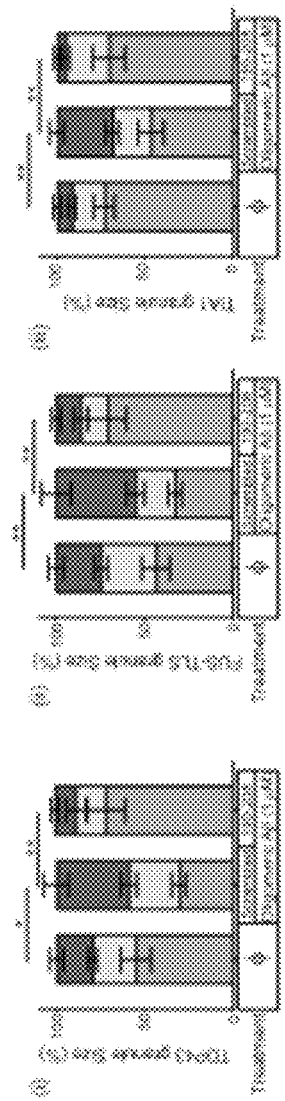
FIG. 15D shows the size distribution for TDP43 (i), FUS-TLS (ii), TIA1 (iii) aggregates along axons of control vs. Aβ-treated and Aβ treated+G3BP1 190-208 or cell permeable peptide with scrambled sequence.
Figure 15E:
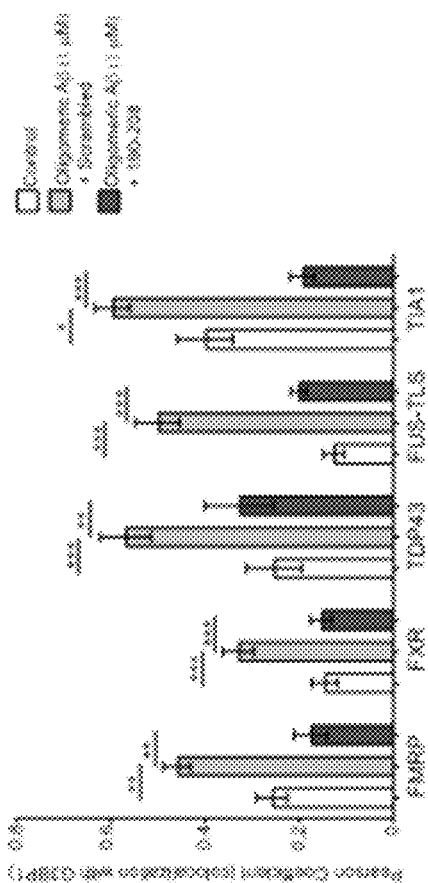
FIG. 15E quantifications for colocalization of FMRP, FXR, TDP43, FUS-TLS and TIA1 with G3BP1 in axons of E18 cortical neurons treated as in C are shown as average Pearson's coefficient±SEM (N≥120 aggregates over three repetitions and *p≤0.01, p≤0.005, *p≤0.001 for entire population distributions by Fishers exact test for B and D; A≥25 neurons over 3 repetitions and *p≤0.01, p≤0.005, *p≤0.001 by one-way ANOVA with Tukey HSD post-hoc for E).

FIGS. 15A-15E show reduction in am loid beta treatment dependent G3BP1-associated protein aggregates by addition of CB3BP1 190-208 peptide. Representative confocal images for G3BP1 (magenta) FMRP (green), FXR, (red) and neurofilament (blue) immunoreactivity along axons for control 1 µM Aβ oligomer-treated. E18 cortical neurons (7 DIV)±cell per cable G3BP1 190-208 peptide are shown in FIG. 15A. FIG. 15B shows the size distribution for aggregates of G3BP1 (i). FMRP (ii) and FXR (iii) along control vs. Aβ-treated axons and Aβ treated G3BP1 190-208 or cell permeable peptide with scrambled sequence. Representative confocal images for G3BP1 (magenta), FUS-TLS (green), TDP43 (red) and neurofilament (blue) immunoreactivity along axons for cortical neurons treated as in FIG. 15A are shown in FIG. 15G. FIG. 15 D shows the size distribution for TDP43 (i), FUS-TLS (ii), TIA1 (iii) aggregates along axons of control vs. Aβ-treated and Aβ treated+G3BP1 190-208 or cell permeable peptide with scrambled sequence. Quantifications for colocalization of FMRP, FXR, TDP43, FUS-TLS and TIA1 with G3BP1 in axons of E18 cortical neurons treated as in C are shown as average Pearson's coefficient SEM (N≥120 aggregates over three repetitions and *p≤0.01, p≤0.005, *p≤0.001 for entire population distributions by Fishers exact test for FIG. 15B and FIG. 15D: N≥25 neurons over 3 repetitions and *p≤0.01. p≤0.005, *p≤0.001 by one-way ANOVA with Tukey HSD post-hoc for FIG. 15E).

Figure 16A:
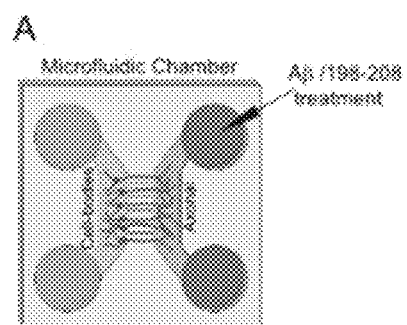
FIG. 16A shows schematic of the microfluidic culture set up. E18 cortical neurons were plated into the cell-body compartment (blue); after 7 DIV axons from these neurons extend through the microchannels into the axon compartment (pink).
Figure 16B:
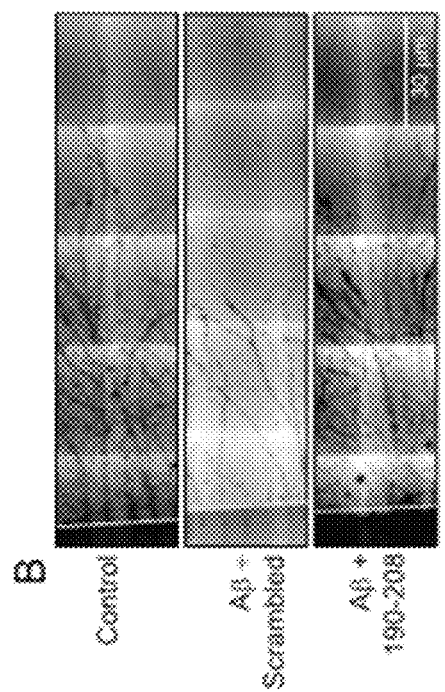
FIG. 16B shows representative montage images of axonal compartment of DIV7 E18 cortical neurons stained with neurofilament for control and Aβ oligomer (1 μM for 16 hours)±190-208 G3BP1 peptide (1 μM).
Figure 16C:
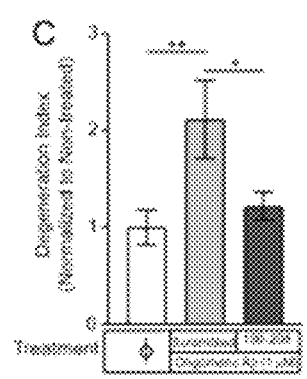
FIG. 16C shows quantitation of degeneration indices for cultures from B (N=3 repetitions and *p≤0.01, **p≤0.005 by one-way ANOVA with Tukey HSD post-hoc).

Cell permeable G3BP1 190-208 peptide prevents neurotoxin-induced axon degeneration through localized mechanisms. Axonal degeneration is thought to precede neuron death (and hence, neurodegeneration) in several neurodegenerative diseases including AD, PD and ALS. To test whether the cell permeable G3BP1 190-208 peptide protects against this early axonal degeneration, the current disclosure exposed only the axons of E18 cortical neuron cultures to Aβ peptide using microfluidic cultures (FIG. 16A). Axons exposed to Aβ oligomer showed axon degeneration at 16 hours (FIG. 16B-16C). Treating the axons with the cell permeable G3BP1 190-208 peptide near completely prevented this axon degeneration (FIG. 4B-C). Thus, the cell permeable G3BP1 190-208 peptide protects axons from the neurotoxic effects of Aβ oligomers through axon intrinsic mechanisms.

FIGS. 16A-16C show cell permeable G3BP1 190-208 peptide rescues amyloid beta oligomer-mediated axonal degeneration. FIG. 16A shows a schematic of the microfluidic culture set up. E18 cortical neurons were plated into the cell-body compartment (blue); after 7 DIV axons from these neurons extend through the microchannels into the axon compartment (pink) FIG. 16B shows representative montage images of axonal compartment of DIV7 E18 cortical neurons stained with neurofilament for control and Aβ oligomer (1 µM for 16 hours)±190-208 G3BP1 peptide (1 µM). Yellow line indicates the exit of the axons from the microchannels. FIG. 16C shows quantitation of degeneration indices for cultures from B (N=3 repetitions and *p≤0.01, **p≤0.005 by one-way ANOVA with Tukey HSD post-hoc).

Together, these data indicate that exposure of neurons to toxins known to be causative for AD and symptoms associated with PD trigger aggregation of RNA binding proteins associated with stress granules (G3BP1, TIA1, FMRP, and FXR) and are mutated in ALS (TDP43 and FUS-TLS). The cell permeable G3BP1 190-208 peptide that is the subject of this application disassembles these protein aggregates along axons and prevents axonal degeneration. These findings support our application for use of G3BP1, of between 19-21 peptides, such as rattus 190-208 or *Homo sapiens* 189-209 peptide, as a prophylactic and/or treatment method for neurodegenerative disorders.

All patents, patent applications, published applications, and publications, databases, websites and other published materials referred to throughout the entire disclosure herein, unless noted otherwise, are incorporated herein by reference in their entirety.

SEQUENCE LISTING—USC 2033101.000176

<110> University of South Carolina
<120> Targeting G3BP Aggregation To Prevent Neurodegeneration
<130> 2033101.0000176
<140> Ser. No. 16/881,096
<141> 2020 May 22
<150> U.S. Provisional Application No. 62/876,852
<151> 2019 Jul. 22
<160> 4
<170> PatentIn Version 3.5
<210> 1
<211> 31
<212> PRT
<213> Rattus norvegicus
<400> 1
Glu Glu Ser Glu Glu Glu Val Glu Glu Pro Glu Glu Asn Gln Gln Ser
1 5 10 15
Pro Glu Val Val Tyr Gly Asn Lys Lys Asn Asn Gln Asn Asn
20 25 30
<210> 2
<211> 21
<212> PRT
<213> *Homo sapiens*
<400> 2
Glu Pro Val Ala Glu Pro Glu Pro Asp Pro Glu Pro Glu Pro Glu Glu
1 5 10 15
Glu Pro Val Ser Glu
20
<210> 3
<211> 33
<212> PRT
<213> Rattus norvegicus
<400> 3
Asp Asp Ser Gly Thr Phe Tyr Asp Gln Thr Val Ser Asn Asp Leu Glu
1 5 10 15
Glu His Leu Glu Glu Pro Tyr Gly Asn Lys Lys Asn Asn Gln Asn Asn
20 25 30
Asn
<210> 4
<211> 31
<212> PRT
<213> Rattus Norvegicus
<400> 4
Tyr Gly Asn Lys Lys Asn Asn Asn Gln Asn Asn Asn Val Val Glu Pro
1 5 10 15
Glu Pro Glu Pro Glu Pro Glu Pro Glu Pro Glu Pro Val Ser Glu
20 25 30
<210> 5
<211> 16
<212> PRT
<213> Rattus Norvegicus
<400> 5
Cys Cys Ala Cys Ala Ala Gly Gly Ala Gly Cys Gly Gly Gly Ala Ala
1 5 10 15
210> 6
<211> 13
<212> PRT
<213> Rattus Norvegicus
<400> 6
Asp Phe Phe Gln Ser Tyr Gly Asn Val Val Glu Leu Arg
1 5 10

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

SEQUENCE LISTING

<160> NUMBER OF SEQ ID NOS: 7

<210> SEQ ID NO 1
<211> LENGTH: 31
<212> TYPE: PRT
<213> ORGANISM: Rattus norvegicus

<400> SEQUENCE: 1

Glu Glu Ser Glu Glu Val Glu Glu Pro Glu Glu Asn Gln Gln Ser
1               5                   10                  15

Pro Glu Val Val Tyr Gly Asn Lys Lys Asn Asn Gln Asn Asn Asn
                20                  25                  30

<210> SEQ ID NO 2
<211> LENGTH: 21
<212> TYPE: PRT
<213> ORGANISM: Homo sapiens

<400> SEQUENCE: 2

Glu Pro Val Ala Glu Pro Glu Pro Asp Pro Glu Pro Glu Pro Glu
1               5                   10                  15

Glu Pro Val Ser Glu
                20

<210> SEQ ID NO 3
<211> LENGTH: 33
<212> TYPE: PRT
<213> ORGANISM: Rattus norvegicus

<400> SEQUENCE: 3

Asp Asp Ser Gly Thr Phe Tyr Asp Gln Thr Val Ser Asn Asp Leu Glu
1               5                   10                  15

Glu His Leu Glu Glu Pro Tyr Gly Asn Lys Lys Asn Asn Gln Asn Asn
                20                  25                  30

Asn

<210> SEQ ID NO 4
<211> LENGTH: 31
<212> TYPE: PRT
<213> ORGANISM: Rattus norvegicus

<400> SEQUENCE: 4

Tyr Gly Asn Lys Lys Asn Asn Asn Gln Asn Asn Asn Val Val Glu Pro
1               5                   10                  15

Glu Pro Glu Pro Glu Pro Glu Pro Glu Pro Glu Pro Val Ser Glu
                20                  25                  30

<210> SEQ ID NO 5
<211> LENGTH: 16
<212> TYPE: PRT
<213> ORGANISM: Rattus norvegicus

<400> SEQUENCE: 5

Cys Cys Ala Cys Ala Ala Gly Gly Ala Gly Cys Gly Gly Gly Ala Ala
1               5                   10                  15

<210> SEQ ID NO 6
<211> LENGTH: 13
<212> TYPE: PRT
<213> ORGANISM: Rattus norvegicus

<400> SEQUENCE: 6

```
Asp Phe Phe Gln Ser Tyr Gly Asn Val Val Glu Leu Arg
1               5                   10
```

```
<210> SEQ ID NO 7
<211> LENGTH: 21
<212> TYPE: RNA
<213> ORGANISM: Homo sapiens

<400> SEQUENCE: 7
ccacauagga gcugggaauu u                                    21
```

What is claimed is:

1. A prophylactic method for blocking stress granule aggregation comprising:
    treating at least one cortical neuron cell with a cell permeable polypeptide to reduce neurodegeneration of the at least one cortical neuron cell thereby preventing induced and mediated neurotoxicity via blocking stress granule aggregation by treatment with the cell permeable polypeptide;
    wherein the cell permeable polypeptide disassembles aggregates of stress granules and neurodegeneration-associated RNA binding proteins along axons; and
    wherein the cell permeable polypeptide is a G3BP1 peptide comprising between 19-21 amino acids.

2. The method of claim 1, wherein the cell permeable polypeptide has the amino acid sequence of SEQ ID NO: 2.

3. The method of claim 1, wherein the induced neurotoxicity being treated comprises MPP+ induced neurotoxicity.

4. The method of claim 1, wherein the mediated neurotoxicity being treated comprises Aβ-mediated neurotoxicity.

5. The method of claim 1, wherein the aggregates of stress granule and neurodegeneration-associated RNA binding proteins arise as a pathophysiological event shared between different neurodegeneration-associated stressors in a subject with a neurogenerative disease.

6. The method of claim 5, wherein the neurodegeneration-associated stressor induces Parkinson's Disease, Alzheimer's Disease, Frontotemporal Dementia or Amyotrophic Lateral Sclerosis.

7. The method of claim 1, wherein administering the G3BP1 peptide comprising between 19-21 amino acids also decreases or prevents loss of cortical neurons via blocking stress granule aggregation.

8. The method of claim 1, wherein the stress granules being blocked comprise G3BP1, TIA1, FMRP, FXR, TDP43 and/or FUS-TLS.

9. A prophylactic method for blocking neurodegeneration disease associated with axon degeneration comprising:
    administering a cell permeable polypeptide to at least one cortical neuron cell in a subject with or without a neurodegenerative disease;
    wherein administration of the cell permeable peptide disassembles pathological protein aggregates in cortical neurons cells;
    wherein administration of the cell permeable peptide also prevents RNA binding protein aggregation in axons after exposure to neurotoxins; and
    wherein the cell permeable polypeptide is a G3BP1 peptide comprising between 19-21 amino acids.

10. The method of claim 9, wherein the cell permeable polypeptide comprises the amino acid sequence of SEQ ID NO: 2.

11. The method of claim 9, wherein the pathological protein aggregates and/or RNA binding protein aggregation arise as a pathophysiological event shared between different neurodegeneration-associated stressors in a subject with a neurogenerative disease.

12. The method of claim 11, wherein the neurodegeneration-associated stressor induces Parkinson's Disease, Alzheimer's Disease, Frontotemporal Dementia or Amyotrophic Lateral Sclerosis.

13. The method of claim 9, wherein administering the G3BP1 peptide comprising between 19-21 amino acids also decreases or prevents loss of cortical neurons via blocking stress granule aggregation.

14. The method of claim 9, wherein the stress granules being blocked comprise G3BP1, TIA1, FMRP, FXR, TDP43 and/or FUS-TLS.

* * * * *